(12) United States Patent
Kubota et al.

(10) Patent No.: US 7,985,491 B2
(45) Date of Patent: Jul. 26, 2011

(54) ANTHRYLARYLENE DERIVATIVE, MATERIAL FOR ORGANIC ELECTROLUMINESCENCE DEVICE AND ORGANIC ELECTROLUMINESCENCE DEVICE USING SAME

(75) Inventors: Mineyuki Kubota, Chiba (JP); Masakazu Funahashi, Chiba (JP); Chishio Hosokawa, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 877 days.

(21) Appl. No.: 11/390,444

(22) Filed: Mar. 28, 2006

(65) Prior Publication Data

US 2007/0088185 A1    Apr. 19, 2007

(30) Foreign Application Priority Data

Mar. 28, 2005  (JP) ................................. 2005-092604

(51) Int. Cl.
*H01L 51/54* (2006.01)

(52) U.S. Cl. ........ 428/690; 428/917; 313/504; 313/506; 252/301.16; 257/40; 257/103; 257/E51.04; 585/26

(58) Field of Classification Search ................ 428/690, 428/917; 313/504, 506; 257/40, 88–90, 257/E51.049–E51.051; 252/301.16; 548/528; 585/26, 407

See application file for complete search history.

(56) References Cited

U.S. PATENT DOCUMENTS

| 5,635,308 | A * | 6/1997 | Inoue et al. ................... 428/696 |
| 7,504,526 | B2 * | 3/2009 | Kubota et al. ................. 552/218 |
| 2001/0051285 | A1 * | 12/2001 | Shi et al. ....................... 428/690 |
| 2002/0028346 | A1 | 3/2002 | Shi et al. |
| 2002/0048687 | A1 | 4/2002 | Hosokawa et al. |
| 2002/0177009 | A1 | 11/2002 | Suzuki et al. |
| 2004/0214035 | A1 | 10/2004 | Ikeda et al. |
| 2005/0089717 | A1 * | 4/2005 | Cosimbescu et al. ......... 428/690 |
| 2006/0043858 | A1 * | 3/2006 | Ikeda et al. ................... 313/250 |

FOREIGN PATENT DOCUMENTS

| EP | 1 333 018 | | 8/2003 |
| EP | 1 491 609 | | 12/2004 |
| EP | 1 496 041 | A1 | 1/2005 |
| EP | 1 541 657 | | 6/2005 |
| EP | 1 553 154 | | 7/2005 |
| EP | 1 582 516 | | 10/2005 |
| EP | 1 707 550 | A1 | 10/2006 |
| EP | 1 754 696 | A1 | 2/2007 |
| EP | 1 847 521 | A1 | 10/2007 |
| JP | 3-200889 | | 9/1991 |
| JP | 7-138561 | | 5/1995 |
| JP | 8-12600 | | 1/1996 |
| JP | 8-239655 | | 9/1996 |
| JP | 11-3782 | | 1/1999 |
| JP | 2000-182776 | | 6/2000 |
| JP | 2000-273056 | | 10/2000 |
| JP | 2001-257074 | | 9/2001 |
| JP | 2004-59535 | | 2/2004 |
| JP | 2005-019327 | | 1/2005 |
| WO | WO 2004/018587 | A1 | 3/2004 |
| WO | WO 2005/091686 | | 9/2005 |

OTHER PUBLICATIONS

C. W. Tang, et al., "Organic Electroluminescent Diodes", Applied Physics Letters, vol. 51, No. 12, Sep. 21, 1987, pp. 913-915.

* cited by examiner

*Primary Examiner* — D. Lawrence Tarazano
*Assistant Examiner* — Michael H Wilson
(74) *Attorney, Agent, or Firm* — Oblon, Spivak, McClelland, Maier & Neustadt, L.L.P.

(57) ABSTRACT

An anthrylarylene derivative having a specific structure and an organic electroluminescence device comprising an organic thin film layer which comprises at least one layer comprising at least a light emitting layer and is disposed between a cathode and an anode, wherein at least one layer in the organic thin film layer comprises the anthrylarylene derivative singly or as a component of a mixture. The device exhibits a great efficiency of light emission and has a long life. The anthrylarylene derivative has a sufficient glass transition temperature and is greatly advantageous as the light emitting material used in the above organic electroluminescence device.

6 Claims, No Drawings

ANTHRYLARYLENE DERIVATIVE, MATERIAL FOR ORGANIC ELECTROLUMINESCENCE DEVICE AND ORGANIC ELECTROLUMINESCENCE DEVICE USING SAME

TECHNICAL FIELD

The present invention relates to an anthrylarylene derivative, a material for organic electroluminescence devices utilizing the derivative and an organic electroluminescence device. More particularly, the present invention relates to an organic electroluminescence device exhibiting a great luminance of emitted light and a great efficiency of light emission and having a long life and a novel anthrylarylene derivative realizing the device.

BACKGROUND ART

An organic electroluminescence ("electroluminescence" will be referred to as "EL", hereinafter) device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used a laminate structure using tris(8-hydroxyquinolinolato)aluminum for the light emitting layer and a triphenyldiamine derivative for the hole transporting layer. Advantages of the laminate structure are that the efficiency of hole injection into the light emitting layer can be increased, that the efficiency of forming excitons which are formed by blocking and recombining electrons injected from the cathode can be increased, and that excitons formed within the light emitting layer can be enclosed. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

As the light emitting material of the organic EL device, chelate complexes such as tris(8-quinolinolato)aluminum complex, coumarine derivatives, tetraphenylbutadiene derivatives, bisstyrylarylene derivatives and oxadiazole derivatives are known. It is reported that light in the visible region ranging from blue light to red light can be obtained by using these light emitting materials, and development of a device exhibiting color images is expected (for example, Patent Reference 1, Patent Reference 2 and Patent Reference 3).

A device using a phenylanthracene derivative as the light emitting material is disclosed in Patent Reference 4. A material in which naphthyl groups are bonded at the 9- and 10-positions of anthracene is disclosed in Patent Reference 5. These anthracene derivatives are used as the material emitting blue light. However, an improvement in the life of the device has been required.

A material in which fluoranthene groups are bonded at the 9- and 10-positions of anthracene is disclosed in Patent Reference 6. This anthracene derivative is used as the material emitting blue light. However, an improvement in the life of the device has been required.

It is disclosed in Patent Reference 7 that various anthracene derivatives are used as the hole transporting material. However, the evaluation of these compounds as the light emitting material has not been made.

It is disclosed in Patent Reference 8 that devices using asymmetric anthracene derivatives as the material emitting blue light exhibit great efficiencies of light emission and have long lives. Although the asymmetric anthracene derivatives are excellent materials emitting blue light, some of the derivatives have a drawback in that the glass transition temperature (Tg) is rather low, and an improvement in Tg has been desired.

[Patent Reference 1] Japanese Patent Application Laid-Open No. Heisei 8(1996)-239655

[Patent Reference 2] Japanese Patent Application Laid-Open No. Heisei 7(1995)-138561

[Patent Reference 2] Japanese Patent Application Laid-Open No. Heisei 3(1991)-200889

[Patent Reference 4] Japanese Patent Application Laid-Open No. Heisei 8(1996)-12600

[Patent Reference 5] Japanese Patent Application Laid-Open No. Heisei 11(1999)-3782

[Patent Reference 6] Japanese Patent Application Laid-Open No. 2001-257074

[Patent Reference 7] Japanese Patent Application Laid-Open No. 2000-182776

[Patent Reference 8] WO 2004-18587

DISCLOSURE OF THE INVENTION

The present invention has been made to overcome the above problems and has an object of providing an organic EL device exhibiting a great efficiency of light emission and having a long life. The present invention has a further object of providing an anthrylarylene derivative having a sufficient glass transition temperature and advantageously used as the light emitting material in the organic electroluminescence device of the present invention.

As the result of intensive studies to achieve the above objects, it was found that anthrylarylene derivatives represented by the following general formulae (I) to (III) had improved glass transition temperatures and organic EL devices exhibiting a great efficiency of light emission and having a long life could be prepared when the anthrylarylene derivatives were used as the light emitting material.

As the first means of achieving the object of the present invention, anthrylarylene derivatives represented by the following general formulae (I) to (III) are provided:

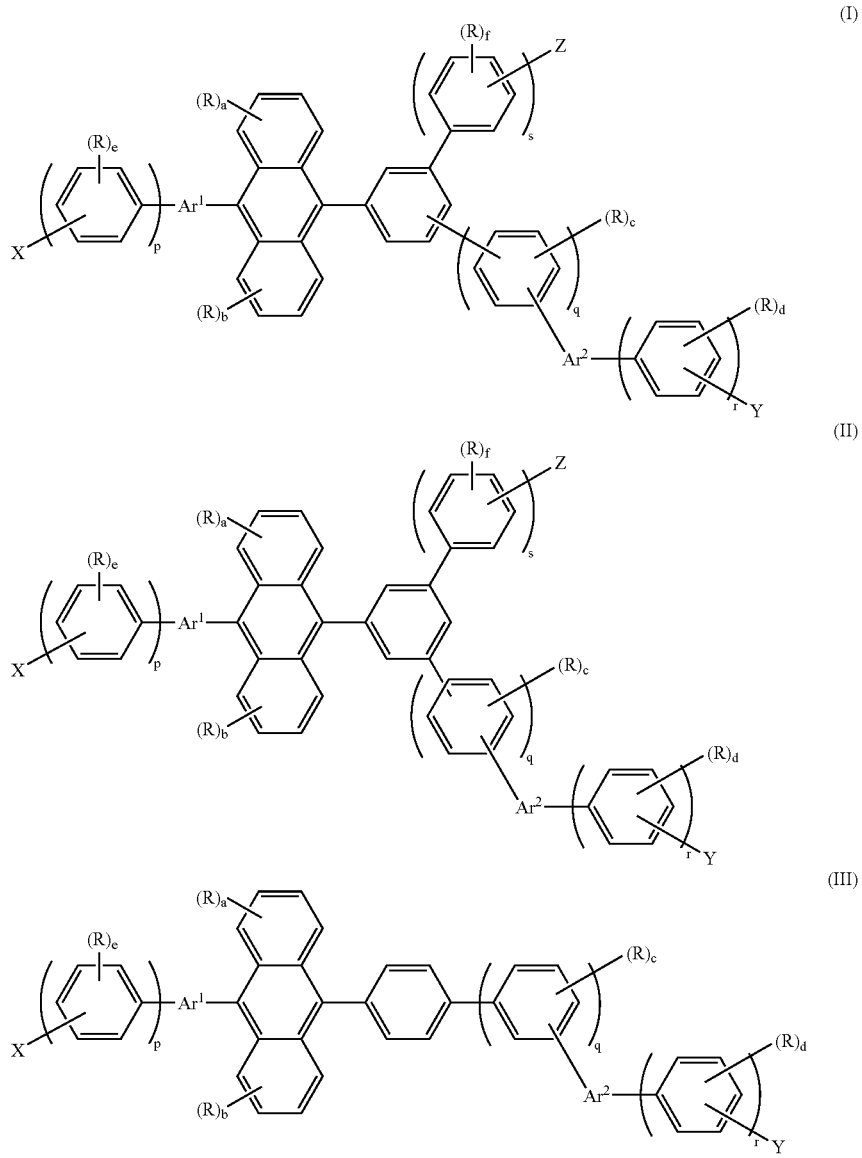

As the second means of achieving the object of the present invention, a material for organic EL devices comprising the anthrylarylene derive represented by any one of the above general formulae (I) to (III) singly or as a component of a mixture is provided.

As the third means of achieving the object of the present invention, an organic EL device which comprises a cathode, an anode and an organic thin film layer which comprises at least one layer comprising at least a light emitting layer and is disposed between the cathode and the anode, wherein at least one layer in the organic thin film layer comprises the above material for organic EL devices, is prepared.

The Effect of the Invention

The present invention has been made to achieve the above objects, and an organic EL device exhibiting a great efficiency of light emission and having a long life can be provided. An anthrylarylene derivative having a sufficient glass transition temperature and advantageously used as the light emitting material in the above organic EL device can be provided.

THE MOST PREFERRED EMBODIMENT TO CARRY OUT THE INVENTION

As the first aspect of the present invention, anthrylarylene derivatives represented by the above general formulae (I) to (III) are provided.

In general formulae (I) to (III), $Ar^1$ represents a substituted or unsubstituted aromatic hydrocarbon group having 6 to 50 nuclear carbon atoms, a carbazolylene group represented by following general formula (A) or a triptycenylene group represented by following general formula (B), and $Ar^2$ represents a substituted or unsubstituted aromatic hydrocarbon group having 6 to 50 nuclear carbon atoms, a carbazolylene group represented by following general formula (A), a triptycenylene group represented by following general formula (B) or a fluorenylene group represented by following general formula (C):

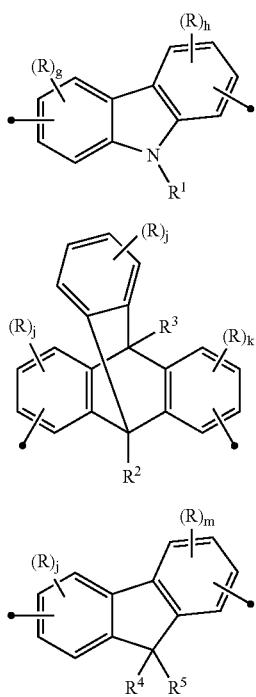

In the above general formulae (A) to (C), $R^1$ to $R^5$ each independently represent hydrogen atom, an aromatic hydrocarbon group, an aromatic heterocyclic group, an alkyl group, a cycloalkyl group, an alkoxy group, an aralkyl group, an aryloxy group, an arylthio group, an alkoxycarbonyl group, a silyl group, carboxyl group, a halogen atom, cyano group, nitro group or hydroxyl group, and $R^1$ to $R^5$ may each represent a linking group.

In general formulae (I) to (III) and (A) to (C), a plurality of R each independently represent an aromatic hydrocarbon group, an aromatic heterocyclic group, an alkyl group, a cycloalkyl group, an alkoxy group, an aralkyl group, an aryloxy group, an arylthio group, an alkoxycarbonyl group, a silyl group, carboxyl group, a halogen atom, cyano group, nitro group or hydroxyl group.

In general formulae (I) to (III) and (A) to (C), when R and $R^1$ to $R^5$ represent alkyl groups, adjacent alkyl groups may be bonded to each other to form a condensed ring.

a to m each independently represent an integer of 0 to 4, p, q, r and s each independently represent an integer of 0 to 3, and substituents represented by a plurality of R on each benzene ring may be the same with or different from each other.

X, Y, and Z each independently represent hydrogen atom, an aromatic hydrocarbon group having 6 to 30 nuclear carbon atoms or an aromatic heterocyclic group having 5 to 30 nuclear carbon atoms, and Y does not represent hydrogen atom when p=q=r=0.

Examples of the substituted or unsubstituted aromatic hydrocarbon group having 6 to 50 nuclear carbon atoms represented by $Ar^1$ and $Ar^2$ and the aromatic hydrocarbon group represented by R in the above general formulae (I) to (III) and the aromatic hydrocarbon group represented by $R^1$ to $R^5$ in the above general formulae (A) to (C) include phenyl group, naphthyl group, anthryl group, phenanthryl group, naphthacenyl group, pyrenyl group and chrysenyl group. Examples of the preferable groups include phenyl group, naphthyl group, anthryl group, phenanthryl group and pyrenyl group.

These aromatic hydrocarbon groups may be substituted with substituents. Examples of the substituent include alkyl groups (such as methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamantyl group, 2-adamantyl group, 1-norbornyl group and 2-norbornyl group), alkoxy groups having 1 to 6 carbon atoms (such as ethoxy group, methoxy group, i-propoxy group, n-propoxy group, s-butoxy group, t-butoxy group, pentoxy group, hexyloxy group, cyclopentoxy group and cyclohexyloxy group), aryl groups having 5 to 40 nuclear atoms, amino groups substituted with aryl groups having 5 to 40 nuclear atoms, ester groups having aryl groups having 5 to 40 nuclear atoms, ester groups having alkyl groups having 1 to 6 carbon atoms, cyano group, nitro group and halogen atoms.

Examples of the aromatic heterocyclic group represented by R in general formulae (I) to (III) and $R^1$ to $R^5$ in general formulae (A) to (C) include 1-pyrrolyl group, 2-pyrrolyl group, 3-pyrrolyl group, pyradinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

Examples of the alkyl group represented by R in general formulae (I) to (III) and $R^1$ to $R^5$ in general formulae (A) to (C) include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloro-propyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group.

Examples of the cycloalkyl group represented by R in general formulae (I) to (III) and $R^1$ to $R^5$ in general formulae (A) to (C) include cyclopropyl group, cyclobutyl group, cyclopentyl group, cyclohexyl group, 4-methylcyclohexyl group, 1-adamantyl group, 2-adamantyl group, 1-norbornyl group and 2-norbornyl group.

The alkoxy group represented by R in general formulae (I) to (III) and $R^1$ to $R^5$ in general formulae (A) to (C) is a group represented by —OY. Examples of the group represented by Y include the groups described above as the examples of the alkyl group.

Examples of the aralkyl group represented by R in general formulae (I) to (III) and $R^1$ to $R^5$ in general formulae (A) to (C) include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

The aryloxy group represented by R in general formulae (I) to (III) and $R^1$ to $R^5$ in general formulae (A) to (C) is represented by —OY'. Examples of the group represented by Y' include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyradinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

The arylthio group represented by R in general formulae (I) to (III) and $R^1$ to $R^5$ in general formulae (A) to (C) is a group represented by —SY'. Examples of the group represented by Y' include the groups described above as the examples of the group represented by Y' in the aryloxy group.

The alkoxycarbonyl group represented by R in general formulae (I) to (III) and $R^1$ to $R^5$ in general formulae (A) to (C) is represented by —COOZ. Examples of the group represented by Z include the groups described above as the examples of the alkyl group.

Examples of the silyl group represented by R in general formulae (I) to (III) and $R^1$ to $R^5$ in general formulae (A) to (C) include trimethylsilyl group, triethylsilyl group, t-butyldimethylsilyl group, vinyldimethylsilyl group and propyldimethylsilyl group.

Examples of the halogen atom represented by R in general formulae (I) to (III) and $R^1$ to $R^5$ in general formulae (A) to (C) include fluorine atom, chlorine atom, bromine atom and iodine atom.

Examples of the substituent to the group represented by $R^1$ to $R^5$ include the substituents described as the examples of the substituent to the group represented by $Ar^1$ or $Ar^2$.

Examples of the anthrylarylene derivatives represented by general formulae (I) to (III) of the present invention are shown in the following. However, the anthrylarylene derivative of the present invention is not limited to these compounds.

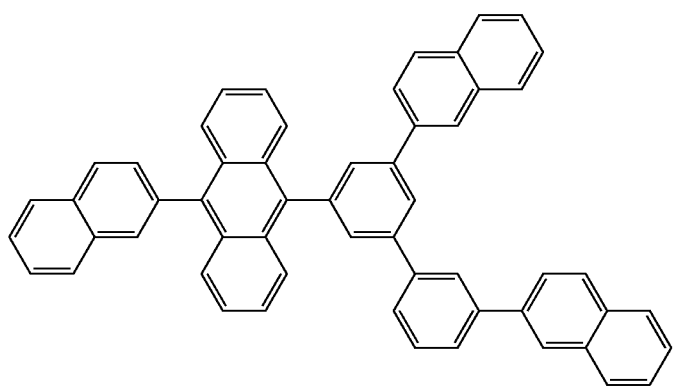

AN-1

-continued
AN-2
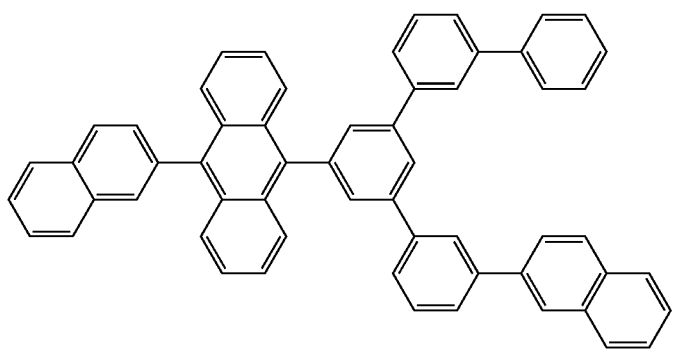
AN-3
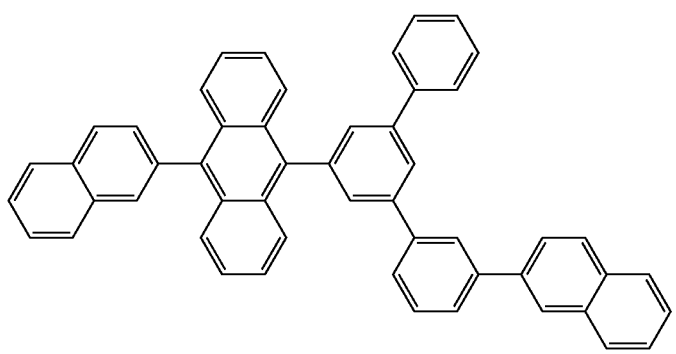
AN-4
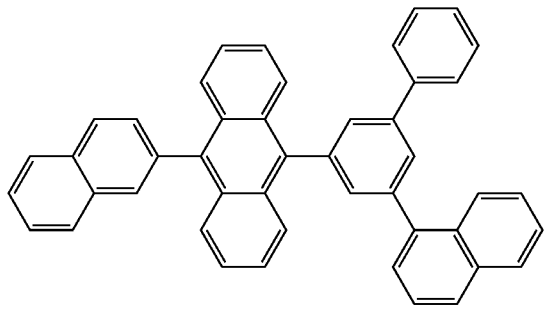
AN-5
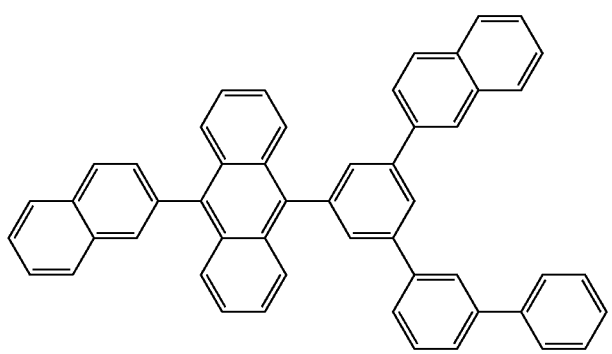

-continued
AN-6
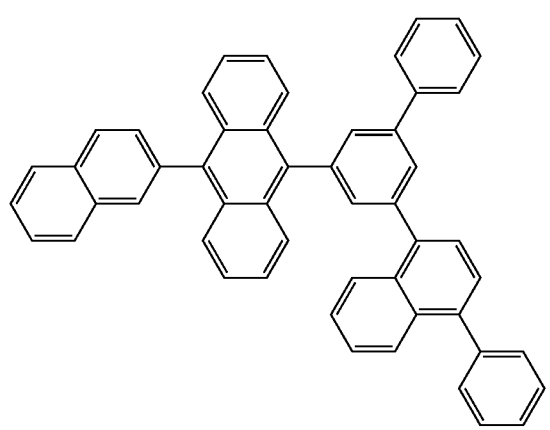
AN-7
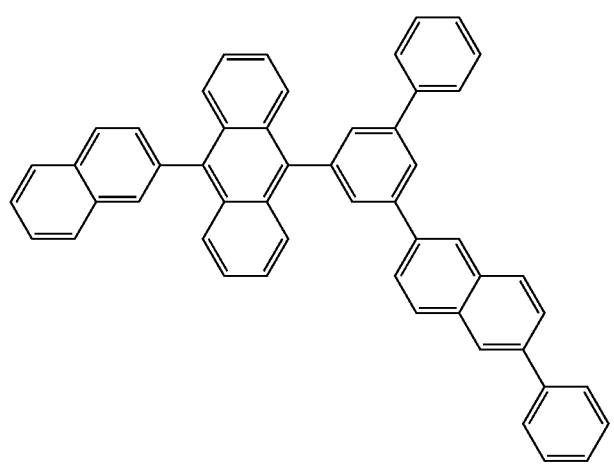
AN-8
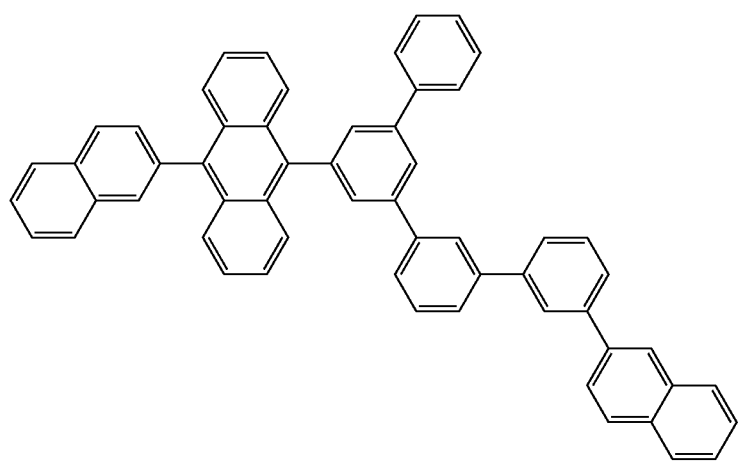

-continued
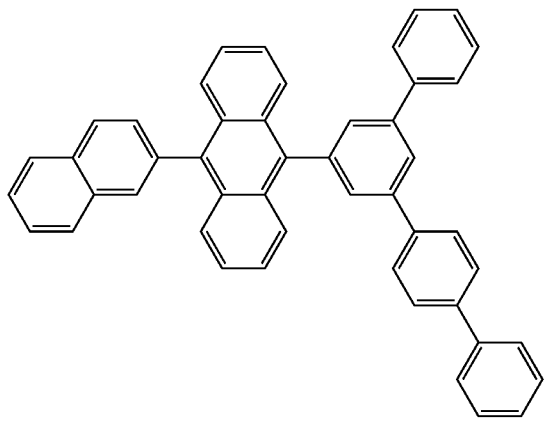
AN-9
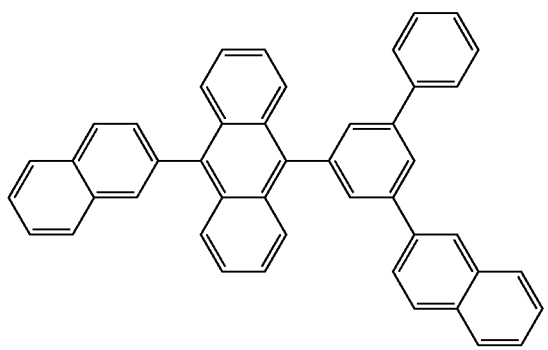
AN-10
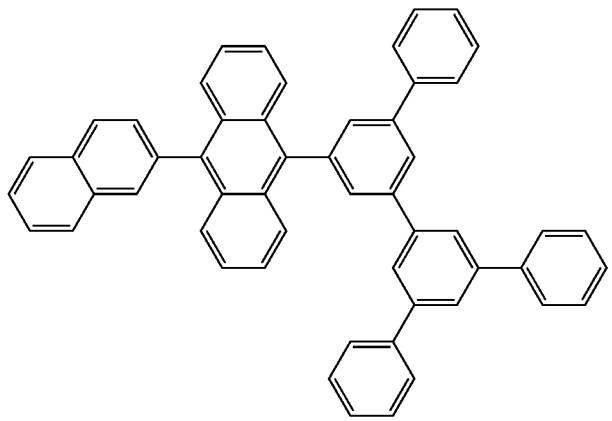
AN-11
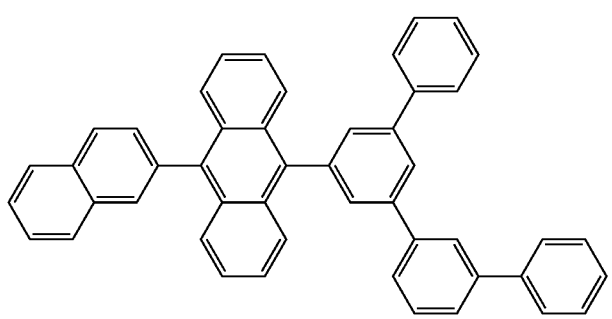
AN-12

-continued
AN-13
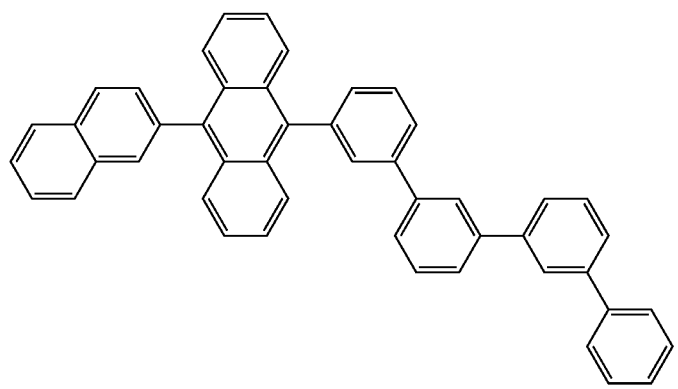
AN-14
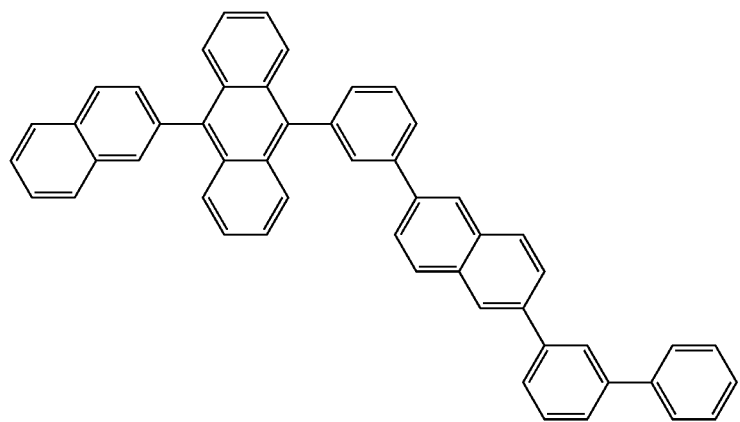
AN-15
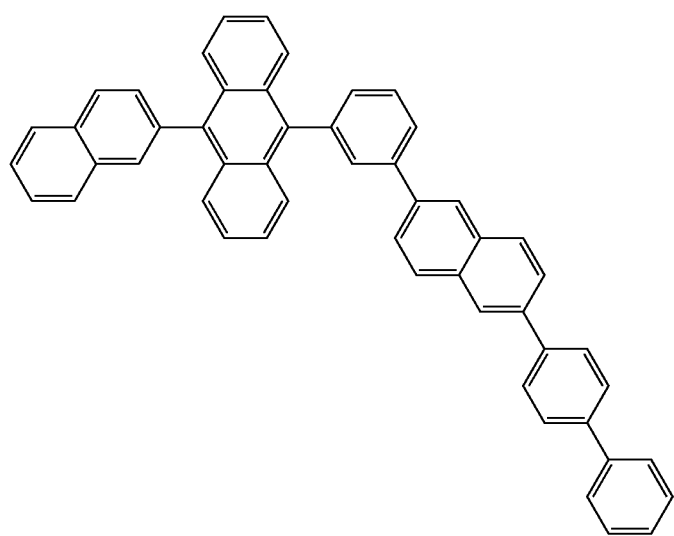

-continued
AN-16
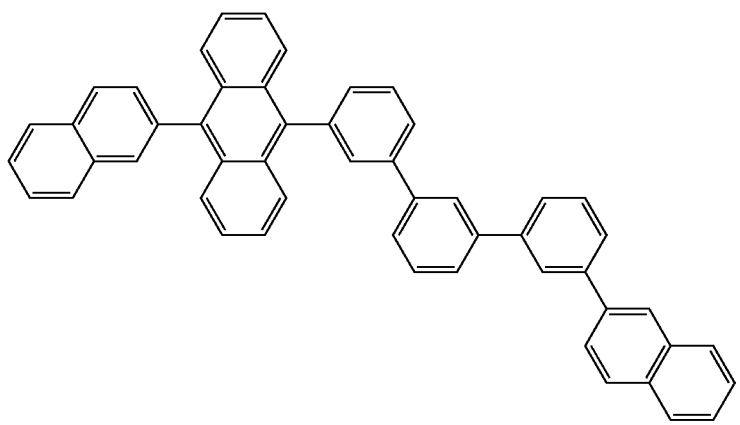
AN-17
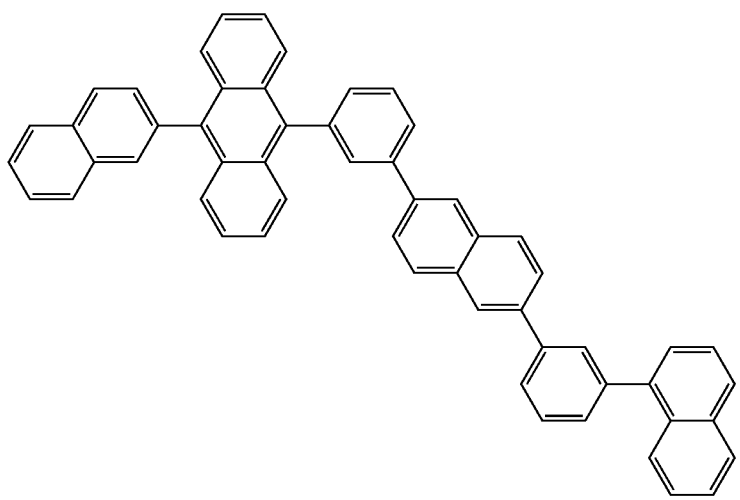
AN-18
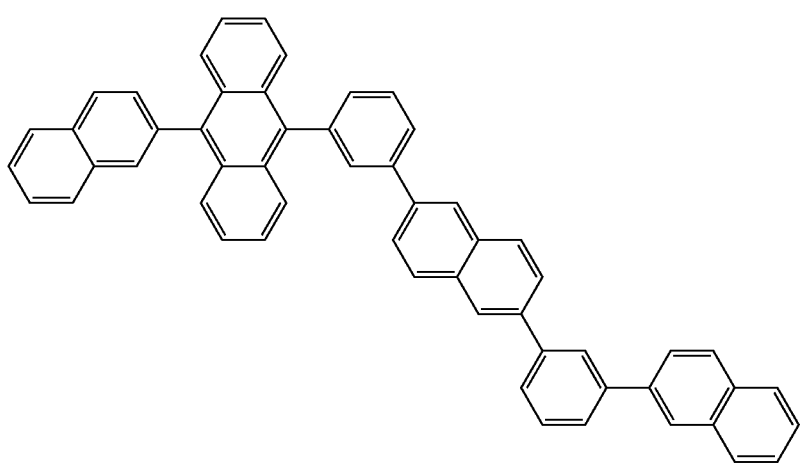

-continued
AN-19
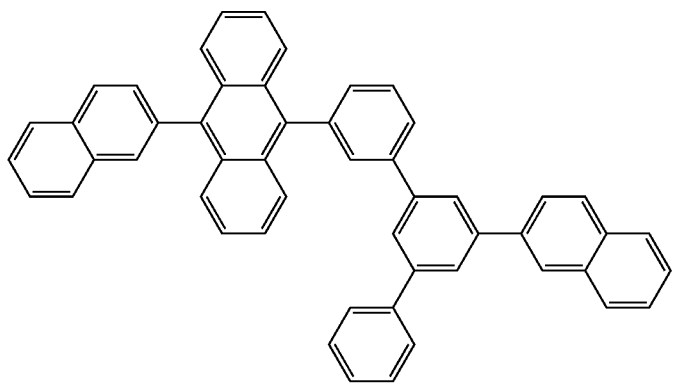
AN-20
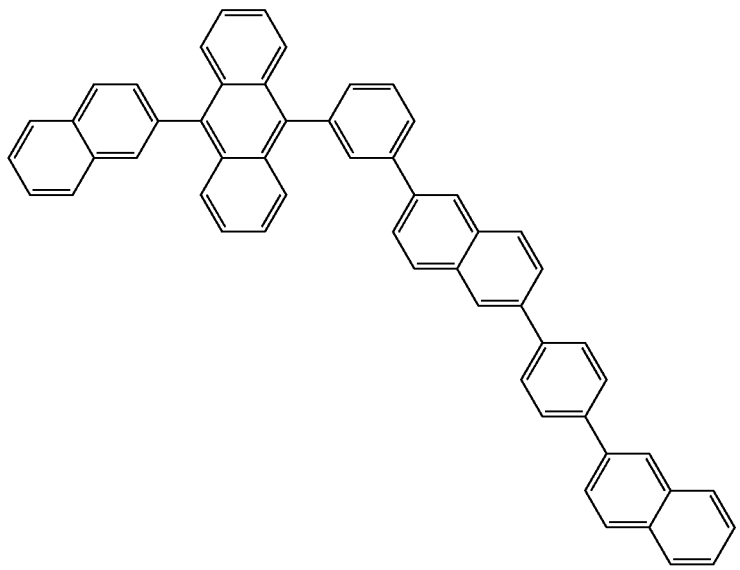
AN-21
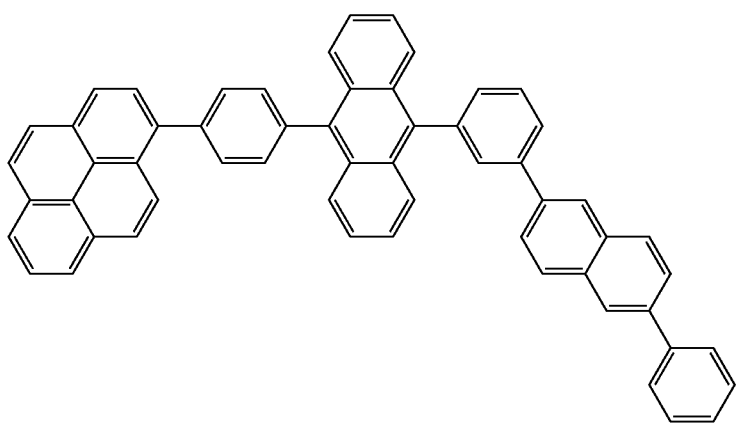

-continued
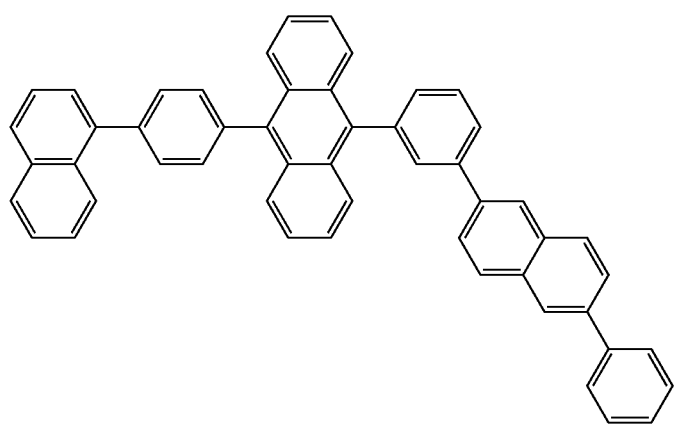
AN-22
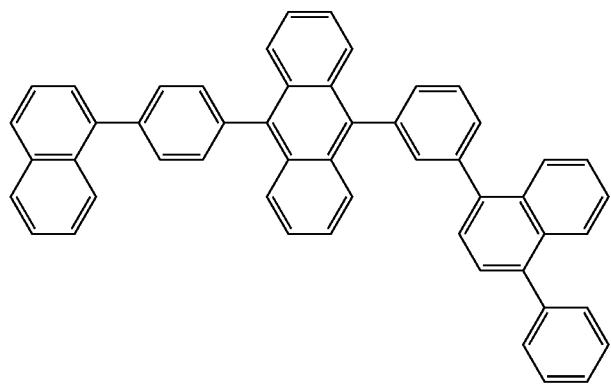
AN-23
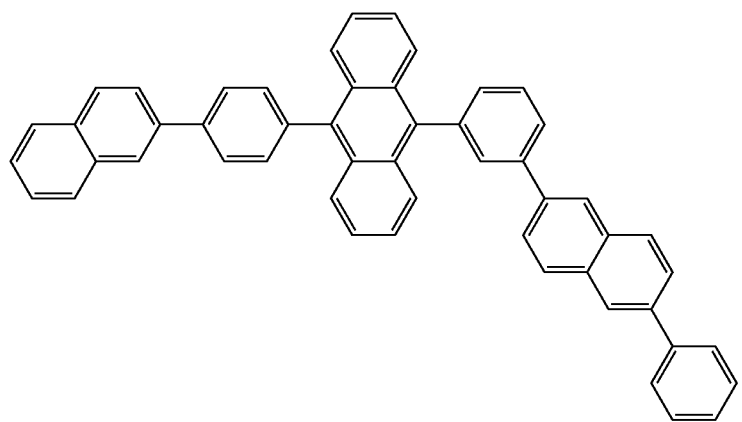
AN-24
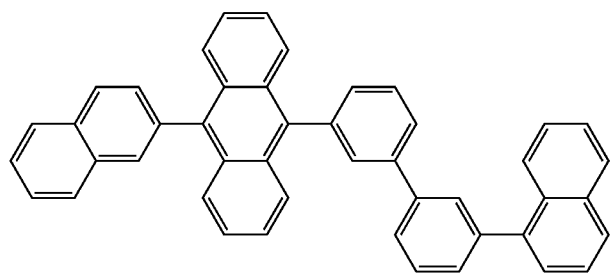
AN-25

-continued
AN-26
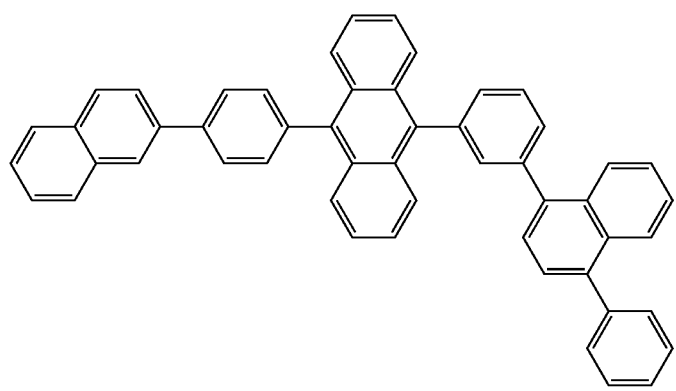
AN-27
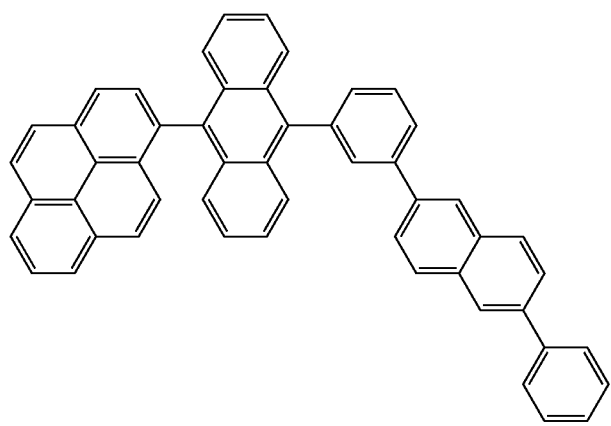
AN-28
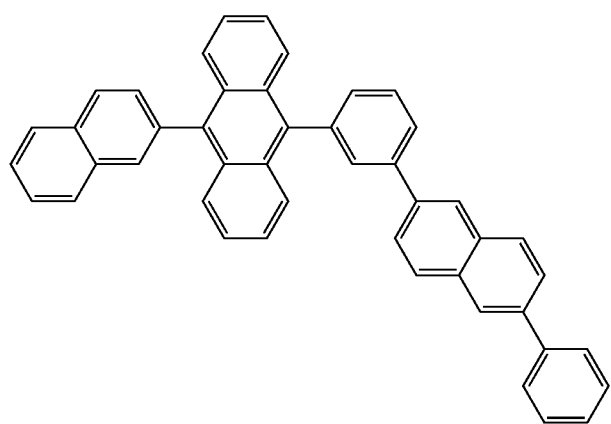
AN-29
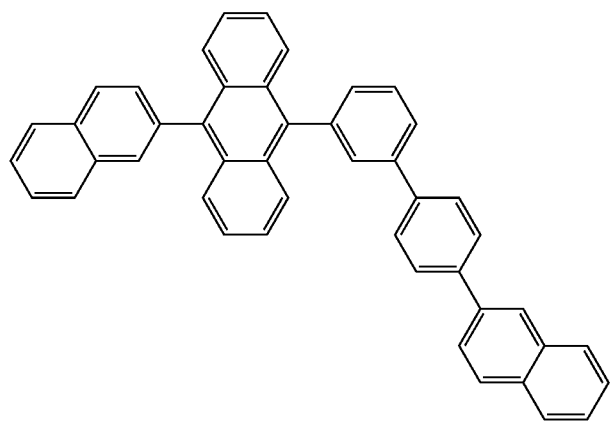

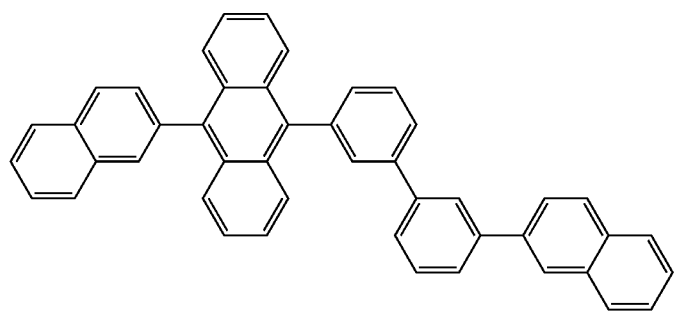
AN-30
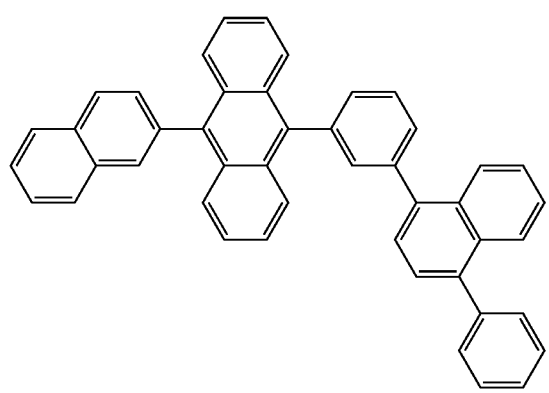
AN-31
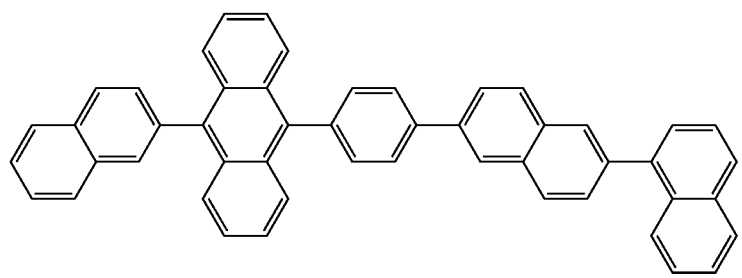
AN-32
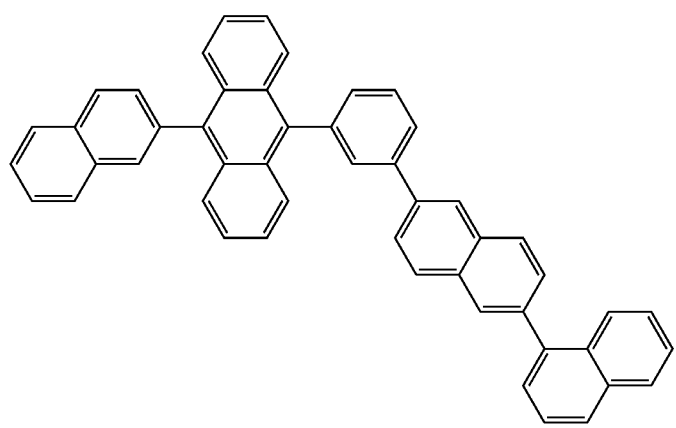
AN-33

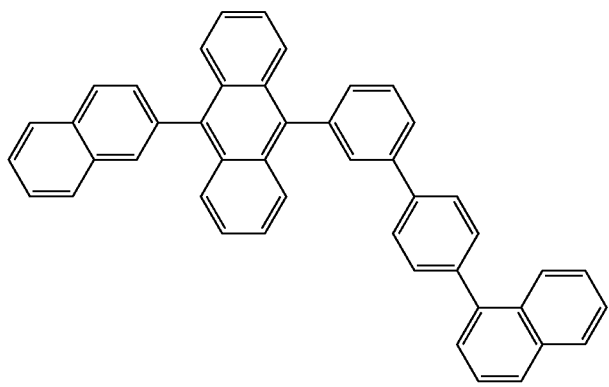
AN-34
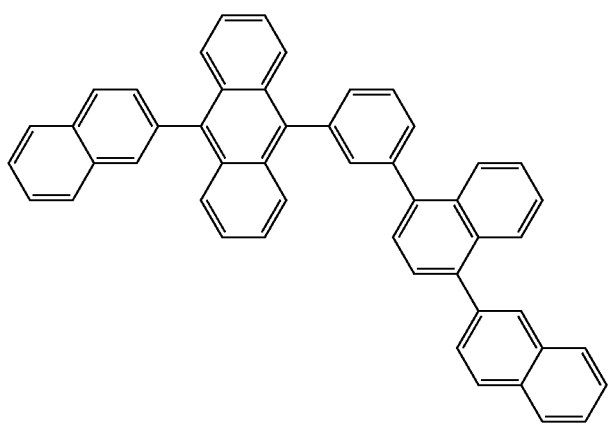
AN-35
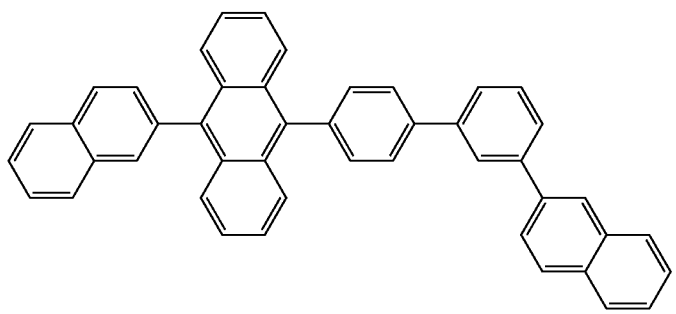
AN-36
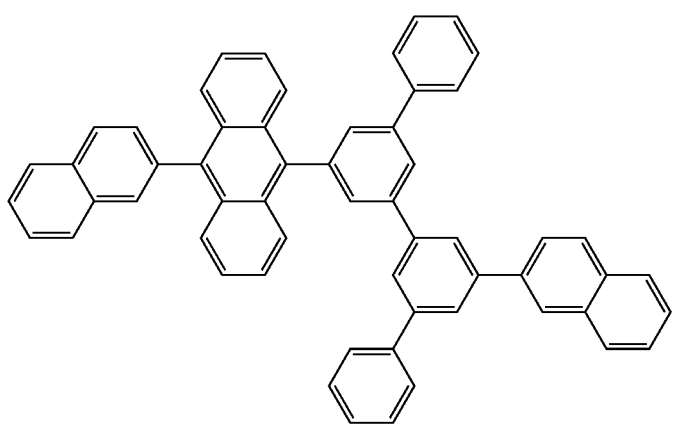
AN-37

-continued
AN-38
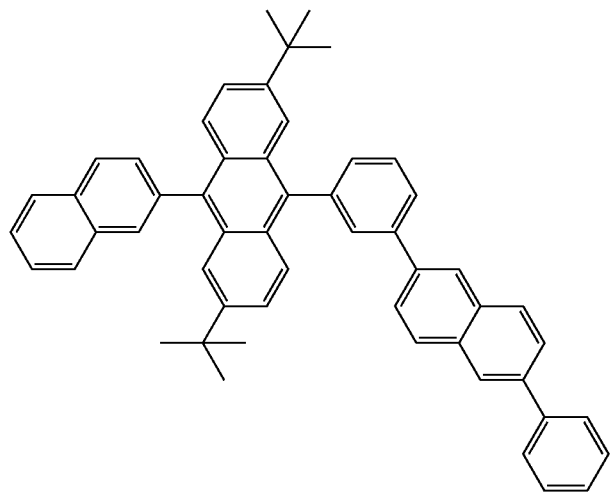
AN-39
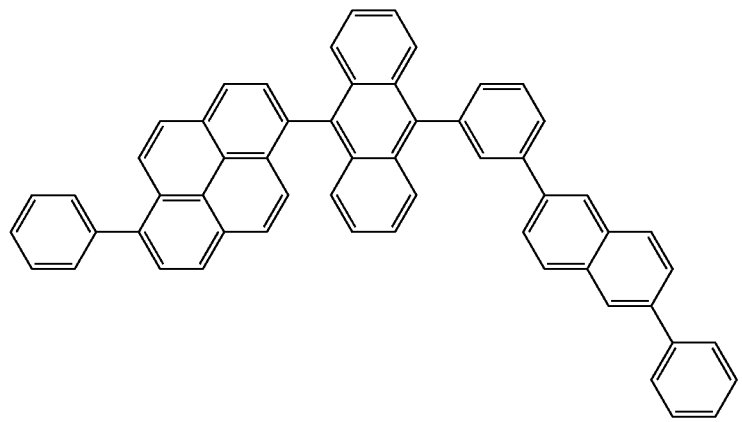
AN-40
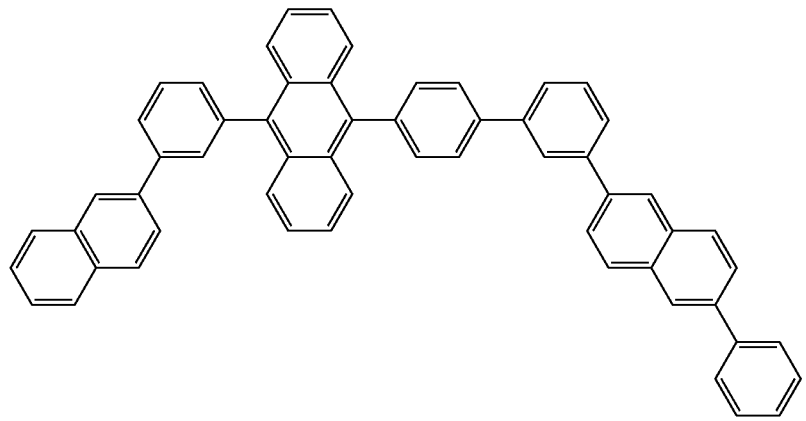
AN-41
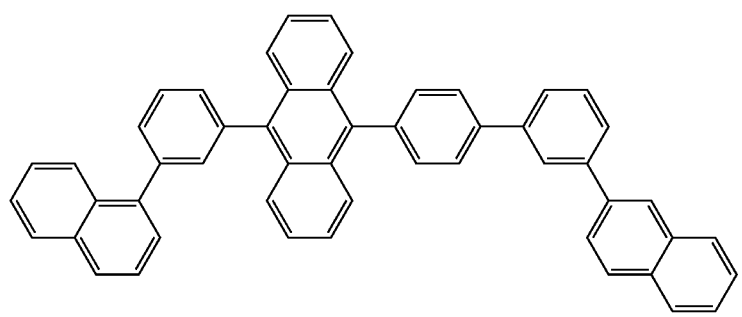

-continued
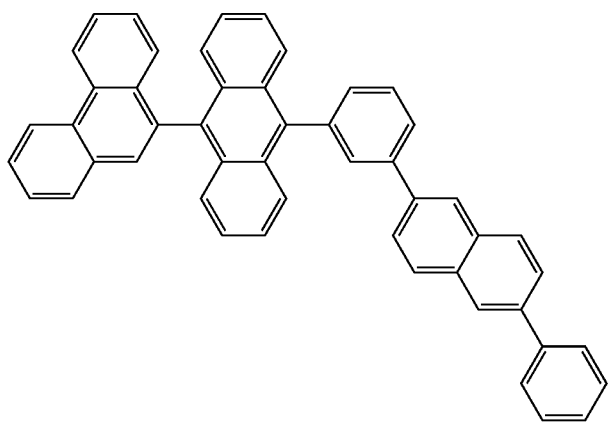
AN-42
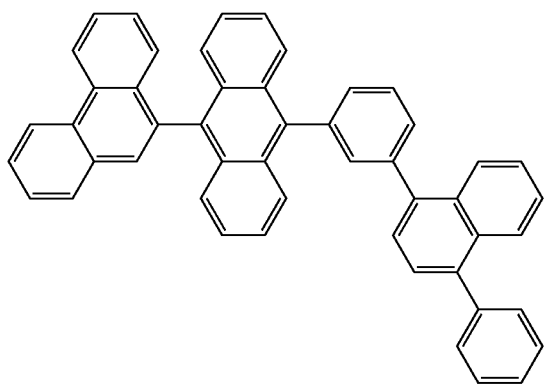
AN-43
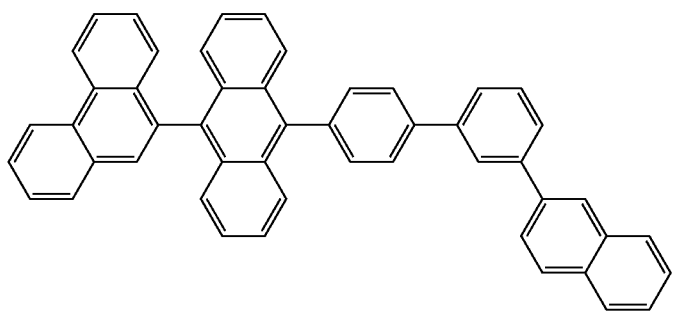
AN-44
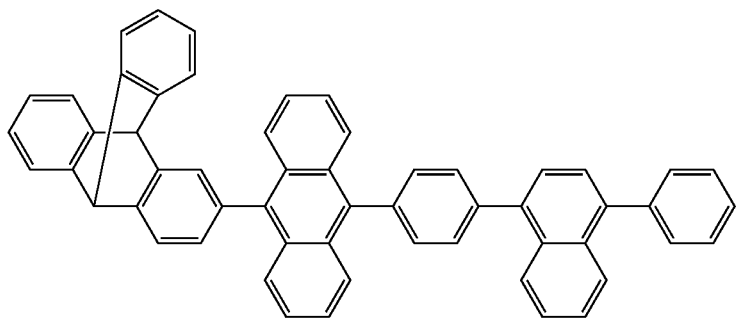
AN-45

AN-46
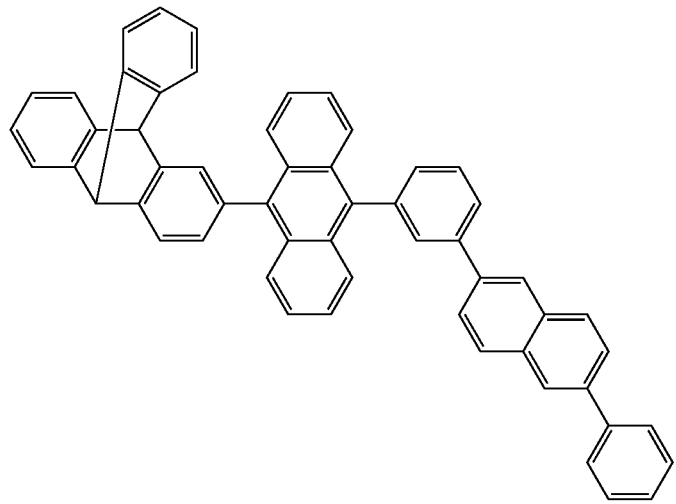
AN-47
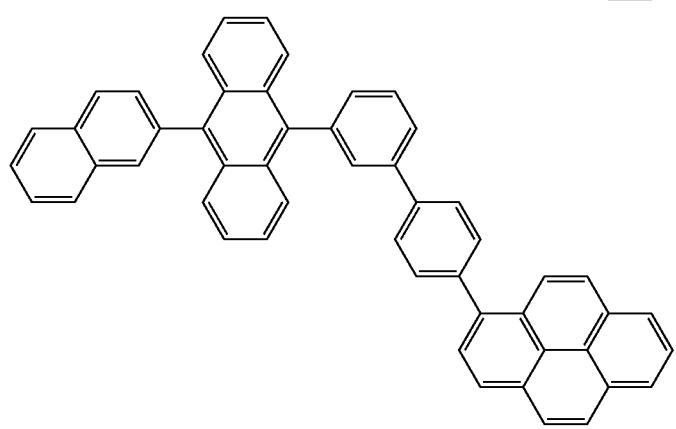
AN-48
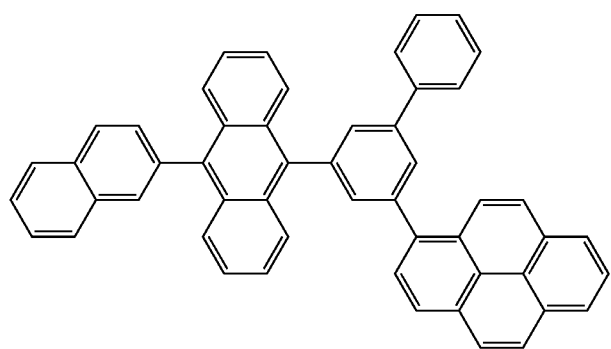
AN-49
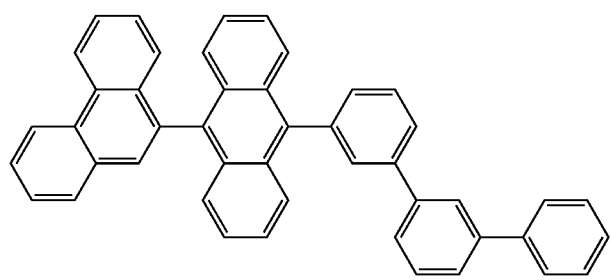

AN-50
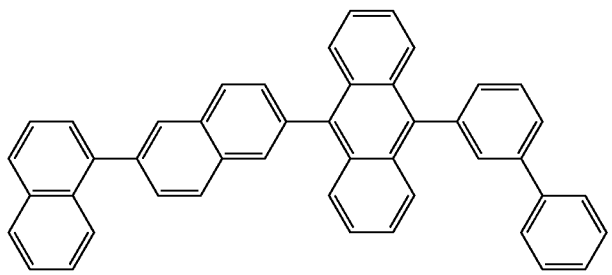
AN-51
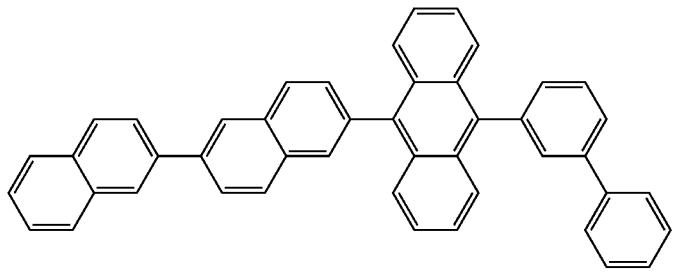
AN-52
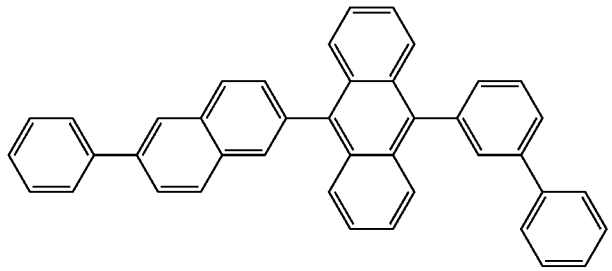
AN-53
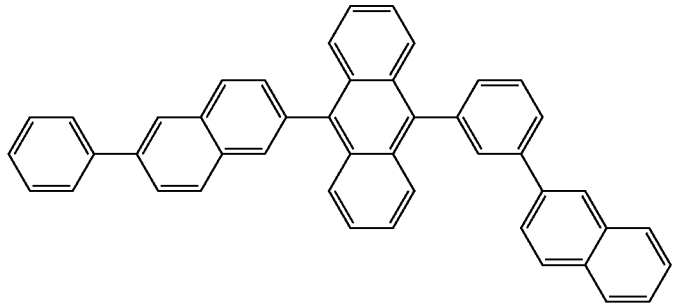
AN-54
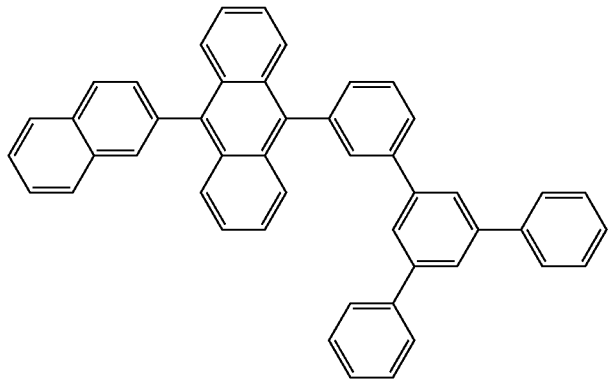

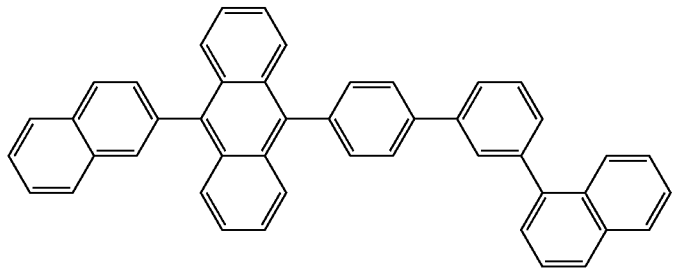
AN-55
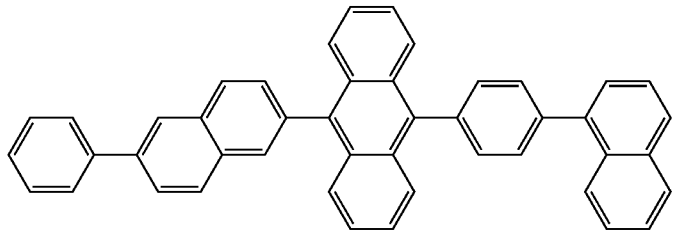
AN-56
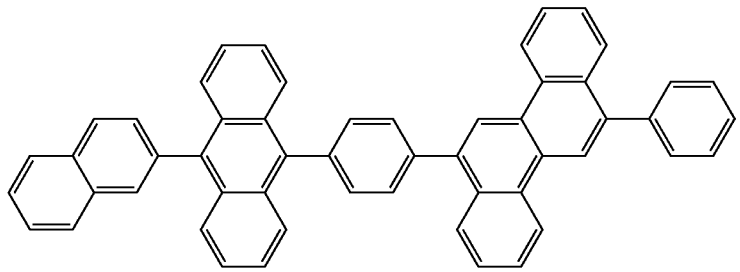
AN-57
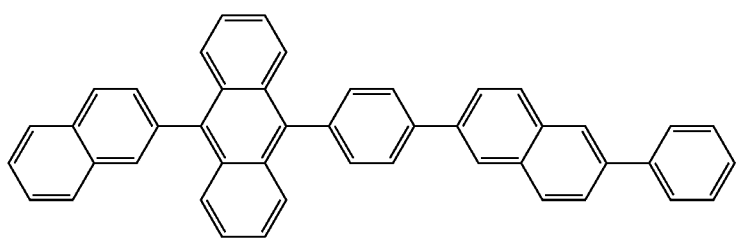
AN-58
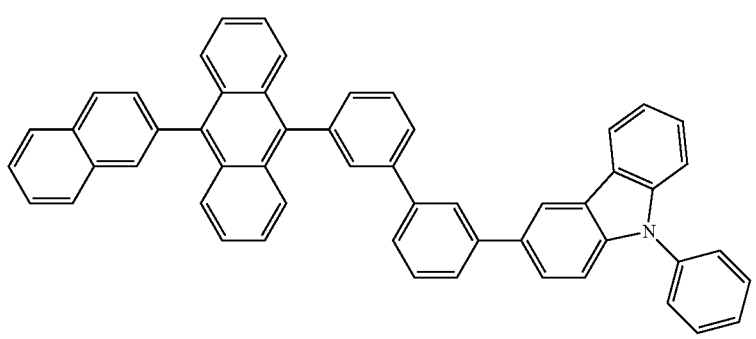
AN-59

AN-60
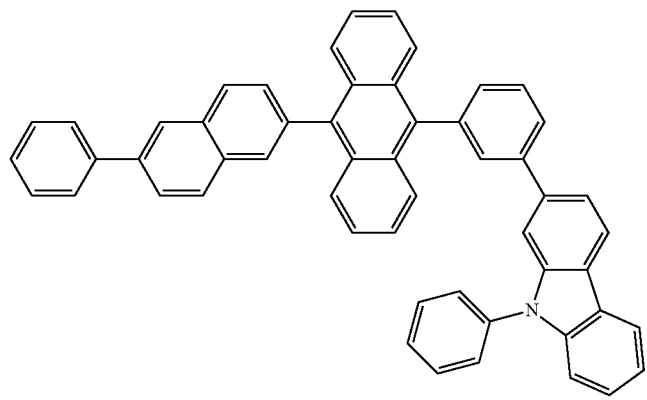
AN-61
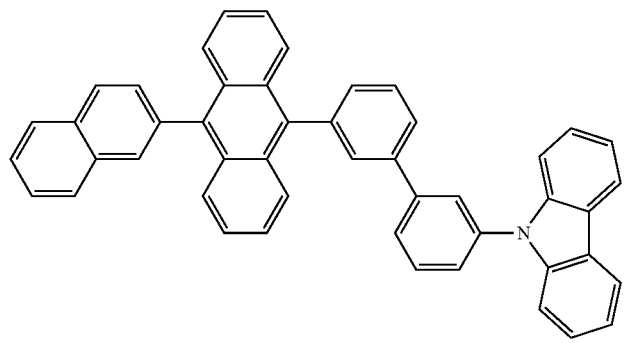
AN-62
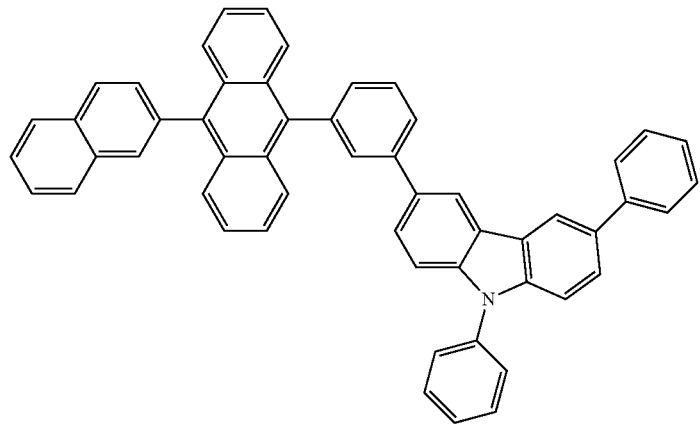
AN-63
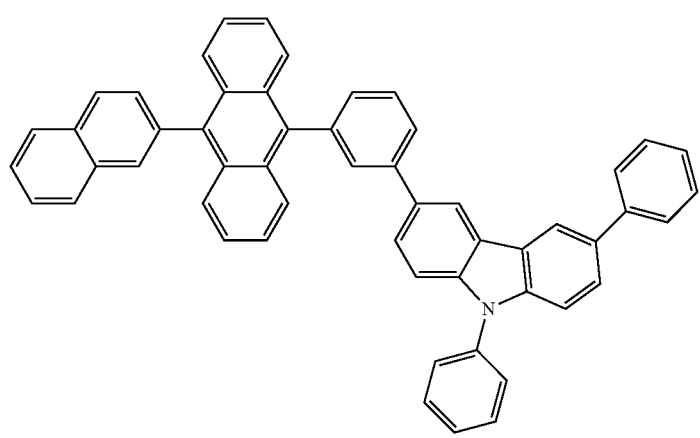

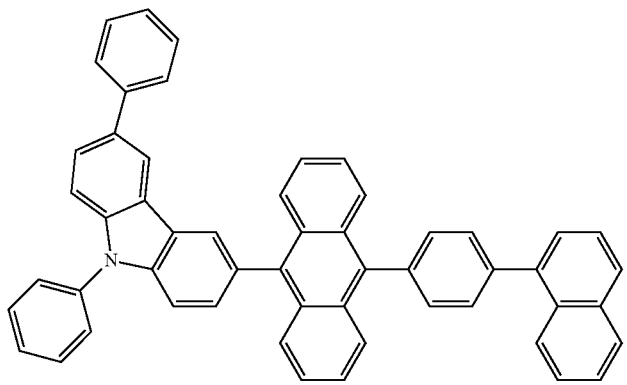
AN-64
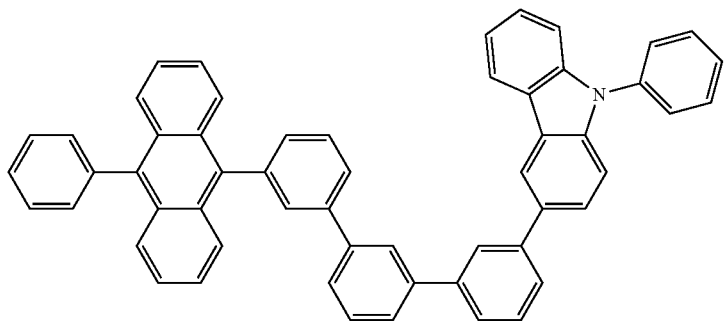
AN-65
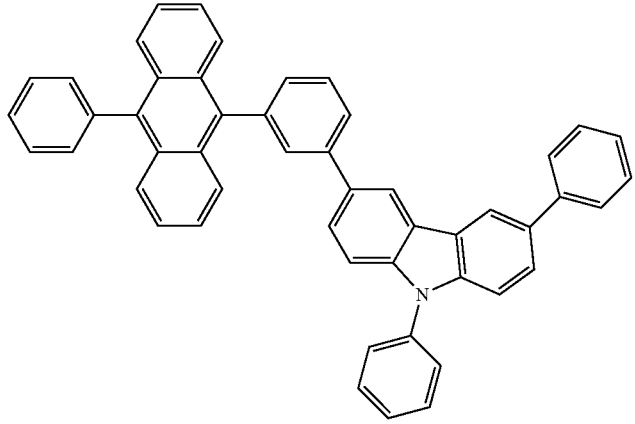
AN-66
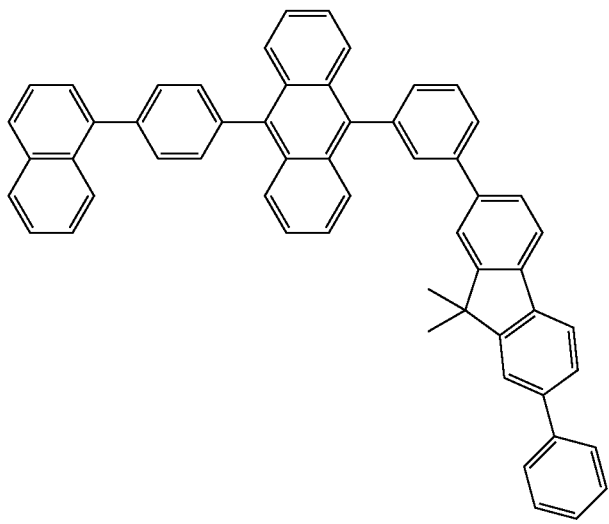
AN-67

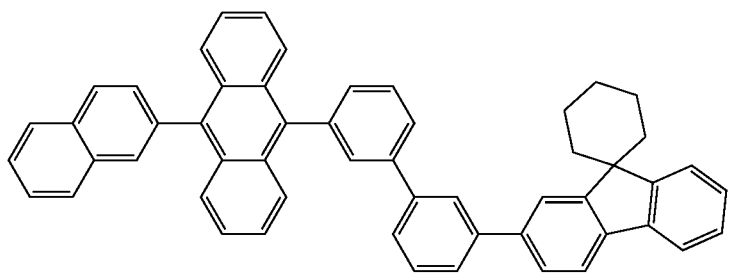
AN-68
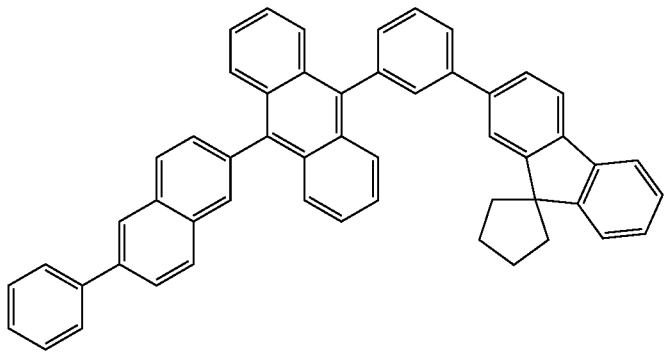
AN-69
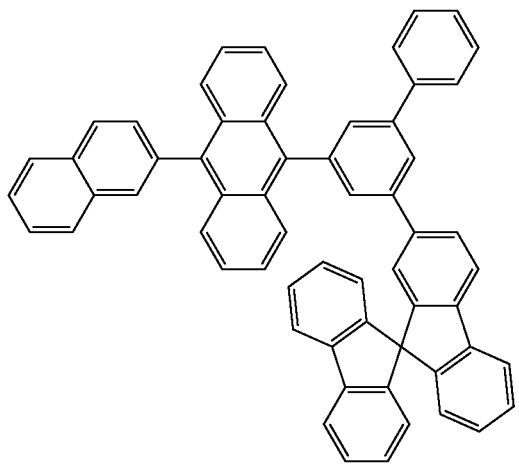
AN-70
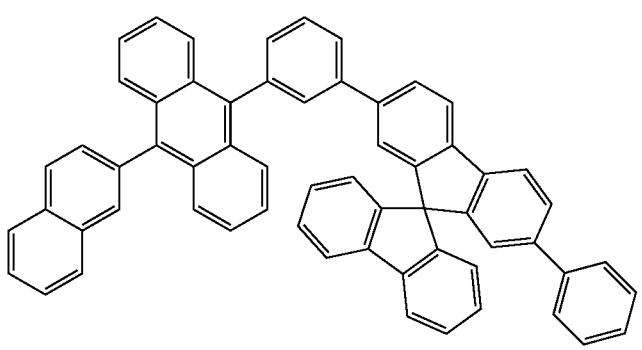
AN-71

-continued
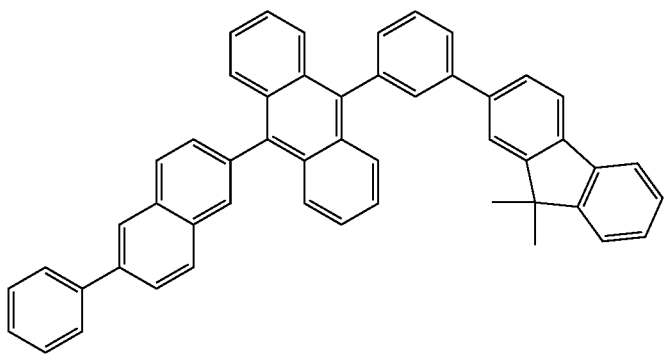
AN-72
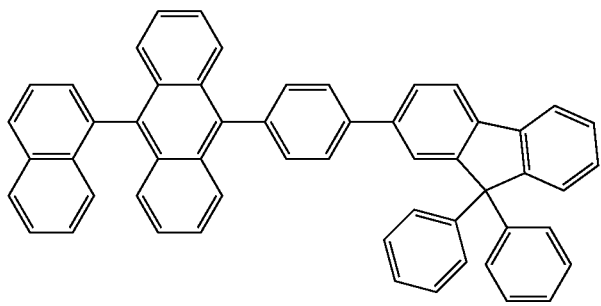
AN-73
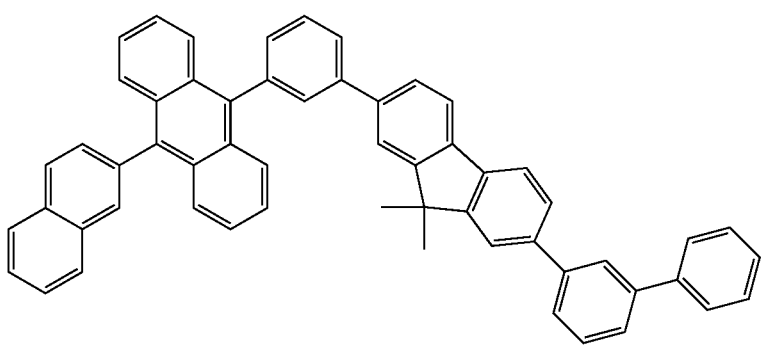
AN-74
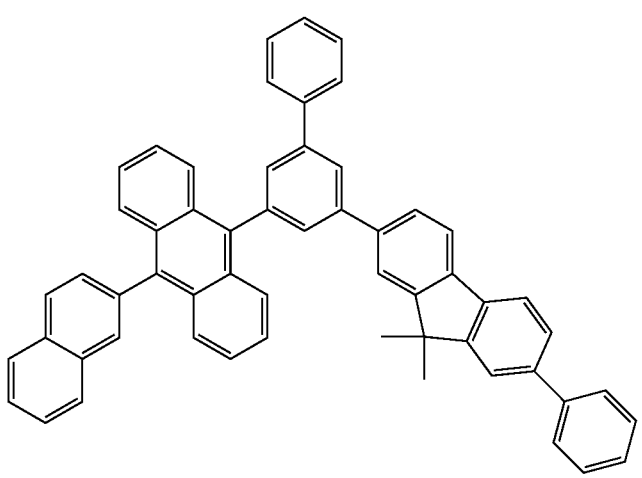
AN-75

-continued
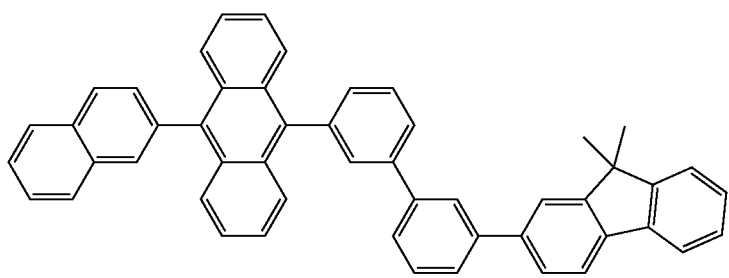
AN-76
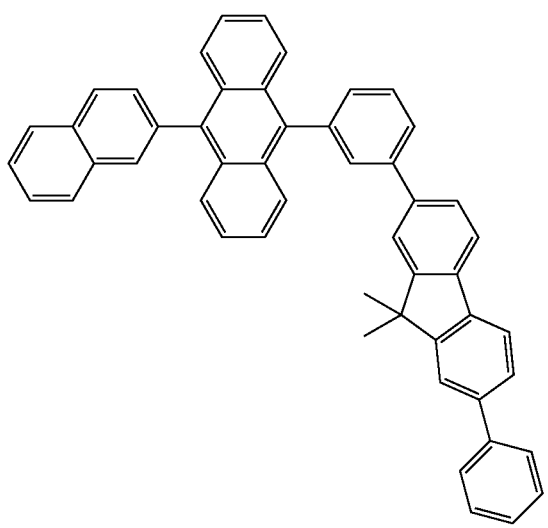
AN-77
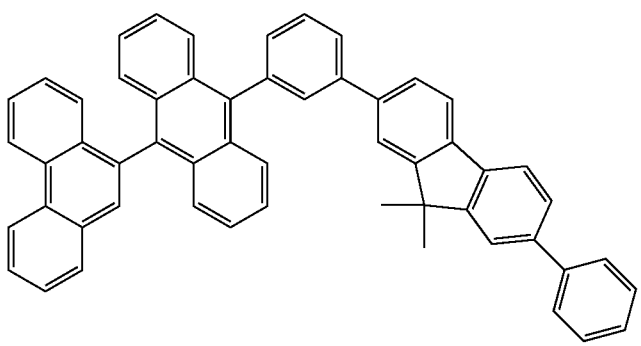
AN-78
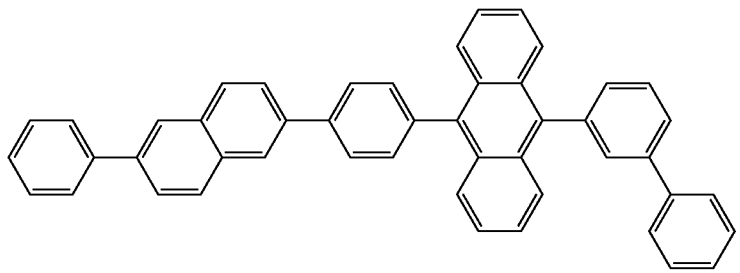
AN-79

-continued
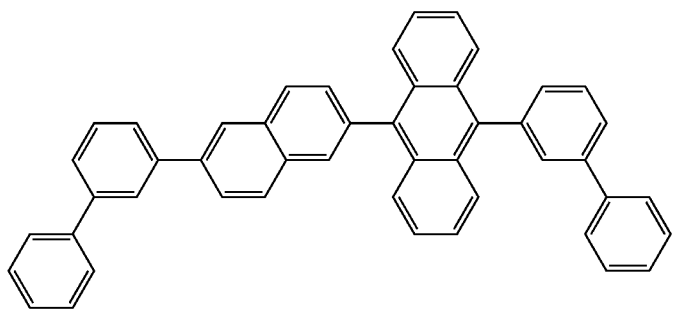
AN-80
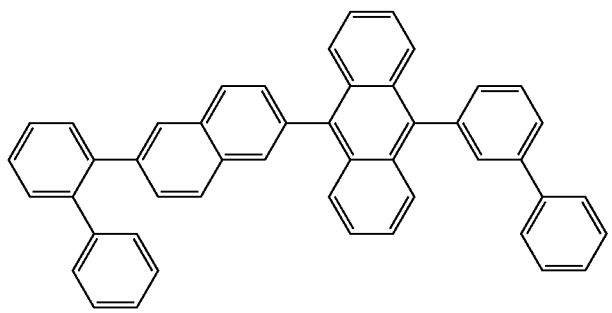
AN-81
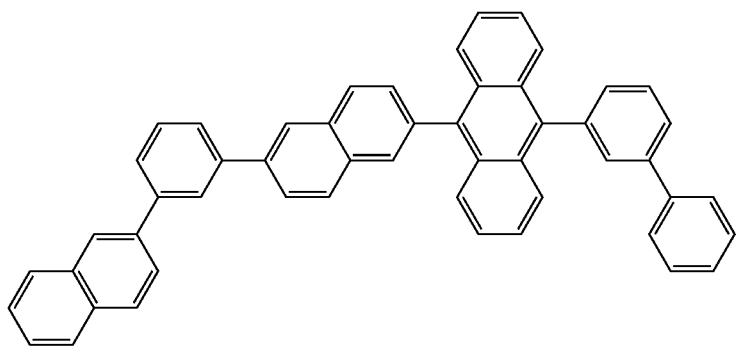
AN-82
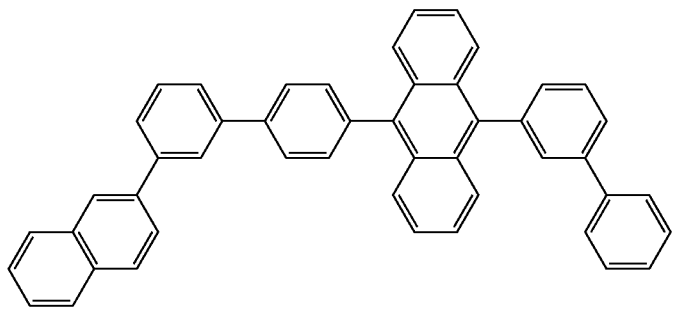
AN-83
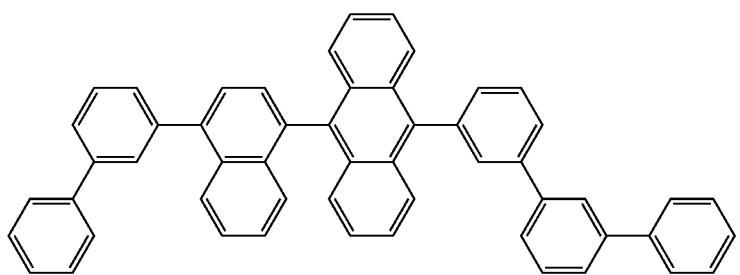
AN-84

-continued
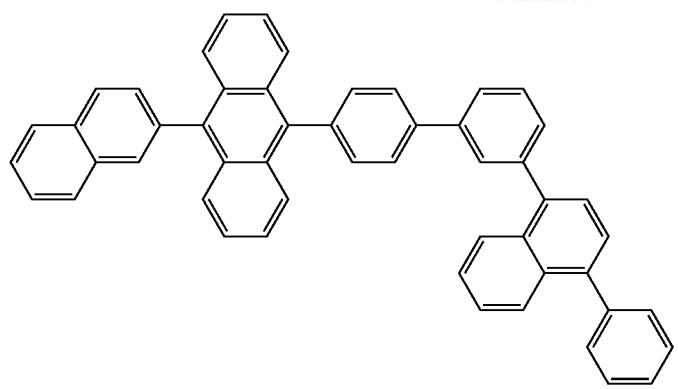
AN-85
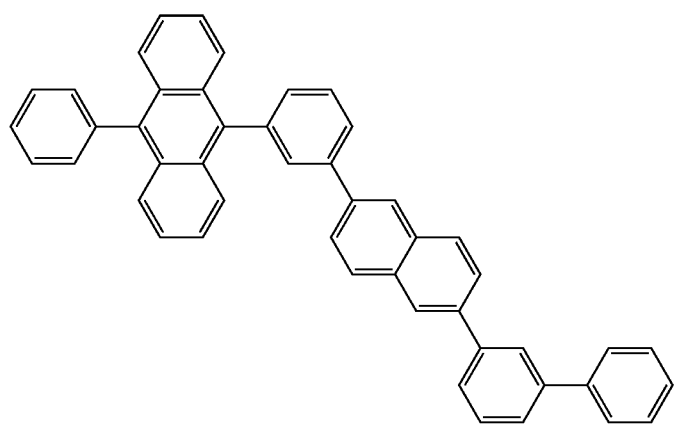
AN-86
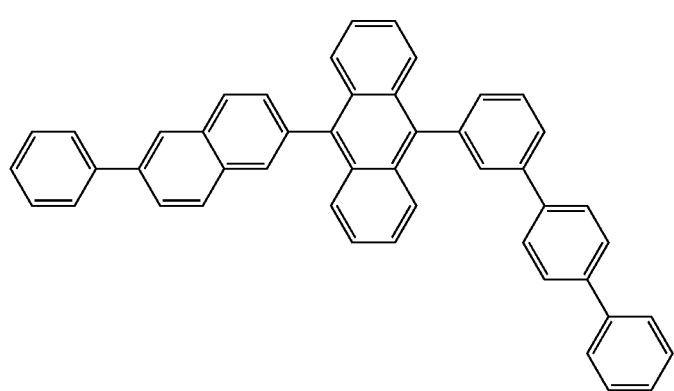
AN-87
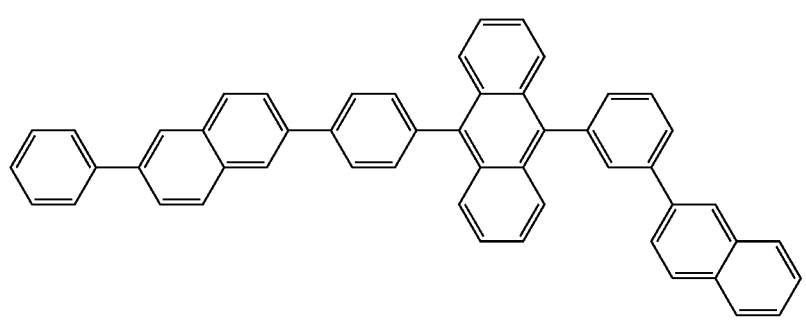
AN-88

-continued
AN-89
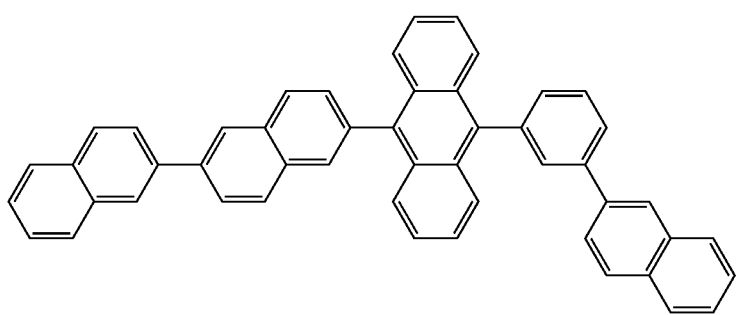
AN-90
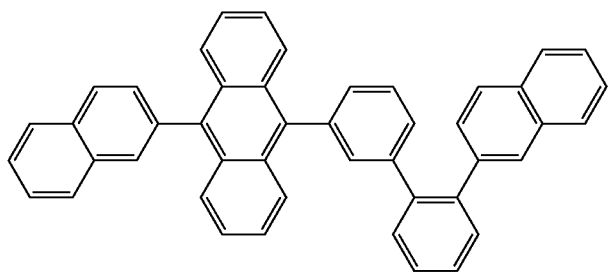
AN-91
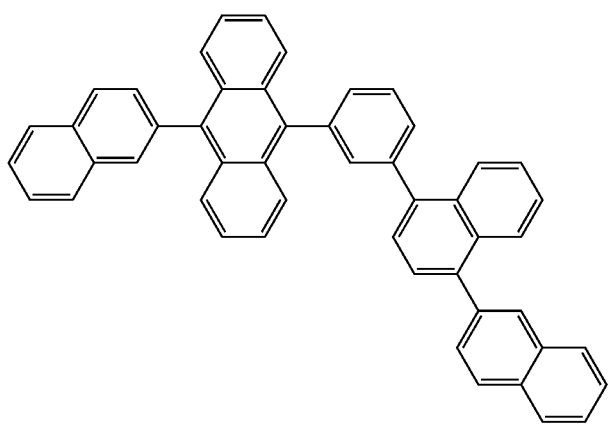
AN-92
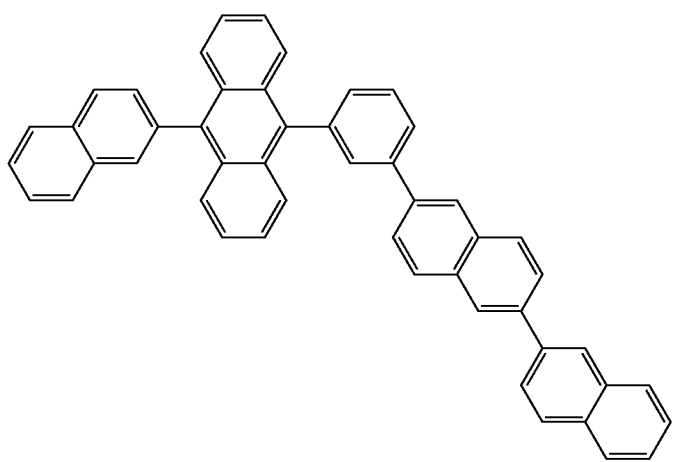

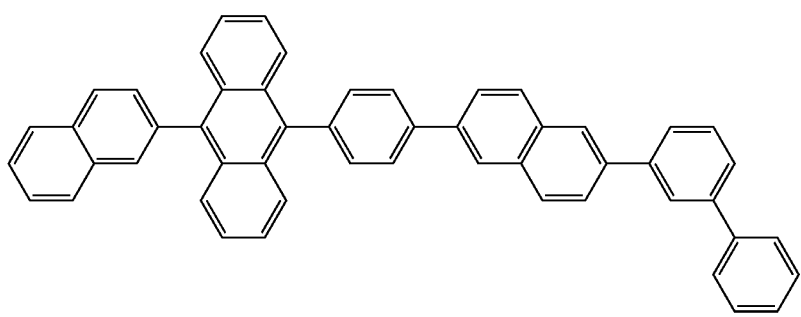
AN-93
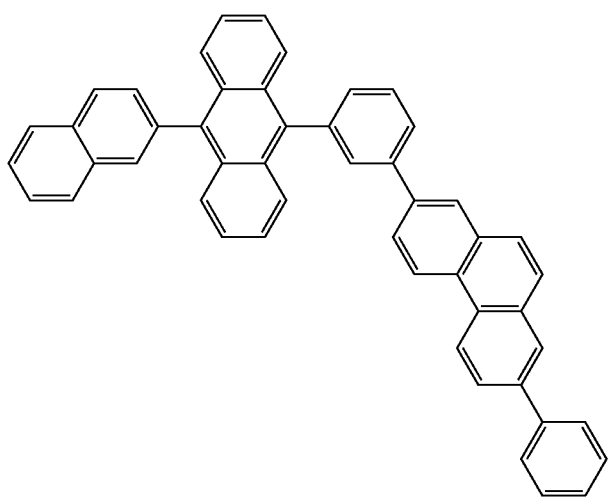
AN-94
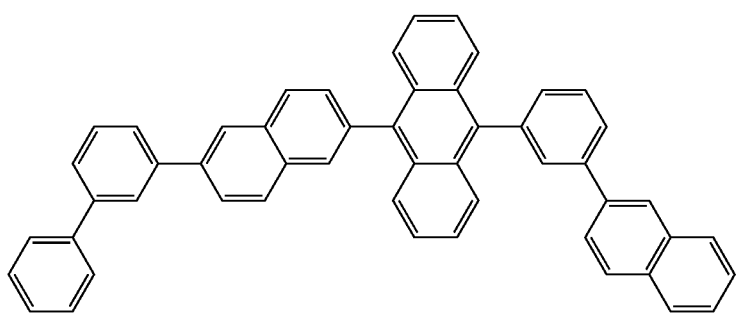
AN-95
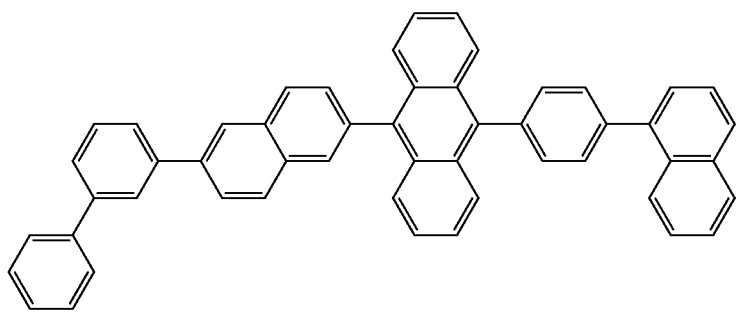
AN-96

-continued
AN-97
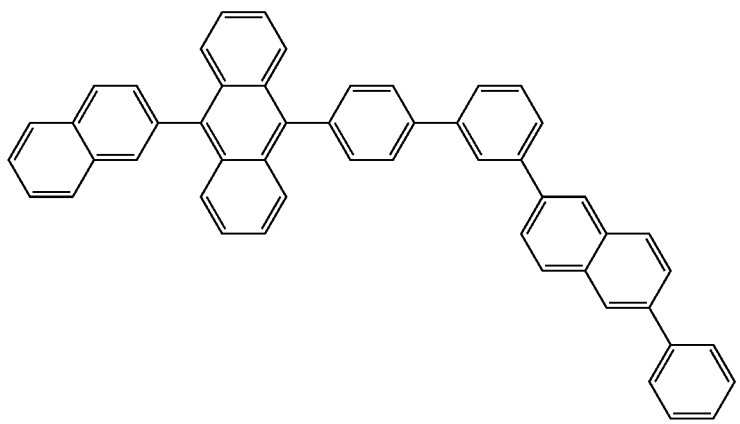
AN-98
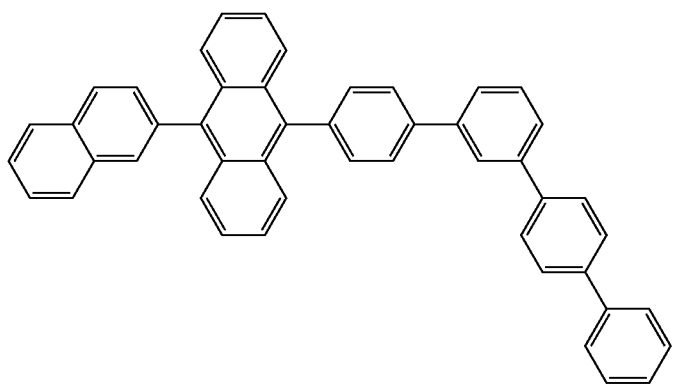
AN-99
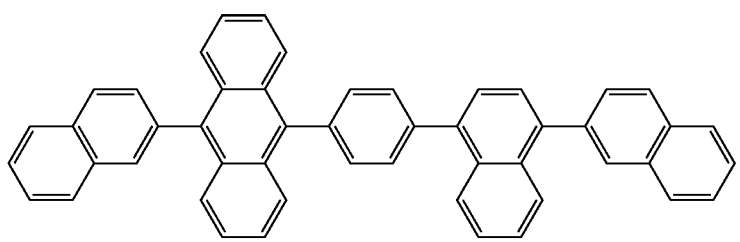
AN-100
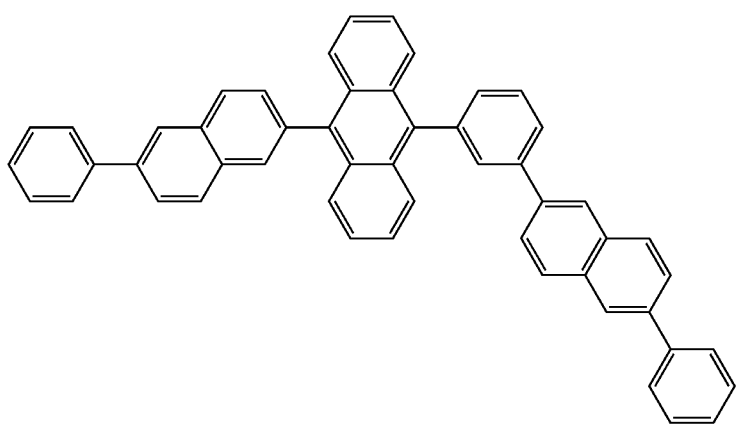

-continued
AN-101
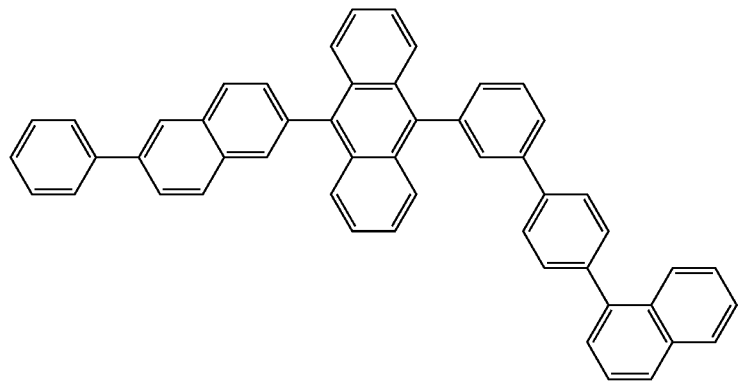
AN-102
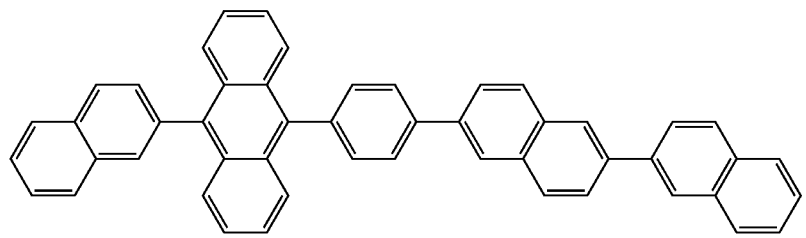
AN-103
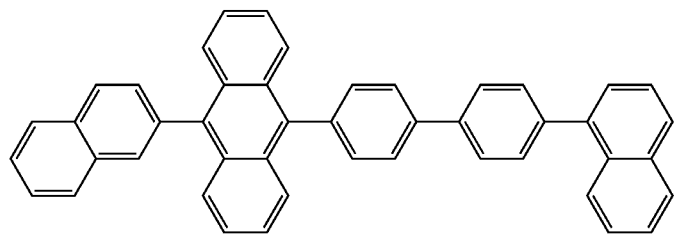
AN-104
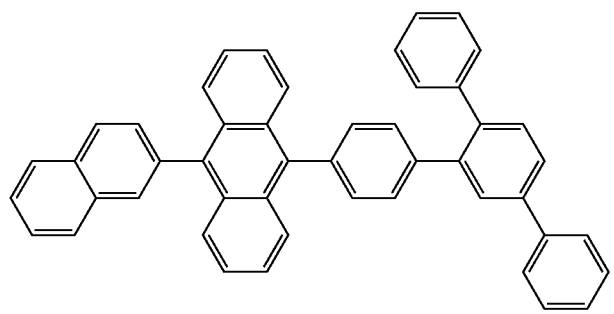
AN-105
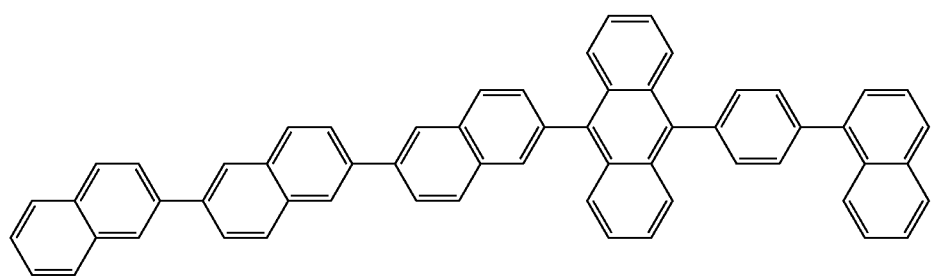

AN-106
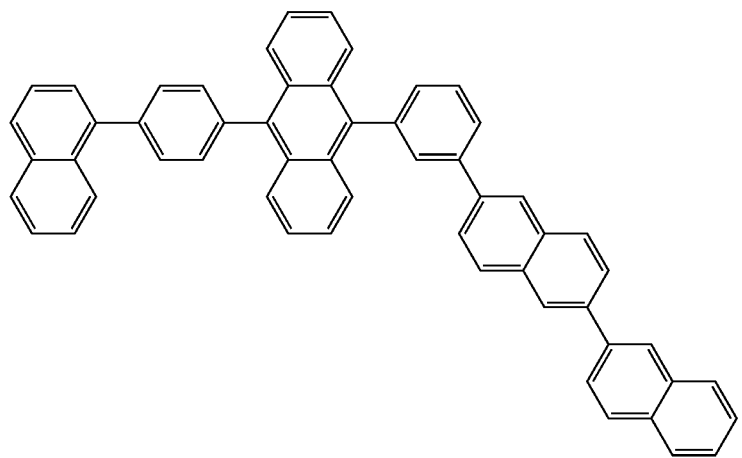
AN-107
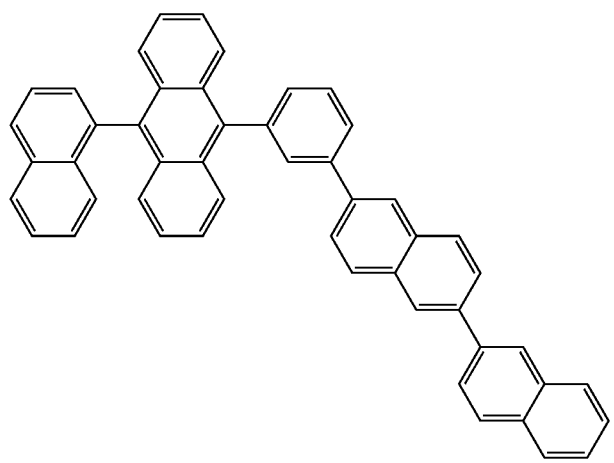
AN-108
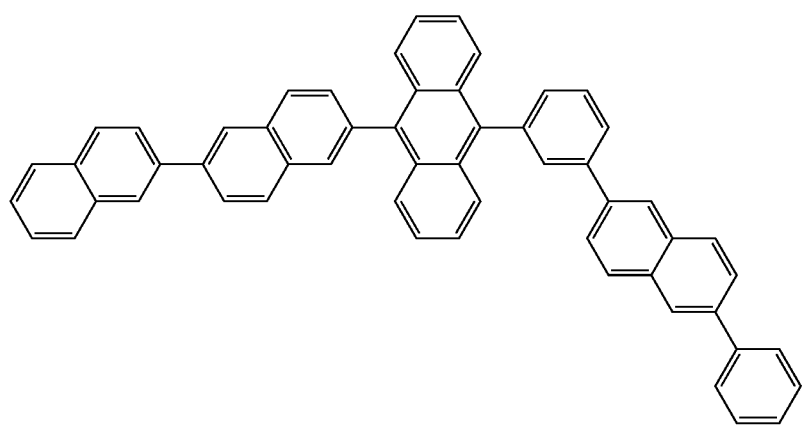

AN-109
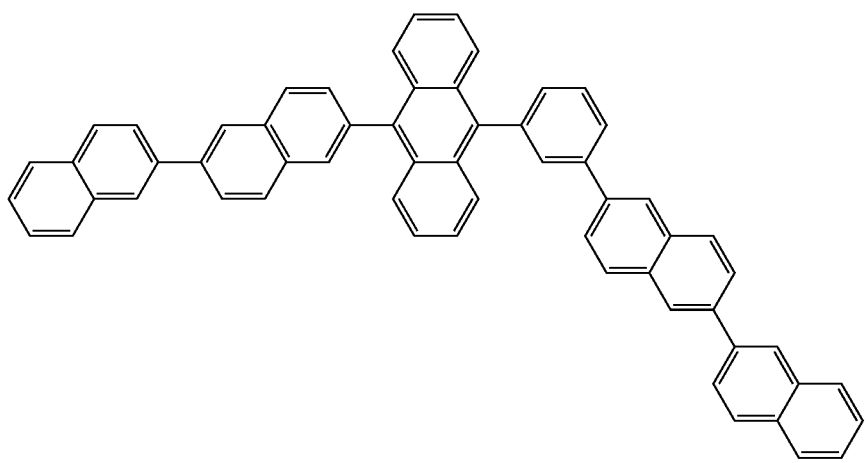
AN-110
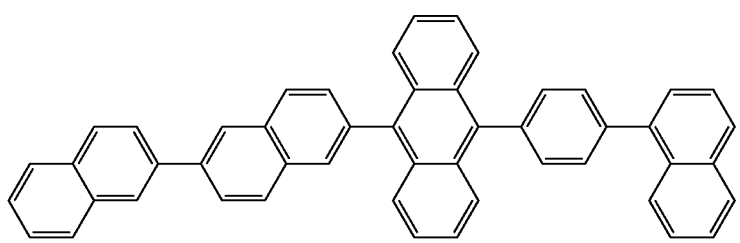
AN-111
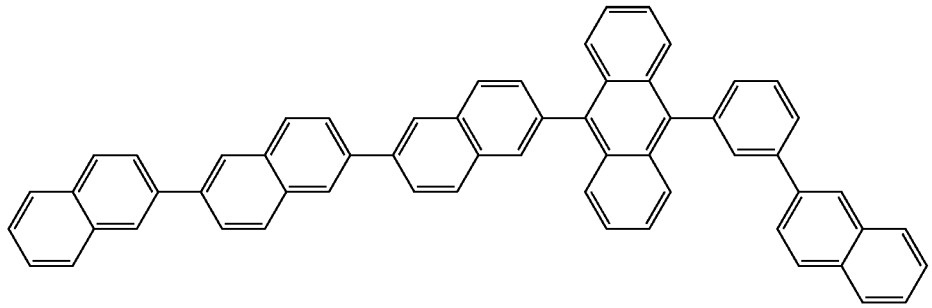
AN-112
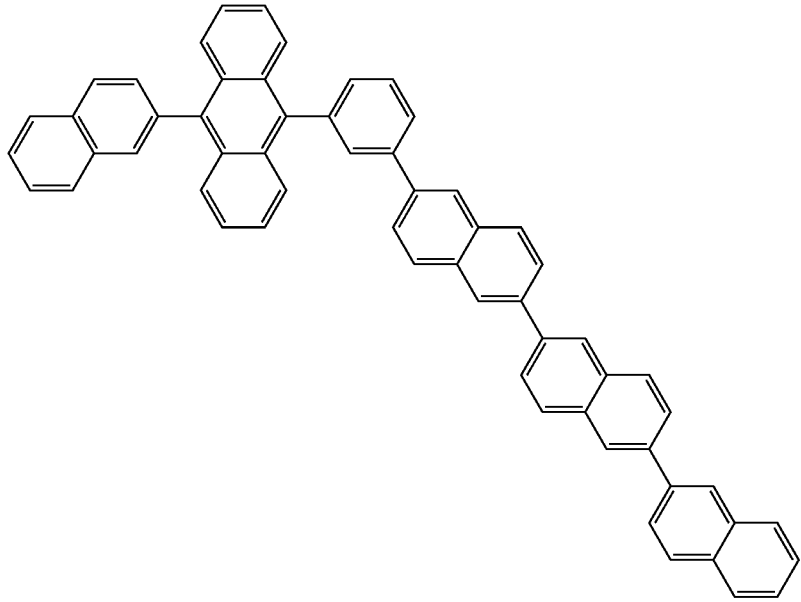

-continued

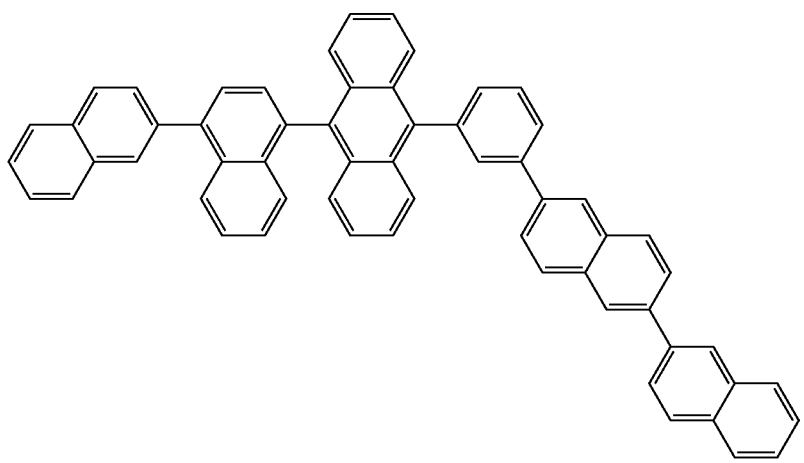

AN-113

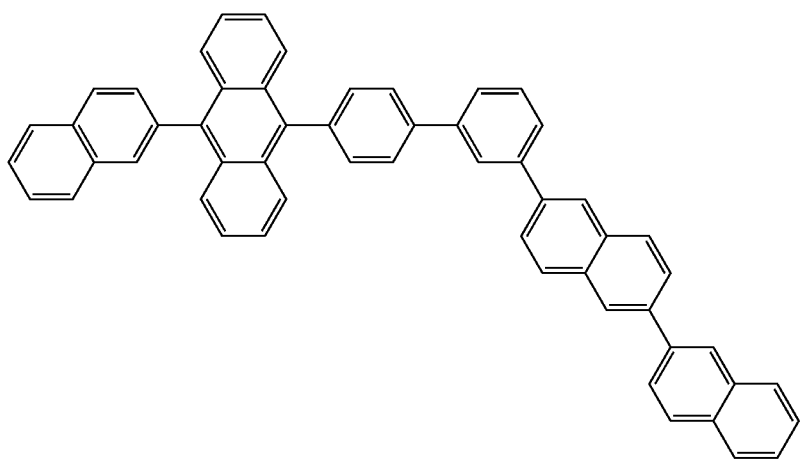

AN-114

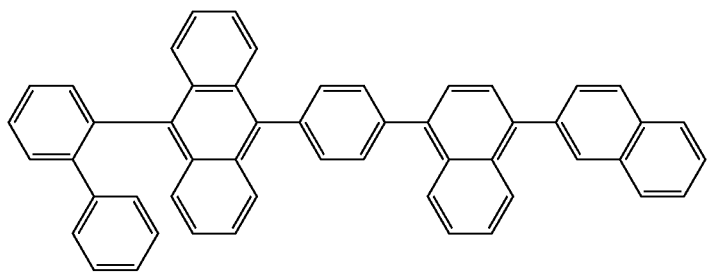

AN-115

The process for producing the anthrylarylene derivatives of the present invention will be described in the following. The anthrylarylene derivatives represented by general formulae (I) to (III) can be produced, for example, in accordance with one of the following schemes of synthesis Schemes 1 to 3.

In the following schemes, $Hal^1$ to $Hal^8$ each represent a halogen atom, R' represents hydrogen atom or a substituted or unsubstituted alkyl group, and adjacent alkyl groups may be bonded to each other.

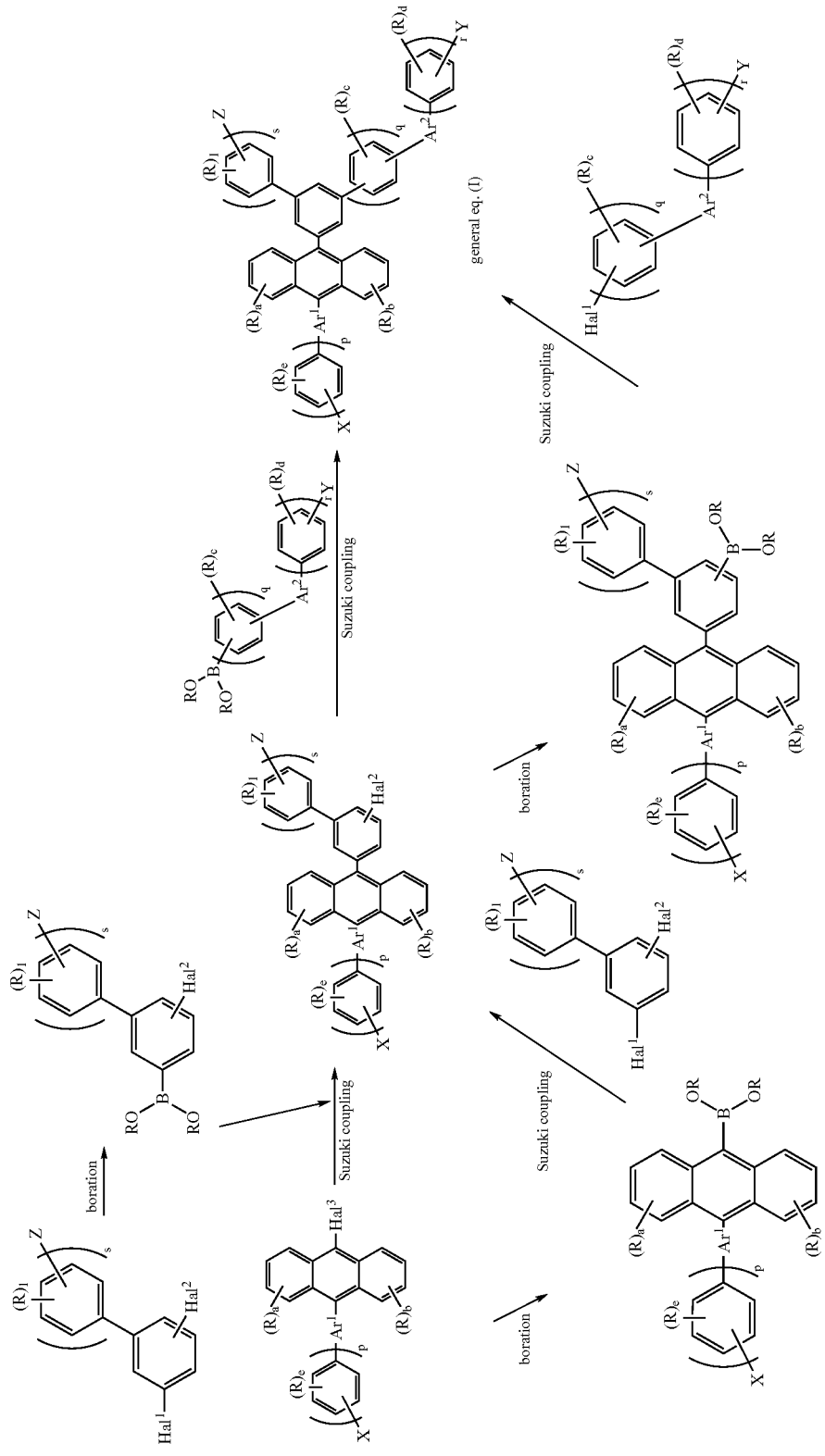
Scheme 1

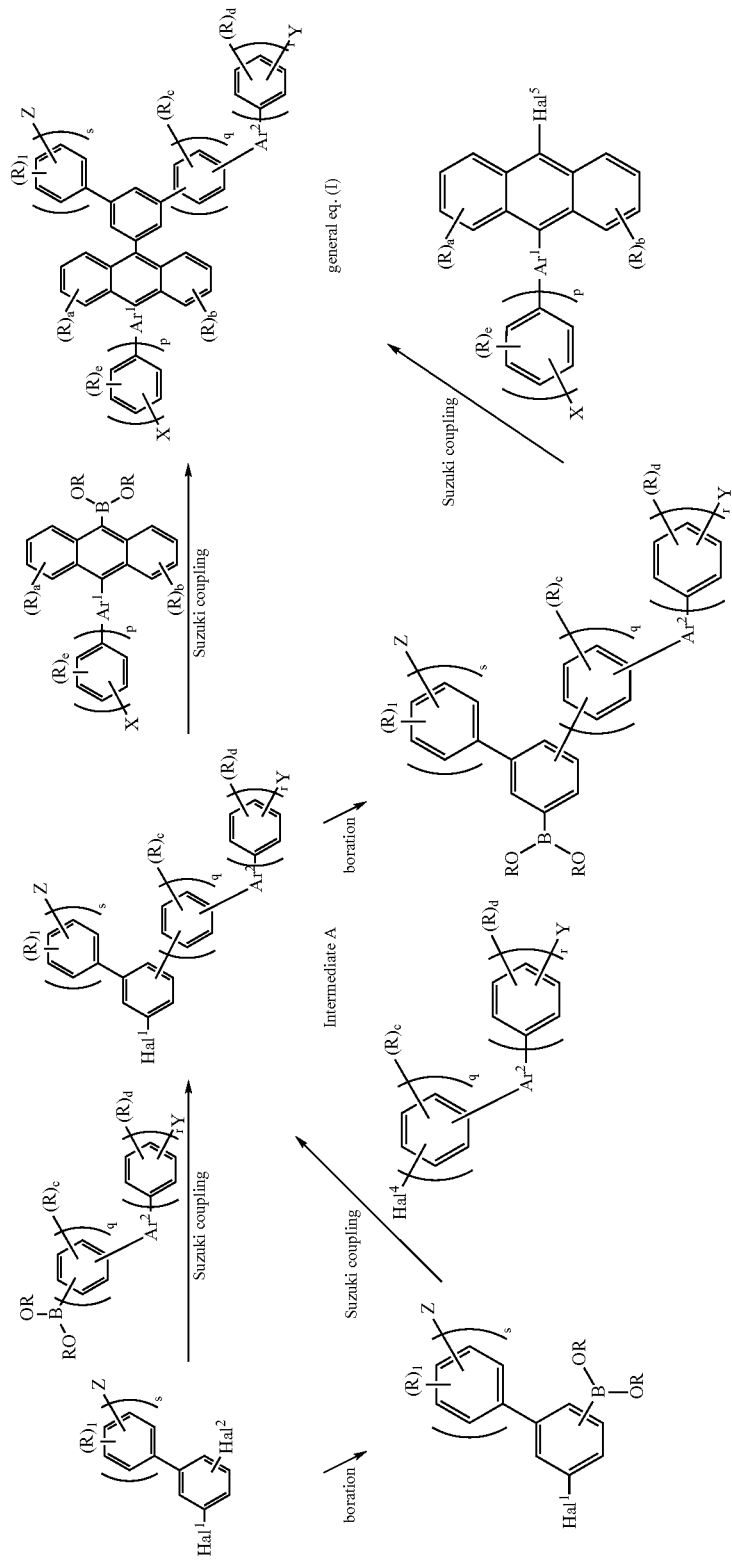

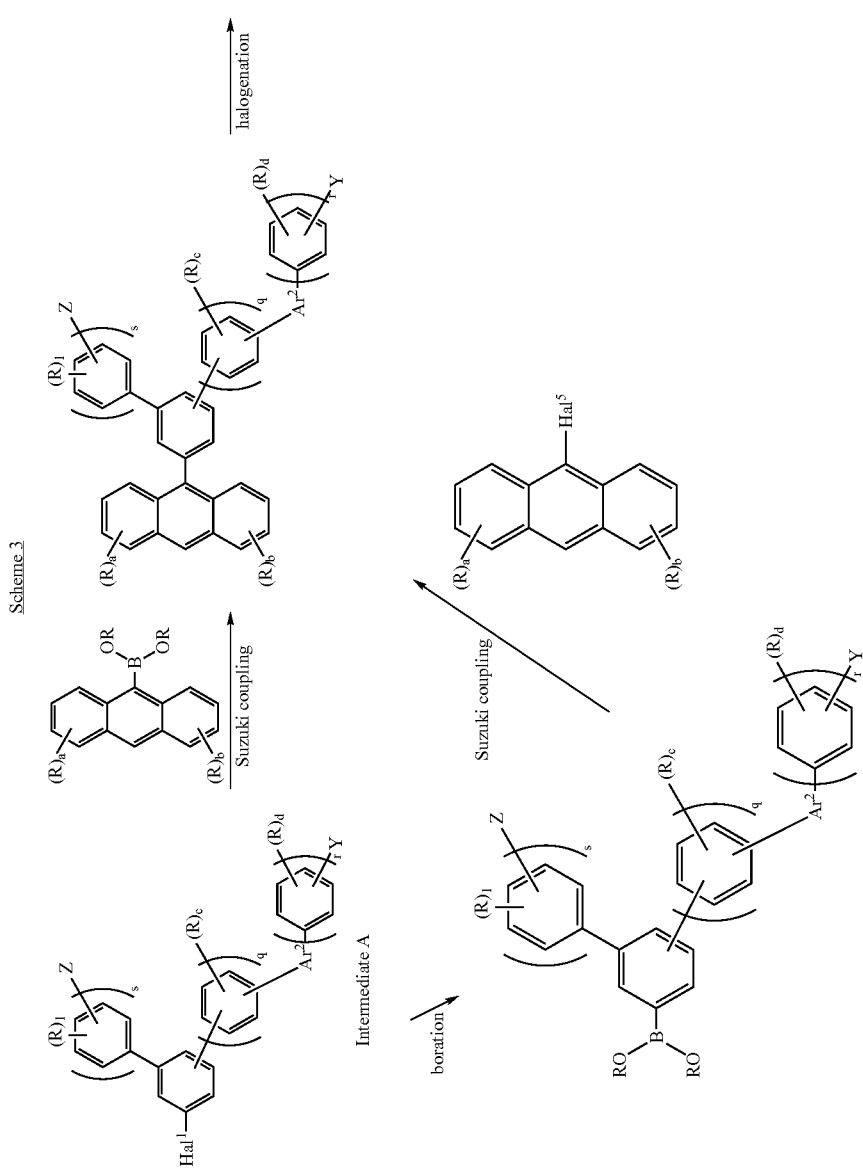

-continued
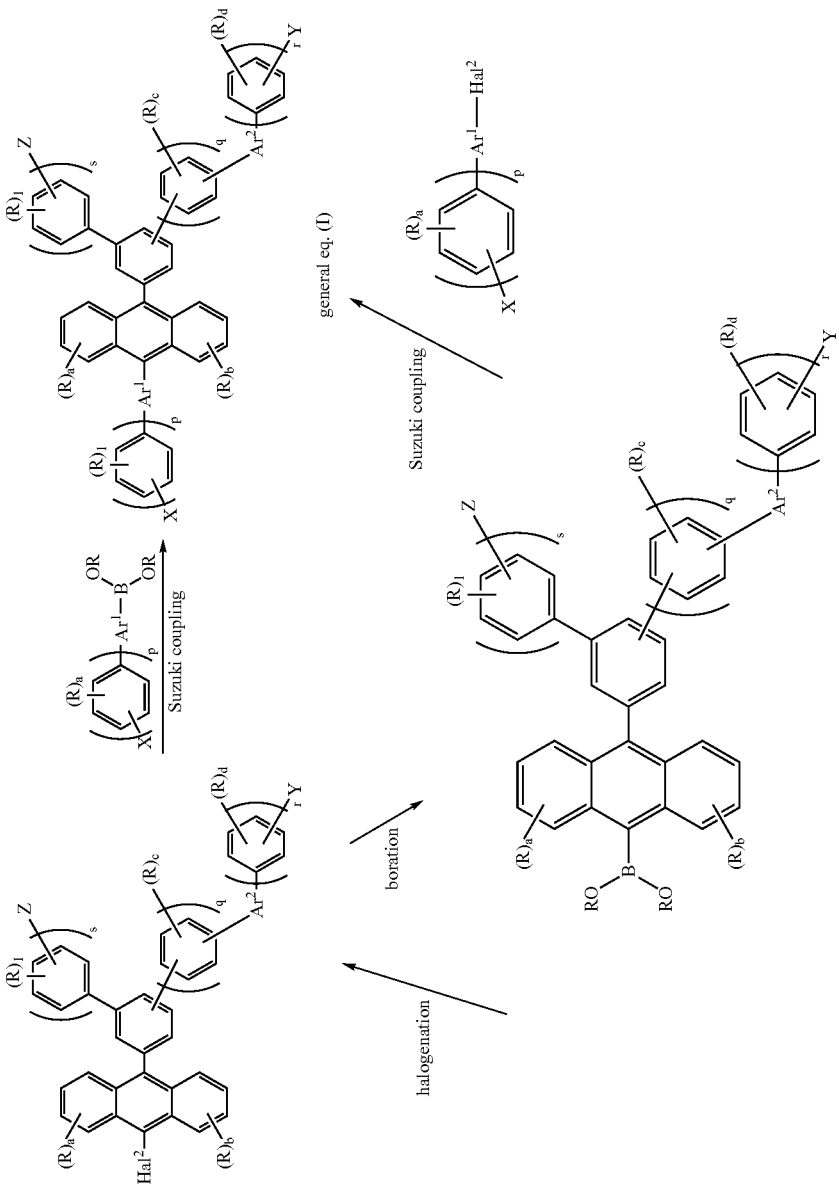

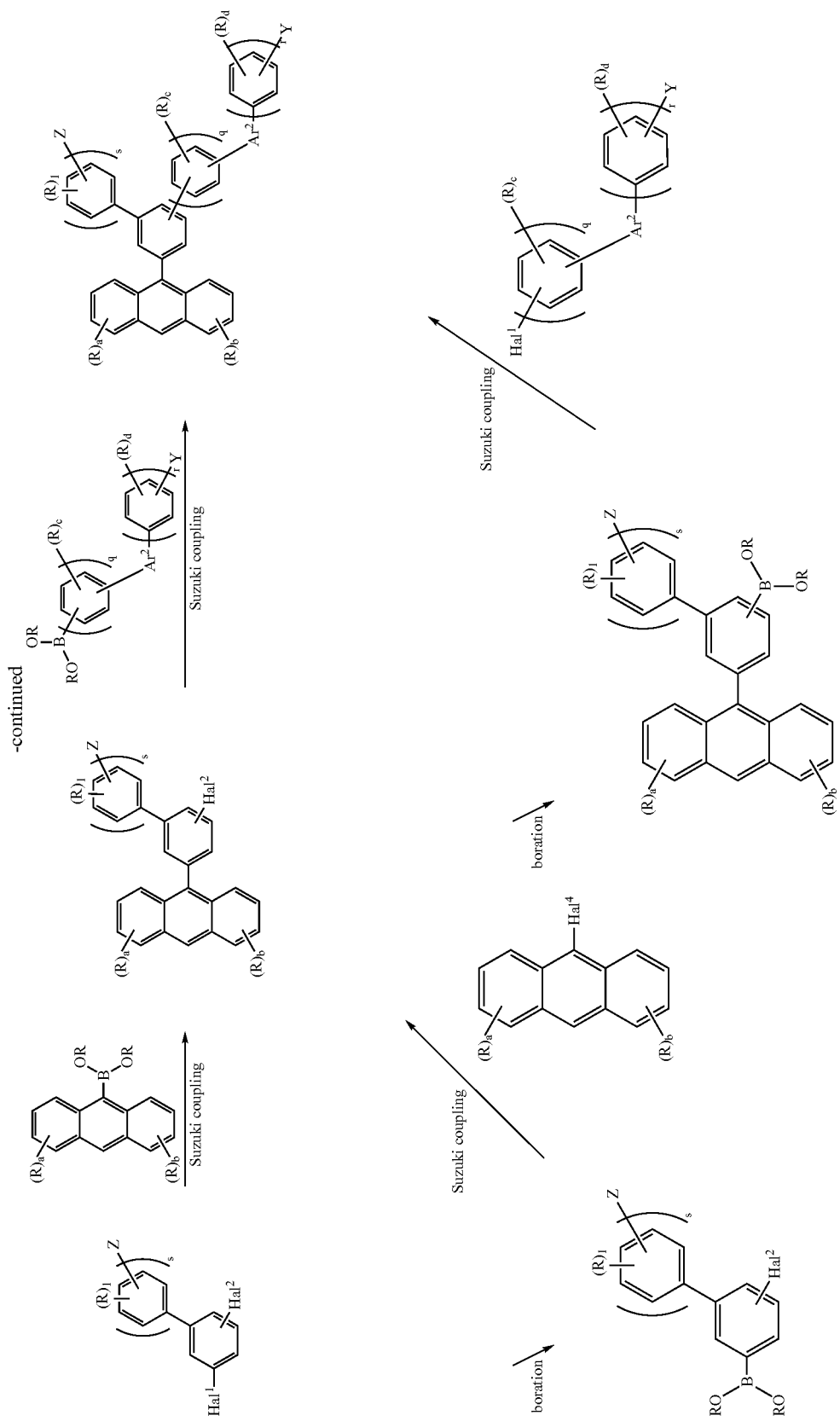

As shown in Schemes 1 to 3, the anthrylarylene compounds represented by general formulae (I) to (III) can be synthesized by conducting the halogenation reaction, the boration reaction and the Suzuki coupling reaction stepwise in a suitable combination.

When an aryl compound halogenated with halogen atoms at two or more positions and a boronic acid derivative are brought into reaction selectively at prescribed positions, while it is possible that the reaction is conducted using an aryl compound halogenated with the same type of the halogen atom alone, it is desirable for the reaction to take place more selectively at the prescribed positions that an aryl compound in which the positions desired for the reaction are substituted with a halogen atom having a greater reactivity than other halogen atoms (the reactivity: I>Br>Cl>F) is used so that the reaction takes place more selectively at the positions desired for the reaction. When a halogenated aryl compound and a halogenated arylboronic acid are brought into reaction, it is preferable that the halogen atom in the halogenated aryl compound has a greater reactivity than that of the halogen atom in the halogenated arylboronic acid.

Many reports are found on the Suzuki coupling reaction (Chem. Rev. Vol. 95, No. 7, 2475 (1995) and others). The reaction can be conducted under the conditions described in these reports.

The reaction is, in general, conducted under an inert atmosphere such as the atmospheres of nitrogen, argon and helium and may be conducted under a pressurized condition, where necessary. The reaction temperature is in the range of 15 to 300° C. and preferably in the range of 30 to 200° C.

As the solvent for the reaction, water, aromatic hydrocarbons such as benzene, toluene and xylene, ethers such as 1,2-dimethoxyethane, diethyl ether, methyl t-butyl ether, tetrahydrofuran and dioxane, saturated hydrocarbons such as pentane, hexane, heptane, octane and cyclohexane, halogenated hydrocarbons such as dichloromethane, chloroform, carbon tetrachloride, 1,2-dichloroethane and 1,1,1-trichloroethane, nitriles such as acetonitrile and benzonitrile, esters such as ethyl acetate, methyl acetate and butyl acetate, and amides such as N,N-dimethylformamide, N,N-dimethylacetamide and N-methylpyrrolidone, can be used singly or as a mixture. Among these solvents, toluene, 1,2-dimethoxyethane, dioxane and water are preferable. The amount by weight of the solvent is in the range of 3 to 50 times as much as and preferably in the range of 4 to 20 times as much as the amount by weight of the arylboronic acid or the derivative thereof.

Examples of the base used in the reaction include sodium carbonate, potassium carbonate, sodium hydroxide, potassium hydroxide, sodium hydrogencarbonate, potassium hydrogencarbonate, magnesium carbonate, lithium carbonate, potassium fluoride, cesium fluoride, cesium chloride, cesium bromide, cesium carbonate, potassium phosphate, methoxysodium, t-butoxypotassium, t-butoxysodium and t-butoxylithium. Among these bases, sodium carbonate is preferable. The amount of the base is in the range of 0.7 to 10 mole equivalents and preferably in the range of 0.9 to 6 mole equivalents based on the amount of the arylboronic acid or the derivative thereof.

Examples of the catalyst used in the reaction include palladium catalysts such as tetrakis(triphenylphosphine)palladium, dichlorobis(triphenylphosphine)palladium, dichloro[bis(diphenylphosphino)ethane]palladium, dichloro[bis(diphenylphosphino)propane]palladium, dichloro[bis(diphenylphosphino)butane]palladium and dichloro[bis(diphenylphosphino)ferrocene]palladium; and nickel catalysts such as tetrakis(triphenylphosphine)nickel, dichlorobis(triphenylphosphine)nickel, dichloro[bis(diphenylphosphino)ethane]nickel, dichloro[bis(diphenylphosphino)propane]nickel, dichloro[bis(diphenylphosphino)butane]nickel and dichloro[bis(diphenylphosphino)ferrocene]nickel. Among these catalysts, tetrakis(triphenylphosphine)palladium is preferable. The amount of the catalyst is in the range of 0.001 to 1 mole equivalent and preferably in the range of 0.01 to 0.1 mole equivalent based on the amount of the halogenated anthracene derivative.

Examples of the halogen atom in the halogen compound include iodine atom, bromine atom, chlorine atom and fluorine atom. Iodine atom and bromine atom are preferable.

The boration reaction can be conducted in accordance with a known process (Jikken Kagaku Koza, $4^{th}$ edition, edited by the Chemical Society of Japan, Volume 24, Pages 61 to 90; J. Org. Chem. Vol. 60, 7508 (1995); and others). For example, when the reaction contains the lithiation reaction or the Grignard reaction of a halogenated aryl compound, in general, the reaction is conducted under an inert atmosphere such as the atmospheres of nitrogen, argon and helium, and an inert solvent is used as the solvent. As the inert solvent, for example, a saturated hydrocarbon such as pentane, hexane, heptane, octane and cyclohexane, an ether such as 1,2-dimethoxyethane, diethyl ether, methyl t-butyl ether, tetrahydrofuran and dioxane, or an aromatic hydrocarbon such as benzene, toluene and xylene, can be used singly or as a mixed solvent. It is preferable that diethyl ether or toluene is used. The amount by weight of the solvent is in the range of 3 to 50 times as much as and preferably in the range of 4 to 20 times as much as the amount by weight of the halogenated aryl compound.

Examples of the lithiating agent include alkali metal reagents such as n-butyllithium, t-butyllithium, phenyllithium and methyllithium; and amide bases such as lithium diisopropylamide and lithium bistrimethylsilylamide. Among these agents, n-butyllithium is preferable. The Grignard reagent can be prepared by the reaction of the halogenated aryl compound and metallic magnesium. As the trialkyl borate, for example, trimethyl borate, triethyl borate, triisopropyl borate and tributyl borate can be used. Trimethyl borate and triisopropyl borate are preferable.

The amounts of the lithiating agent and the metallic magnesium are each in the range of 1 to 10 mole equivalents and preferably in the range of 1 to 2 mole equivalents base on the amount of the halogenated aryl compound. The amount of the trialkyl borate is in the range of 1 to 10 mole equivalents and preferably in the range of 1 to 5 mole equivalents based on the amount of the halogenated aryl compound. The reaction temperature is, in general, in the range of −100 to 50° C. and preferably in the range of −75 to 10° C.

It is preferable that the anthrylarylene derivative of the present invention is used as the light emitting material for organic EL devices and more preferably as the host material for organic EL devices.

The organic electroluminescence device of the present invention comprises a cathode, an anode and an organic thin film layer which comprises one layer or a plurality of layers comprising at least a light emitting layer and is disposed between the cathode and the anode, wherein the organic thin film layer comprises at least one compound selected from anthrylarylene derivatives represented by general formulae (I) to (III) described above singly or as a component of a mixture.

In the organic EL device of the present invention, it is preferable that the light emitting layer further comprises an arylamine compound and/or a styrylamine compound.

As the styrylamine compound, compounds represented by the following general formula (A) are preferable:

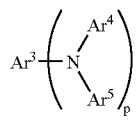
(A)

wherein $Ar^3$ represents a group selected from phenyl group, biphenyl group, terphenyl group, stilbene group and distyrylaryl groups, $Ar^4$ and $Ar^5$ each represent hydrogen atom or an aromatic hydrocarbon group having 6 to 20 carbon atoms, the groups represented by $Ar^3$, $Ar^4$ and $Ar^5$ may be substituted, p represents an integer of 1 to 4 and, preferably, at least one of the groups represented by $Ar^4$ and $Ar^5$ is substituted with styryl group.

Examples of the aromatic hydrocarbon group having 6 to 20 carbon atoms include phenyl group, naphthyl group, anthranyl group, phenanthryl group and terphenyl group.

As the arylamine compound, compounds represented by the following general formula (B) are preferable:

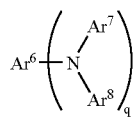
(B)

wherein $Ar^6$ to $Ar^8$ each represent a substituted or unsubstituted aryl group having 5 to 40 nuclear carbon atoms, and q represents an integer of 1 to 4.

Examples of the aryl group having 5 to 40 nuclear carbon atoms include phenyl group, naphthyl group, anthranyl group, phenanthryl group, pyrenyl group, coronyl group, biphenyl group, terphenyl group, pyrrolyl group, furanyl group, thiophenyl group, benzothiophenyl group, oxadiazolyl group, diphenylanthranyl group, indolyl group, carbazolyl group, pyridyl group, benzoquinolyl group, fluoranthenyl group, acenaphthofluoranthenyl group, stilbene group, perylenyl group, chrysenyl group, pycenyl group, triphenylenyl group, rubicenyl group, benzoanthracenyl group, phenylanthranyl group, bisanthracenyl group and aryl groups represented by the following general formula (C) or expressed by the following formula (D). Among these groups, naphthyl group, anthranyl group, chrysenyl group, pyrenyl group and the aryl group expressed by formula (D) are preferable.

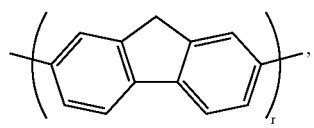
(C)

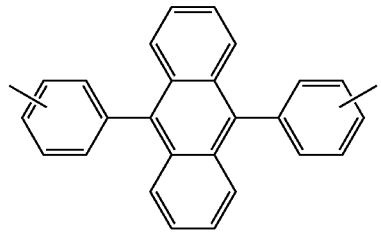
(D)

In general formula (C), r represents an integer of 1 to 3.

Preferable examples of the substituent to the aryl group include alkyl groups having 1 to 6 carbon atoms (ethyl group, methyl group, i-propyl group, n-propyl group, s-butyl group, t-butyl group, pentyl group, hexyl group, cyclopentyl group and cyclohexyl group), alkoxy groups having 1 to 6 carbon atoms (ethoxy group, methoxy group, i-propoxy group, n-propoxy group, s-butoxy group, t-butoxy group, pentoxy group, hexyloxy group, cyclopentoxy group and cyclohexyloxy group), aryl groups having 5 to 40 nuclear carbon atoms, amino groups substituted With an aryl group having 5 to 40 nuclear carbon atoms, ester groups having an aryl group having 5 to 40 nuclear carbon atoms, ester groups having an alkyl group having 1 to 6 carbon atoms, cyano group, nitro group and halogen atoms.

The construction of the organic EL device of the present invention will be described in the following.

Typical examples of the construction of the organic EL device include:

(1) An anode/a light emitting layer/a cathode;
(2) An anode/a hole injecting layer/a light emitting layer/a cathode;
(3) An anode/a light emitting layer/an electron injecting layer/a cathode;
(4) An anode/a hole injecting layer/a light emitting layer/an electron injecting layer/ a cathode;
(5) An anode/an organic semiconductor layer/a light emitting layer/a cathode;
(6) An anode/an organic semiconductor layer/an electron barrier layer/a light emitting layer/a cathode;
(7) An anode/an organic semiconductor layer/a light emitting layer/an adhesion improving layer/a cathode;
(8) An anode/a hole injecting layer/a hole transporting layer/a light emitting layer/an electron injecting layer/a cathode;
(9) An anode/an insulating layer/a light emitting layer/an insulating layer/a cathode;
(10) An anode/an inorganic semiconductor layer/an insulating layer/a light emitting layer/an insulating layer/a cathode;
(11) An anode/an organic semiconductor layer/an insulating layer/a light emitting layer/an insulating layer/a cathode;
(12) An anode/an insulating layer/a hole injecting layer/a hole transporting layer/a light emitting layer/an insulating layer/a cathode; and
(13) An anode/an insulating layer/a hole injecting layer/a hole transporting layer/a light emitting layer/an electron injecting layer/a cathode.

Among the above constructions, construction (8) is preferable. However, the construction of the organic EL device is not limited to those shown above as the examples.

In the organic EL device of the present invention, it is preferable that the light emitting zone or the hole transporting zone comprises the anthrylarylene derivative of the present invention among the constituting elements of the device although any of the organic layers may comprise the anthrylarylene derivative. The content of the anthrylarylene derivative is selected in the range of 30 to 100% by mole.

The organic EL device is, in general, prepared on a substrate transmitting light. The substrate transmitting light is the substrate supporting the organic EL device. It is preferable that the substrate transmitting light has a transmittance of light of 50% or greater in the visible region of 400 to 700 nm. It is also preferable that a flat and smooth substrate is used.

As the substrate transmitting light, for example, glass plates and synthetic resin plates are advantageously used. Examples of the glass plate include plates made of soda lime glass, glass containing barium and strontium, lead glass, aluminosilicate glass, borosilicate glass, barium borosilicate glass and quartz. Examples of the synthetic resin plate include plates made of polycarbonate resins, acrylic resins, polyethylene terephthalate resins, polyether sulfide resins and polysulfone resins.

The anode has the function of injecting holes into the hole transporting layer or the light emitting layer. It is effective that the anode has a work function of 4.5 eV or greater. Examples of the material for the anode used in the present invention include indium tin oxide (ITO), mixtures of indium oxide and zinc oxide (IZO), mixtures of ITO and cerium oxide (ITCO), mixtures of IZO and cerium oxide (IZCO), mixtures of indium oxide and cerium oxide (ICO), mixtures of zinc oxide and aluminum oxide (AZO), tin oxide (NESA), gold, silver, platinum and copper.

The anode can be prepared by forming a thin film of the electrode substance described above in accordance with a process such as the vapor deposition process and the sputtering process.

When the light emitted from the light emitting layer is obtained through the anode, it is preferable that the anode has a transmittance of the emitted light greater than 10%. It is also preferable that the sheet resistivity of the anode is several hundred $\Omega/\square$ or smaller. The thickness of the anode is, in general, selected in the range of 10 nm to 1 µm and preferably in the range of 10 to 200 nm although the thickness may be different depending on the used material.

The light emitting layer in the organic EL device of the present invention has the following functions:
(i) The injecting function: the function of injecting holes from the anode or the hole injecting layer and injecting electrons from the cathode or the electron injecting layer when an electric field is applied;
(ii) The transporting function: the function of transporting injected charges (electrons and holes) by the force of the electric field; and
(iii) The light emitting function: the function of providing the field for recombination of electrons and holes and leading the recombination to the emission of light.

As the process for forming the light emitting layer, a conventional process such as the vapor deposition process, the spin coating process and the LB process can be used. It is particularly preferable that the light emitting layer is a molecular deposit film. The molecular deposit film is a thin film formed by deposition of a material compound in the gas phase or a thin film formed by solidification of a material compound in a solution or in the liquid phase. In general, the molecular deposit film can be distinguished from the thin film formed in accordance with the LB process (the molecular accumulation film) based on the differences in aggregation structures and higher order structures and the functional differences caused by these structural differences.

As disclosed in Japanese Patent Application Laid-Open No. Showa 57(1982)-51781, the light emitting layer can also be formed by dissolving a binder such as a resin and the material compounds into a solvent to prepare a solution, followed by forming a thin film from the prepared solution in accordance with the spin coating process or the like.

In the present invention, where desired, the light emitting layer may comprise conventional light emitting materials other than the light emitting material comprising the anthrylarylene derivative of the present invention, or a light emitting layer comprising other conventional light emitting material may be laminated to the light emitting layer comprising the light emitting material of the present invention as long as the object of the present invention is not adversely affected.

The hole injecting and transporting layer is a layer which helps injection of holes into the light emitting layer and transports the holes to the light emitting region. The layer exhibits a great mobility of holes and, in general, has an ionization energy as small as 5.5 eV or smaller. For the hole injecting and transporting layer, a material which transports holes to the light emitting layer under an electric field of a smaller strength is preferable. A material which exhibits, for example, a mobility of holes of at least $10^{-4}$ cm$^2$/V·sec under application of an electric field of $10^4$ to $10^6$ V/cm is preferable. As the above material, a material can be selected as desired from materials which are conventionally used as the charge transporting material of holes in photoconductive materials and conventional materials which are used for the hole injecting layer in organic EL devices.

Examples include triazole derivatives (U.S. Pat. No. 3,112,197), oxadiazole derivatives (U.S. Pat. No. 3,189,447), imidazole derivatives (Japanese Patent Application Publication No. Showa 37(1962)-16096), polyarylalkane derivatives (U.S. Pat. Nos. 3,615,402, 3,820,989 and 3,542,544; Japanese Patent Application Publication Nos. Showa 45(1970)-555 and Showa 51 (1976)-10983; and Japanese Patent Application Laid-Open Nos. Showa 51(1976)-93224, Showa 55(1980)-17105, Showa 56(1981)-4148, Showa 55(1980)-108667, Showa 55(1980)-156953 and Showa 56(1981)-36656); pyrazoline derivatives and pyrazolone derivatives (U.S. Pat. Nos. 3,180,729 and 4,278,746; and Japanese Patent Application Laid-Open Nos. Showa 55(1980)-88064, Showa 55(1980)-88065, Showa 49(1974)-105537, Showa 55(1980)-51086, Showa 56(1981)-80051, Showa 56(1981)-88141, Showa 57(1982)-45545, Showa 54(1979)-112637 and Showa 55(1980)-74546); phenylenediamine derivatives (U.S. Pat. No. 3,615,404; Japanese Patent Application Publication Nos. Showa 51(1976)-10105, Showa 46(1971)-3712 and Showa 47(1972)-25336; and Japanese Patent Application Laid-Open Nos. Showa 54(1979)-53435, Showa 54(1979)-110536 and Showa 54(1979)-119925); arylamine derivatives (U.S. Pat. Nos. 3,567,450, 3,180,703, 3,240,597, 3,658,520, 4,232,103, 4,175,961 and 4,012,376; Japanese Patent Application Publication Nos. Showa 49(1974)-35702 and Showa 39(1964)-27577; Japanese Patent Application Laid-Open Nos. Showa 55(1980)-144250, Showa 56(1981)-119132 and Showa 56(1981)-22437; and West German Patent No. 1,110,518); chalcone derivatives substituted with amino group (U.S. Pat. No. 3,526,501); oxazole derivatives (U.S. Pat. No. 3,257,203); styrylanthracene derivatives (Japanese Patent Application Laid-Open Nos. Showa 56(1981)-46234); fluorenone derivatives (Japanese Patent Application Laid-Open Nos. Showa 54(1979)-110837); hydrazone derivatives (U.S. Pat. No. 3,717,462; and Japanese Patent Application Laid-Open Nos. Showa 54(1979)-59143, Showa 55(1980)-52063, Showa 55(1980)-52064, Showa 55(1980)-46760, Showa 55(1980)-85495, Showa 57(1982)-11350, Showa 57(1982)-148749 and Heisei 2(1990)-31159$_1$); stilbene derivatives (Japanese Patent Application Laid-Open Nos. Showa 61(1986)-210363, Showa 61(1986)-228451, Showa 61(1986)-14642, Showa 61(1986)-72255, Showa 62(1987)-47646, Showa 62(1987)-36674, Showa 62(1987)-10652, Showa 62(1987)-30255, Showa 60(1985)-93455, Showa 60(1985)-94462, Showa 60(1985)-174749 and Showa 60(1985)-175052); silazane derivatives (U.S. Pat. No. 4,950, 950); polysilane-based compounds (Japanese Patent Application Laid-Open No. Heisei 2(1990)-204996); aniline-based copolymers (Japanese Patent Application Laid-Open No. Heisei 2(1990)-282263); and electrically conductive macromolecular oligomers (in particular, thiophene oligomers) disclosed in Japanese Patent Application Laid-Open No. Heisei 1(1989)-211399.

Besides the above materials which can be used as the material for the hole injecting layer, porphyrin compounds (compounds disclosed in Japanese Patent Application Laid-Open No. Showa 63(1988)-2956965); and aromatic tertiary amine compounds and styrylamine compounds (U.S. Pat. No. 4,127,412 and Japanese Patent Application Laid-Open Nos. Showa 53(1978)-27033, Showa 54(1979)-58445, Showa 54(1979)-149634, Showa 54(1979)-64299, Showa 55(1980)-79450. Showa 55(1980)-144250, Showa 56(1981)-119132, Showa 61(1986)-295558, Showa 61(1986)-98353 and Showa 63(1988)-295695) are preferable, and the aromatic tertiary amines are more preferable.

Further examples include compounds having two condensed aromatic rings in the molecule which are described in the U.S. Pat. No. 5,061,569 such as 4,4'-bis(N-(1-naphthyl)-N-phenylamino)biphenyl (referred to as NPD, hereinafter) and a compound in which three triphenylamine units are bonded together in a star-burst shape, which is described in Japanese Patent Application Laid-Open No. Heisei 4(1992)-308688, such as 4,4',4"-tris(N-(3-methylphenyl)-N-phenylamino)triphenylamine (referred to as MTDATA, hereinafter).

Inorganic compounds such as Si of the p-type and SiC of the p-type can also be used as the material for the hole injecting layer.

The hole injecting and transporting layer can be formed by preparing a thin film of the above compound in accordance with a conventional process, such as the vacuum vapor deposition process, the spin coating process, the casting process and the LB process. The thickness of the hole injecting and transporting layer is not particularly limited. In general, the thickness is 5 nm to 5 μm.

The organic semiconductor layer is a layer helping injection of holes or electrons into the light emitting layer. As the organic semiconductor layer, a layer having a conductivity of $10^{-10}$ S/cm or greater is preferable. As the material for the organic semiconductor layer, oligomers containing thiophene can be used, and conductive oligomers such as oligomers containing arylamine and conductive dendrimers such as dendrimers containing arylamine, which are disclosed in Japanese Patent Application Laid-Open No. Heisei 8(1996)-193191, can also be used.

The electron injecting and transporting layer is a layer which helps injection of electrons into the light emitting layer and transportation of the electrons to the light emitting region and exhibits a great mobility of electrons. The adhesion improving layer is an electron injecting layer comprising a material exhibiting improved adhesion with the cathode.

It is known that, in an organic EL device, emitted light is reflected at an electrode (the cathode in the present case), and the light emitted and obtained directly from the anode and the light obtained after reflection at the electrode interfere with each other. The thickness of the electron transporting layer is suitably selected in the range of several nm to several μm so that the interference is effectively utilized. When the thickness is great, it is preferable that the mobility of electrons is at least $10^{-5}$ cm$^2$/Vs or greater under the application of an electric field of $10^4$ to $10^6$ V/cm so that the increase in the voltage is prevented.

As the material used for the electron injecting layer, metal complexes of 8-hydroxyquinoline and derivatives thereof and oxadiazole derivatives are preferable. Examples of 8-hydroxyquinoline and the derivative thereof include metal chelated oxinoid compounds including chelate compounds of oxines (in general, 8-quinolinol or 8-hydroxyquinoline). For example, tris(8-quinolinol)aluminum (Alq) can be used as the electron injecting material.

Examples of the oxadiazole derivative include electron transfer compounds represented by the following general formulae:

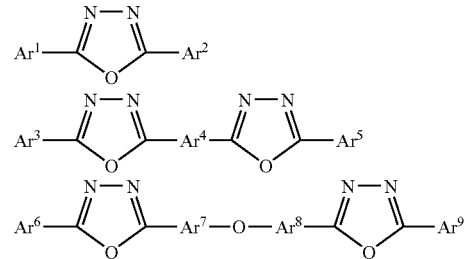

In the above formulae, $Ar^1$, $Ar^2$, $Ar^3$, $Ar^5$, $Ar^6$ and $Ar^9$ each represent a substituted or unsubstituted aryl group and may represent the same group or different groups. $Ar^4$, $Ar^7$ and $Ar^8$ each represent a substituted or unsubstituted arylene group and may represent the same group or different groups.

Examples of the aryl group include phenyl group, biphenyl group, anthranyl group, perylenyl group and pyrenyl group. Examples of the arylene group include phenylene group, naphthylene group, biphenylene group, anthranylene group, perylenylene group and pyrenylene group. Examples of the substituent include alkyl groups having 1 to 10 carbon atoms, alkoxy groups having 1 to 10 carbon atoms and cyano group. As the electron transfer compound, compounds which can form thin films are preferable.

Specific examples of the electron transfer compound include the following compounds:

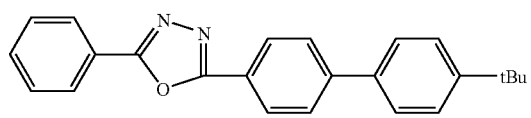

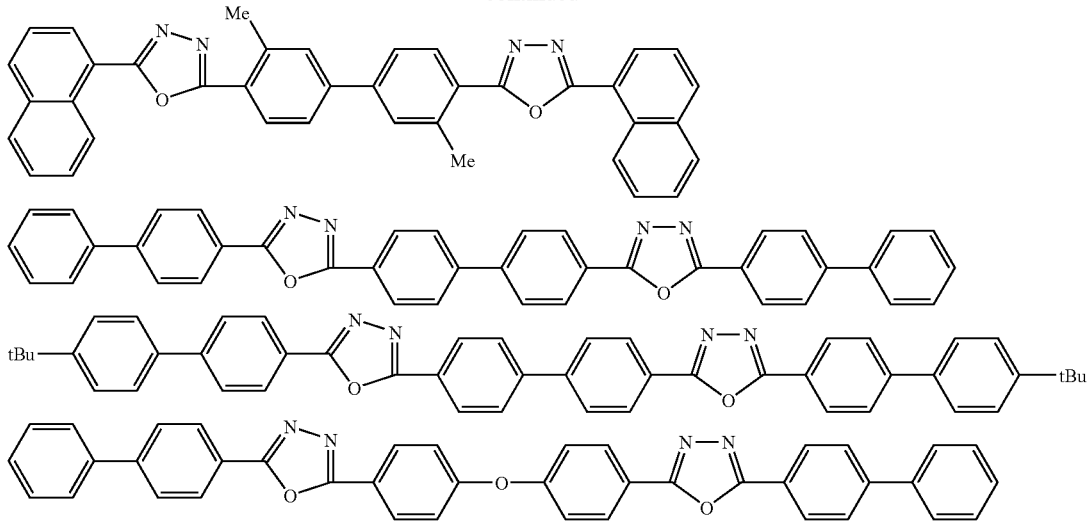

As the material which can be used for the electron injecting layer and the electron transporting layer, compounds represented by the following general formulae (E) to (J) can be used.

Heterocyclic derivatives having nitrogen atom represented by any one of general formulae (E) and (F):

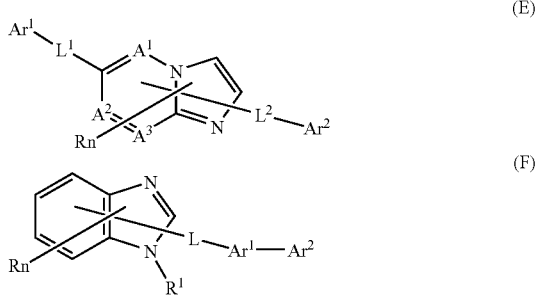

In general formulae (E) and (F), $A^1$ to $A^3$ each independently represent nitrogen atom or carbon atom.

$Ar^1$ represents a substituted or unsubstituted aryl group having 6 to 60 nuclear carbon atoms or a substituted or unsubstituted heteroaryl group having 3 to 60 nuclear carbon atoms; $Ar^2$ represents hydrogen atom, a substituted or unsubstituted aryl group having 6 to 60 nuclear carbon atoms, a substituted or unsubstituted heteroaryl group having 3 to 60 nuclear carbon atoms, a substituted or unsubstituted alkyl group having 1 to 20 carbon atoms, a substituted or unsubstituted alkoxy group having 1 to 20 carbon atoms or a divalent group derived from any of the above groups; and either one of $Ar^1$ and $Ar^2$ represents a substituted or unsubstituted condensed ring group having 10 to 60 nuclear carbon atoms or a substituted or unsubstituted monohetero condensed ring group having 3 to 60 nuclear carbon atoms.

$L^1$, $L^2$ and L each independently represent the single bond, a substituted or unsubstituted arylene group having 6 to 60 nuclear carbon atoms, a substituted or unsubstituted heteroarylene group having 3 to 60 nuclear carbon atoms or a substituted or unsubstituted fluorenylene group.

R represents hydrogen atom, a substituted or unsubstituted aryl group having 6 to 60 nuclear carbon atoms, a substituted or unsubstituted heteroaryl group having 3 to 60 nuclear carbon atoms, a substituted or unsubstituted alkyl group having 1 to 20 carbon atoms or a substituted or unsubstituted alkoxy group having 1 to 20 carbon atoms; n represents an integer of 0 to 5; and, when n represents an integer of 2 or greater, the atoms and the groups represented by a plurality of R may be the same with or different from each other, and a plurality of groups represented by R which are adjacent to each other may be bonded to each other to form an aliphatic ring of the carbon ring type or an aromatic ring of the carbon ring type.

Heterocyclic compounds having nitrogen atom represented by the following general formula (G):

$$HAr\text{-}L\text{-}Ar^1\text{—}Ar^2 \quad (G)$$

In general formula (G), HAr represents a heterocyclic group having 3 to 40 carbon atoms and nitrogen atom which may have substituents, L represents the single bond or an arylene group having 6 to 60 carbon atoms which may have substituents, a heteroarylene group having 3 to 60 carbon atoms which may have substituents or a fluorenylene group which may have substituents, $Ar^1$ represents a divalent aromatic hydrocarbon group having 6 to 60 carbon atoms which may have substituents, and $Ar^2$ represents an aryl group having 6 to 60 carbon atoms which may have substituents or a heteroaryl group having 3 to 60 carbon atoms which may have substituents.

Silacyclopentadiene derivatives represented by the following general formula (H):

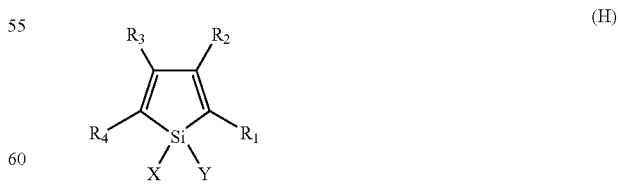

In general formula (H), X and Y each independently represent a saturated or unsaturated hydrocarbon group having 1 to 6 carbon atoms, an alkoxy group, an alkenyloxy group, an alkynyloxy group, hydroxy group, a substituted or unsubstituted aryl group, a substituted or unsubstituted heterocyclic group or a saturated or unsaturated cyclic group formed by bonding of the above groups represented by X and Y; and $R_1$ to $R_4$ each independently represent hydrogen atom, a halogen atom, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxyl group, an arylcarbonyloxyl group, an alkoxycarbonyloxy group, an aryloxycarbonyloxy group, sulfinyl group, sulfonyl group, sulfanyl group, silyl group, carbamoyl group, an aryl group, a heterocyclic group, an alkenyl group, an alkynyl group, nitro group, formyl group, nitroso group, formyloxy group, isocyano group, cyanate group, isocyanate group, thiocyanate group, isothiocyanate group, a cyano group or, when the groups are adjacent to each other, a structure formed by condensation of substituted or unsubstituted rings.

Borane derivatives represented by the following general formula (I):

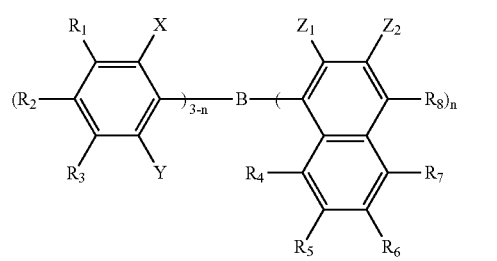

(I)

In general formula (I), $R_1$ to $R_8$ and $Z_2$ each independently represent hydrogen atom, a saturated or unsaturated hydrocarbon group, an aromatic hydrocarbon group, a heterocyclic group, a substituted amino group, a substituted boryl group, an alkoxy group or an aryloxy group; X, Y and $Z_1$ each independently represent a saturated or unsaturated hydrocarbon group, an aromatic hydrocarbon group, a heterocyclic group, a substituted amino group, an alkoxy group or an aryloxy group, and substituents represented by $Z_1$ and $Z_2$ may be bonded to each other to form a condensed ring; n represents an integer of 1 to 3 and, when n represents an integer of 2 or greater, a plurality of $Z_1$ may represent different groups; and the case where n represents 1, X, Y and $R_2$ each represent methyl group and $R_8$ represents hydrogen atom or a substituted boryl group and the case where n represents 3 and $Z_1$ represents methyl group are excluded.

Compounds represented by general formula (J):

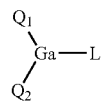

(J)

In general formula (J), $Q^1$ and $Q^2$ each independently represent a ligand represented by the following general formula (K):

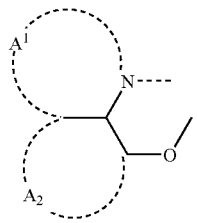

(K)

(rings $A^1$ and $A^2$ each representing six-membered aryl cyclic structure which may have substituents and are condensed with each other), L represents a halogen atom, a substituted or unsubstituted alkyl group, a substituted or unsubstituted cycloalkyl group, a substituted or unsubstituted aryl group, a substituted or unsubstituted heterocyclic group, —$OR^1$ ($R^1$ representing hydrogen atom, a substituted or unsubstituted alkyl group, a substituted or unsubstituted cycloalkyl group, a substituted or unsubstituted aryl group or a substituted or unsubstituted heterocyclic group) or —O—Ga-$Q^3(Q^4)$ ($Q^3$ and $Q^4$ are as defined for $Q^1$ and $Q^2$).

The above metal complex compound strongly exhibits the property as the n-type semiconductor and a great ability of electron injection. Since the energy of formation of the complex compound is small, the bonding between the metal and the ligand in the formed metal complex compound is strong, and the quantum efficiency of fluorescence as the light emitting material is great.

Examples of the substituent to rings $A^1$ and $A^2$ forming the ligand represented by general formula (K) include halogen atoms such as chlorine atom, bromine atom, iodine atom and fluorine atom; substituted and unsubstituted alkyl groups such as methyl group, ethyl group, propyl group, butyl group, s-butyl group, t-butyl group, pentyl group, hexyl group, heptyl group, octyl group, stearyl group and trichloromethyl group; substituted and unsubstituted aryl groups such as phenyl group, naphthyl group, 3-methylphenyl group, 3-methoxyphenyl group, 3-fluorophenyl group, 3-trichloromethylphenyl group, 3-trifluoromethylphenyl group and 3-nitrophenyl group; substituted and unsubstituted alkoxy groups such as methoxy group, n-butoxy group, t-butoxy group, trichlorometheoxy group, trifluoroethoxy group, pentafluoropropoxy group, 2,2,3,3-tetrafluoropropoxy group, 1,1,1,3,3,3-hexafluoro-2-propoxy group and 6-(perfluoroethyl)hexyloxy group; substituted and unsubstituted aryloxy groups such as phenoxy group, p-nitrophenoxy group, p-t-butylphenoxy group, 3-fluorophenoxy group, pentafluorophenoxy group and 3-triflurormethylphenoxy group; substituted and unsubstituted alkylthio groups such as methylthio group, ethylthio group, t-butylthio group, hexylthio group, octylthio group and trifluoromethylthio group; substituted and unsubstituted arylthio groups such as phenylthio group, p-nitrophenylthio group, p-t-butylphenylthio group, 3-fluorophenylthio group, pentafluorophenylthio group and 3-trifluoromethylphenylthio group; cyano group; nitro group; amino group; mono- and disubstituted amino groups such as methylamino group, diethylamino group, ethylamino group, diethylamino group, dipropylamino group, dibutylamiono group and diphenylamino group; acylamino groups such as bis(acetoxymethyl)amino group, bis(acetoxyethyl)amino group, bis(acetoxypropyl)amino group and bis(acetoxybutyl)amino group; hydroxy group; siloxy group; acyl group; carbamoyl groups such as methylcarbamoyl group, dimethylcarbamoyl group, ethylcarbamoyl group, diethylcarbamoyl group, propylcarbamoyl group, butylcarbamoyl group and phenylcarbamoyl group; carboxylic acid group; sulfonic acid group; imide group; cycloalkyl groups such as cyclopentane group and cyclohexyl group; aryl groups such as phenyl group, naphthyl group, biphenyl group, anthranyl group, phenanthryl group, fluorenyl group and pyrenyl group; and heterocyclic groups such as pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, triatinyl group, carbazolyl group, furanyl group, thiophenyl group, oxazolyl group, oxadiazolyl group, benzoxazolyl group, thiazolyl group, thiadiazolyl group, benzothiazolyl group, triazolyl group, imidazolyl group, benzimidazolyl group and planyl group. The above substituents may be bonded to each other to form a six-membered aryl group or heterocyclic group.

A device comprising a reducing dopant in the interfacial region between the region transporting electrons or the cathode and the organic layer is preferable as an embodiment of the organic EL device of the present invention. The reducing dopant is defined as a substance which can reduce a compound having the electron transporting property. Various compounds can be used as the reducing dopant as long as the compounds have the specific reductive property. For example, at least one substance selected from the group consisting of alkali metals, alkaline earth metals, rare earth metals, oxides of alkali metals, halides of alkali metals, oxides of alkaline earth metals, halides of alkaline earth metals, oxides of rare earth metals, halides of rare earth metals, carbonates of alkali metals, carbonates of alkaline earth metals, organic complexes of alkali metals, organic complexes of alkaline earth metals and organic complexes of rare earth metals can be advantageously used.

Preferable examples of the reducing dopant include substances having a work function of 2.9 eV or smaller, specific examples of which include at least one alkali metal selected from the group consisting of Na (the work function: 2.36 eV), K (the work function: 2.28 eV), Rb (the work function: 2.16 eV) and Cs (the work function: 1.95 eV) and at least one alkaline earth metal selected from the group consisting of Ca (the work function: 2.9 eV), Sr (the work function: 2.0 to 2.5 eV) and Ba (the work function: 2.52 eV). Among the above substances, at least one alkali metal selected from the group consisting of K, Rb and Cs is more preferable, Rb and Cs are still more preferable, and Cs is most preferable as the reducing dopant. These alkali metals have great reducing ability, and the luminance of the emitted light and the life of the organic EL device can be increased by addition of a relatively small amount of the alkali metal into the electron injecting zone. As the reducing dopant having a work function of 2.9 eV or smaller, combinations of two or more alkali metals are also preferable. Combinations having Cs such as the combinations of Cs and Na, Cs and K, Cs and Rb and Cs, Na and K are more preferable. The reducing ability can be efficiently exhibited by the combination having Cs. The luminance of emitted light and the life of the organic EL device can be increased by adding the combination having Cs into the electron injecting zone.

In the present invention, an electron injecting layer which is constituted with an insulating material or a semiconductor may further be disposed between the cathode and the organic layer. By the electron injecting layer, leak of electric current can be effectively prevented, and the electron injecting property can be improved. As the insulating material, at least one metal compound selected from the group consisting of alkali metal chalcogenides, alkaline earth metal chalcogenides, halides of alkali metals and halides of alkaline earth metals is preferable. It is preferable that the electron injecting layer is constituted with the above substance such as the alkali metal chalcogenide since the electron injecting property can be further improved. Preferable examples of the alkali metal chalcogenide include $Li_2O$, $K_2O$, $Na_2S$, $Na_2Se$ and $Na_2O$. Preferable examples of the alkaline earth metal chalcogenide include CaO, BaO, SrO, BeO, BaS and CaSe. Preferable examples of the halide of an alkali metal include LiF, NaF, KF, CsF, LiCl, KCl and NaCl. Preferable examples of the halide of an alkaline earth metal include fluorides such as $CaF_2$, $BaF_2$, $SrF_2$, $MgF_2$ and $BeF_2$ and halides other than the fluorides.

Examples of the semiconductor constituting the electron transporting layer include oxides, nitrides and oxide nitrides of at least one metal selected from Ba, Ca, Sr, Yb, Al, Ga, In, Li, Na, Cd, Mg, Si, Ta, Sb and Zn used singly or in combination of two or more. It is preferable that the inorganic compound constituting the electron transporting layer forms a crystallite or amorphous insulating thin film. When the electron injecting layer is constituted with the insulating thin film described above, a more uniform thin film can be formed, and defects of pixels such as dark spots can be decreased. Examples of the inorganic compound include alkali metal chalcogenides, alkaline earth metal chalcogenides, halides of alkali metals and halides of alkaline earth metals which are described above.

For the cathode, a material such as a metal, an alloy, a conductive compound or a mixture of these materials which has a small work function (4 eV or smaller) is used as the electrode material. Examples of the electrode material include sodium, sodium-potassium alloys, magnesium, lithium, cesium, magnesium-silver alloys, aluminum/aluminum oxide, $Al/Li_2O$, $Al/LiO_2$, Al/LiF, aluminum-lithium alloys, indium and rare earth metals.

The cathode can be prepared by forming a thin film of the electrode material described above in accordance with a process such as the vapor deposition process and the sputtering process.

When the light emitted from the light emitting layer is obtained through the cathode, it is preferable that the cathode has a transmittance of the emitted light greater than 10%. It is also preferable that the sheet resistivity of the cathode is several hundred $\Omega/\square$ or smaller. The thickness of the cathode is, in general, selected in the range of 10 nm to 1 μm and preferably in the range of 50 to 200 nm.

Defects in pixels tend to be formed in organic EL device due to leak and short circuit since an electric field is applied to ultra-thin films. To prevent the formation of the defects, a layer of a thin film having an insulating property may be inserted between the pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide. Mixtures and laminates of the above compounds can also be used.

To prepare the organic EL device of the present invention, for example, the anode, the light emitting layer and, where necessary, the hole injecting layer and the electron injecting layer are formed in accordance with the above process using the above materials, and the cathode is formed in the last step. The organic EL device may be prepared by forming the above layers in the order reverse to that described above, i.e., the cathode being formed in the first step and the anode in the last step.

An embodiment of the process for preparing an organic EL device having a construction in which an anode, a hole injecting layer, a light emitting layer, an electron injecting layer and a cathode are disposed successively on a substrate transmitting light will be described in the following.

On a suitable substrate which transmits light, a thin film made of a material for the anode is formed in accordance with the vapor deposition process or the sputtering process so that the thickness of the formed thin film is 1 μm or smaller and preferably in the range of 10 to 200 nm. The formed thin film is used as the anode. Then, a hole injecting layer is formed on the anode. The hole injecting layer can be formed in accordance with the vacuum vapor deposition process, the spin coating process, the casting process or the LB process, as described above. The vacuum vapor deposition process is preferable since a uniform film can be easily obtained and the possibility of formation of pin holes is small. When the hole injecting layer is formed in accordance with the vacuum vapor deposition process, in general, it is preferable that the conditions are suitably selected in the following ranges: the temperature of the source of the deposition: 50 to 450° C.; the vacuum: $10^{-7}$ to $10^{-3}$ Torr; the rate of deposition: 0.01 to 50 nm/second; the temperature of the substrate: −50 to 300° C. and the thickness of the film: 5 nm to 5 μm; although the conditions of the vacuum vapor deposition are different depending on the used compound (the material for the hole injecting layer) and the crystal structure and the recombination structure of the hole injecting layer to be formed.

Then, the light emitting layer is formed on the hole injecting layer formed above. Using a desired organic light emitting material, a thin film of the organic light emitting material can be formed in accordance with the vacuum vapor deposition process, the sputtering process, the spin coating process or the casting process, and the formed thin film is used as the light emitting layer. The vacuum vapor deposition process is preferable since a uniform film can be easily obtained and the possibility of formation of pin holes is small. When the light emitting layer is formed in accordance with the vacuum vapor deposition process, in general, the conditions of the vacuum vapor deposition process can be selected in the same ranges as those described for the vacuum vapor deposition of the hole injecting layer although the conditions are different depending on the used compound. It is preferable that the thickness is in the range of 10 to 40 nm.

The electron injecting layer is formed on the light emitting layer formed above. Similarly to the hole injecting layer and the light emitting layer, it is preferable that the electron injecting layer is formed in accordance with the vacuum vapor deposition process since a uniform film must be obtained. The conditions of the vacuum vapor deposition can be selected in the same ranges as those described for the vacuum vapor deposition of the hole injecting layer and the light emitting layer.

The cathode is formed on the electron injecting layer formed above in the last step, and the organic EL device can be obtained. The cathode is made of a metal and can be formed in accordance with the vacuum vapor deposition process or the sputtering process. It is preferable that the vacuum vapor deposition process is used in order to prevent formation of damages on the lower organic layers during the formation of the film.

In the above preparation of the organic EL device, it is preferable that the above layers from the anode to the cathode are formed successively while the preparation system is kept in a vacuum after being evacuated once.

The process for forming the layers in the organic EL device of the present invention is not particularly limited. A conventional process such as the vacuum vapor deposition process and the spin coating process can be used. The organic thin film layer which is used in the organic EL device of the present invention and comprises the compound represented by general formulae (I) to (III) described above can be formed in accordance with a conventional process such as the vacuum vapor deposition process and the molecular beam epitaxy process (the MBE process) or, using a solution prepared by dissolving the compounds into a solvent, in accordance with a coating process such as the dipping process, the spin coating process, the casting process, the bar coating process and the roll coating process.

The thickness of each layer in the organic thin film layer in the organic EL device of the present invention is not particularly limited. A thickness in the range of several nanometers to 1 μm is preferable so that defects such as pin holes are decreased and the efficiency can be improved.

When a direct voltage is applied to the organic EL device, emission of light can be observed under application of a voltage of 5 to 40 V in the condition that the anode is connected to a positive electrode (+) and the cathode is connected to a negative electrode (−). When the connection is reversed, no electric current is observed and no light is emitted at all. When an alternating voltage is applied to the organic EL device, the uniform light emission is observed only in the condition that the polarity of the anode is positive and the polarity of the cathode is negative. When an alternating voltage is applied to the organic EL device, any type of wave shape can be used.

EXAMPLES

The present invention will be described more specifically with reference to examples in the following. However, the present invention is not limited to the examples as long as the essence of the present invention is maintained.

Synthesis Example 1

Synthesis of AN-4

Under the atmosphere of argon, 20 g of 3,5-dibromobiphenyl synthesized from 3,5-dibromoiodobenzene and phenylboronic acid was dissolved into 200 ml of anhydrous THF, and the resultant solution was cooled at −70° C. To the cooled solution, 42 ml of a 1.6 M hexane solution of normal-butyllithium was added dropwise, and the resultant mixture was stirred for 30 minutes. Then, 19 g of 1,2-diiodoethane was added, and the obtained mixture was stirred for 5 hours. After the mixture was left standing for one night, water and methylene chloride were added. Then, sodium hydrogensulfite was added until dark brown color of the reaction mixture turned to yellow color. The organic layer was obtained by extraction, washed with water and a saturated aqueous solution of sodium chloride and dried with anhydrous sodium sulfate, and the solvent was removed using an evaporator. The obtained residue was purified in accordance with the silica gel column chromatography (the developing solvent: hexane), and 19.5 g of 3-bromo-5-iodobiphenyl was obtained as a colorless oil (the yield: 85%).

Under the atmosphere of argon, 12 g of 3-bromo-5-iodobiphenyl obtained above, 5.7 g of 1-naphthaleneboronic acid and 1.1 g of tetrakis(triphenylphosphine)palladium were dissolved into 100 ml of toluene. To the obtained solution, 55 ml of a 2 M aqueous solution of sodium carbonate was added, and the resultant solution was heated under the refluxing condition for 7 hours. After the solution was cooled by leaving standing, an organic layer was obtained by extraction, washed with water and a saturated aqueous solution of sodium chloride and dried with anhydrous sodium sulfate, and the solvent was removed using an evaporator. The obtained residue was purified in accordance with the silica gel column chromatography (the developing solvent: hexane/toluene=5/1), and 8.1 g of 3-bromo-5-(naphthalen-1-yl)biphenyl was obtained as a white solid substance (the yield: 67%).

Under the atmosphere of argon, 7.6 g of 3-bromo-5-(naphthalen-1-yl)biphenyl obtained above, 8 g of 10-(naphthalen-2-yl)anthracene-9-boronic acid obtained in accordance with a conventional process and 0.95 g of tetrakis(triphenylphosphine)palladium were dissolved into 80 ml of 1,2-dimethoxyethane (DME) and 10 ml of toluene. To the obtained solution, 40 ml of a 2 M aqueous solution of sodium carbonate was added, and the resultant solution was heated under the refluxing condition for 9.5 hours. After the solution was cooled by leaving standing for one night, the formed crystals were separated by filtration and washed with water and methanol and then with heated toluene, and 6.6 g of the object compound (AN-4) was obtained as a white solid substance (the yield: 54%). The obtained compound was examined in accordance with FD-MS (the field desorption mass analysis). Since it was found that m/z=582, which corresponded to $C_{46}H_{30}$=582, the obtained compound was identified to be AN-4.

Synthesis Example 2

Synthesis of AN-10

The same procedures as those conducted in Synthesis Example 1 were conducted except that 2-naphthaleneboronic acid was used in place of 1-naphthaleneboronic acid, and the object compound (AN-10) was obtained as a white solid substance (the yield: 55%). The obtained compound was examined in accordance with FD-MS (the field desorption mass analysis). Since it was found that m/z=582, which corresponded to $C_{46}H_{30}$=582, the obtained compound was identified to be AN-10.

Synthesis Example 3

Synthesis of AN-14

Commercial 2,6-dibromonaphthalene in an amount of 12 g, 11 g of commercial 3-biphenylboronic acid and 180 ml of toluene were mixed together. Then, 5.7 g of tetrakis(triphenylphosphine)palladium and 90 ml of a 2 M aqueous solution of sodium carbonate were added, and the reaction system was purged with argon. After the reaction mixture was heated under the refluxing condition for 7.5 hours, the reaction mixture was cooled by leaving standing. The formed crystals were separated by filtration and subjected to extraction with toluene. The obtained organic layer was washed with water and a saturated aqueous solution of sodium chloride and dried with anhydrous sodium sulfate, and the solvent was removed using an evaporator. The obtained residue was purified in accordance with the silica gel column chromatography (the developing solvent: hexane/toluene=5/1), and 7.8 g of 2-(biphenyl-3-yl)-6-bromonaphthalene was obtained as a white solid substance (the yield: 51%). 2-(Biphenyl-3-yl)-6-bromonaphthalene obtained above in an amount of 5.2 g, 6.4 g of 3-(9-phenylanthracen-10-yl)phenylboronic acid obtained in accordance with a conventional process, 60 ml of DME and 20 ml of toluene were mixed together. To the obtained solution, 0.67 g of tetrakis(triphenylphosphine)palladium and 60 ml of a 2 M aqueous solution of sodium carbonate were added, and the reaction system was purged with argon. After the reaction mixture was heated under the refluxing condition for 10 hours, the reaction mixture was cooled by leaving standing. The formed crystals were separated by filtration, washed with water and methanol and then with heated toluene, and 7.0 g of the object compound (AN-14) was obtained as a white solid substance (the yield: 74%). The obtained compound was examined in accordance with FD-MS (the field desorption mass analysis). Since it was found that m/z=658, which corresponded to $C_{52}H_{34}$=658, the obtained compound was identified to be AN-14.

Synthesis Example 4

Synthesis of AN-22

To 12 g of 2-bromo-6-phenylnaphthalene synthesized in accordance with a conventional process or by the reaction of 2-bromo-6-iodonaphthanlene and phenylboronic acid, 90 ml of anhydrous ether and 30 ml of anhydrous toluene were added, and the reaction system was purged with argon and cooled at -40° C. To the cooled mixture, 29 ml of a 1.6 M hexane solution of normal-butyllithium was added dropwise, and the resultant mixture was stirred for 1 hour. After the obtained mixture was heated to −5° C. and then cooled to −40° C., a solution obtained by diluting 29 ml of boronic acid triisopropyl ester with ether was added dropwise, and the resultant mixture was stirred for 4 hours and then left standing for one night. After the resultant mixture was acidified with a 10% dilute hydrochloric acid, the formed white solid substance was separated by filtration and washed with water and hexane. The amount by weight of white crystals obtained after being dried was 6.8 g. The mother liquor of the filtration was washed with a saturated aqueous solution of sodium chloride and dried with anhydrous sodium sulfate, and the solvent was removed using an evaporator. The obtained light yellow solid substance was washed with methylene chloride and dried, and 3.1 g of white crystals were obtained. The obtained crystals were combined with the crystals obtained above, and 9.9 g of 2-phenylnaphthalene-6-boronic acid was obtained (the yield: 94%).

Under the atmosphere of argon, 6.5 g of 2-phenylnaphthalene-6-boronic acid obtained above and 7.8 g of 3-bromoiodobenzene were dissolved into 100 ml of toluene and 20 ml of DME, and 0.95 g of tetrakis(triphenylphosphine)palladium was added to the obtained solution. After 50 ml of a 2 M aqueous solution of sodium carbonate was added, the resultant mixture was heated under the refluxing condition for 8 hours. After the obtained mixture was left standing for one night, the mixture was subjected to extraction with toluene. The extract was washed with a saturated aqueous solution of sodium chloride, and the solvent was removed using an evaporator. The residue was dissolved into heated toluene and recrystallized, and 6.7 g of 2-(3-bromophenyl)-6-phenylnaphthalene was obtained as white crystals (the yield: 71%).

Under the atmosphere of argon, 6 g of 10-(4-naphthalen-1-ylphenyl)anthracene-9-boronic acid obtained in accordance with a conventional process and 5.1 g of 2-(3-bromophenyl)-6-phenylnaphthalene obtained in accordance with the process described above were dispersed in 80 ml of DME. To the resultant dispersion, 0.5 g of tetrakis(triphenylphosphine)palladium and 24 ml of a 2 M aqueous solution of sodium carbonate were added, and the obtained mixture was heated under the refluxing condition for 8 hours. After the resultant mixture was left standing for one night, the formed crystals were separated by filtration and washed with water and methanol and then with heated toluene, and 5.8 g of the object compound (AN-22) was obtained as a white solid substance (the yield: 62%). The obtained compound was examined in accordance with FD-MS (the field desorption mass analysis). Since it was found that m/z=658, which corresponded to $C_{52}H_{34}$=658, the obtained compound was identified to be AN-22.

Synthesis Example 5

Synthesis of AN-23

To 14 g of 1-bromo-4-phenylnaphthalene synthesized in accordance with a conventional process or by the reaction of 1-bromo-4-iodo-naphthanlene and phenylboronic acid, 130 ml of anhydrous ether and 50 ml of anhydrous toluene were added, and the reaction system was purged with argon and cooled at −40° C. To the cooled mixture, 37 ml of a 1.6 M hexane solution of normal-butyllithium was added dropwise, and the resultant mixture was stirred for 1 hour. After the obtained mixture was heated to −5° C. and then cooled to −40° C., a solution obtained by diluting 34 ml of boronic acid triisopropyl ester with ether was added dropwise, and the resultant mixture was stirred for 3.5 hours and then left standing for one night. After the resultant mixture was acidified with a 10% dilute hydrochloric acid, the reaction mixture was subjected to extraction with ethyl acetate. The extract was washed with a saturated aqueous solution of sodium chloride and dried with anhydrous sodium sulfate, and the solvent was removed using an evaporator. The obtained white solid substance was washed with methylene chloride and dried, and 10 g of 1-phenylnaphthalene-4-boronic acid was obtained as white crystals (the yield: 80%).

Under the atmosphere of argon, 11.6 g of 1-phenylnaphthalene-4-boronic acid and 14.5 g of 3-bromoiodobenzene were dissolved into 160 ml of toluene and 30 ml of DME, and 1.79 g of tetrakis(triphenylphosphine)palladium was added to the obtained solution. After 90 ml of a 2 M aqueous solution of sodium carbonate was added, the resultant mixture was heated under the refluxing condition for 8 hours. After the obtained mixture was left standing for one night, the mixture was subjected to extraction with toluene. The extract was washed with a saturated aqueous solution of sodium chloride, and the solvent was removed using an evaporator. The residue was purified in accordance with the silica gel column chromatography (the developing solvent: hexane/toluene=5/1), and 10.4 g of 1-(3-bromophenyl)-4-phenylnaphthalene was obtained as white crystals (the yield: 62%).

Under the atmosphere of argon, 5.6 g of 10-(4-naphthalen-1-ylphenyl)anthracene-9-boronic acid obtained in accordance with a conventional process and 4.5 g of 1-(3-bromophenyl)-4-phenylnaphthalene obtained in accordance with the process described above were dispersed in 70 ml of DME. To the resultant dispersion, 0.7 g of tetrakis(triphenylphosphine)palladium and 30 ml of a 2 M aqueous solution of sodium carbonate were added, and the obtained mixture was heated under the refluxing condition for 7 hours. After the resultant mixture was left standing for one night, the formed crystals were separated by filtration and washed with water and methanol and then with heated toluene, and 6.7 g of the object compound (AN-23) was obtained as a light yellow solid substance (the yield: 81%). The obtained compound was examined in accordance with FD-MS (the field desorption mass analysis). Since it was found that m/z=658, which corresponded to $C_{52}H_{34}$=658, the obtained compound was identified to be AN-23.

Synthesis Example 6

Synthesis of AN-28

The same procedures as those conducted in Synthesis Example 4 were conducted except that 10-(naphthalen-2-yl)anthracene-9-boronic acid was used in place of 10-(4-naphthalen-1-ylphenyl)anthracene-9-boronic acid, and the object compound (AN-28) was obtained as a gray solid substance (the yield: 79%). The obtained compound was examined in accordance with FD-MS (the field desorption mass analysis). Since it was found that m/z=582, which corresponded to $C_{46}H_{30}$=582, the obtained compound was identified to be AN-28.

Synthesis Example 7

Synthesis of AN-32

To 5.4 g of 2-bromo-6-(naphthalen-1-yl)naphthalene synthesized by the reaction of 2,6-dibromonaphthalene or 2-bromo-6-iodonaphthalene with 1-naphthaleneboronic acid, 20 ml of anhydrous ether and 30 ml of anhydrous toluene were added, and the reaction system was purged with argon and cooled at −30° C. To the cooled mixture, 11 ml of a 1.6 M hexane solution of normal-butyllithium was added dropwise, and the resultant mixture was stirred for 1 hour. After the obtained mixture was heated to −10° C. and then cooled to −70° C., a solution obtained by diluting 11 ml of boronic acid triisopropyl ester with ether was added dropwise, and the resultant mixture was stirred for 3.5 hours and then left standing for one night. After the resultant mixture was acidified with a 10% dilute hydrochloric acid, the reaction mixture was subjected to extraction with ether. The extract was washed with a saturated aqueous solution of sodium chloride and dried with anhydrous sodium sulfate, and the solvent was removed using an evaporator. The obtained white solid substance was washed with methylene chloride and dried, and 3.2 g of 2-(naphthalen-1-yl)naphthalene-6-boronic acid was obtained as white crystals (the yield: 67%).

Under the atmosphere of argon, 3.2 g of 2-(naphthalen-1-yl)naphthalene-6-boronic acid and 2.8 g of 4-bromoiodobenzene were dissolved into 30 ml of toluene, and 0.23 g of tetrakis(triphenyl-phosphine)palladium was added to the obtained solution. After 28 ml of a 2 M aqueous solution of sodium carbonate was added, the resultant mixture was heated under the refluxing condition for 8.5 hours. After the obtained mixture was left standing for one night, the mixture was subjected to extraction with toluene. The extract was washed with a saturated aqueous solution of sodium chloride, and the solvent was removed using an evaporator. The residue was purified in accordance with the silica gel column chromatography (the developing solvent: toluene), and 3.6 g of 2-(4-bromophenyl)-6-(naphthalen-1-yl)naphthalene was obtained as a light yellow solid substance (the yield: 83%).

Under the atmosphere of argon, 4.64 g of 10-(naphthalen-2-yl)anthracene-9-boronic acid obtained in accordance with a conventional process and 4.55 g of 2-(4-bromophenyl)-6-(naphthalen-1-yl)naphthalene obtained in accordance with the process described above were dispersed in 40 ml of DME. To the resultant dispersion, 0.26 g of tetrakis(triphenyl-phosphine)palladium and 25 ml of a 2 M aqueous solution of sodium carbonate were added, and the obtained mixture was heated under the refluxing condition for 8 hours. The formed crystals were separated by filtration and washed with water and methanol and then with heated toluene, and 5.0 g of the object compound (AN-32) was obtained as a gray solid substance (the yield: 71%). The obtained compound was examined in accordance with FD-MS (the field desorption mass analysis). Since it was found that m/z=632, which corresponded to $C_{50}H_{32}$=632, the obtained compound was identified to be AN-32.

Synthesis Example 8

Synthesis of AN-49

Commercial 3-bromoiodobenzene in an amount of 11 g, 8.7 g of commercial 3-biphenylboronic acid and 130 ml of toluene were mixed together. To the resultant mixture, 0.9 g of tetrakis(triphenyl-phosphine)palladium and 75 ml of a 2 M aqueous solution of sodium carbonate were added, and the reaction system was purged with argon. After the reaction mixture was heated under the refluxing condition for 8 hours, the reaction mixture was cooled by leaving standing. The formed crystals were separated by filtration and subjected to extraction with toluene. The organic layer was washed with water and a saturated aqueous solution of sodium chloride and dried with anhydrous sodium sulfate. The solvent was removed using an evaporator. The residue was purified in accordance with the silica gel column chromatography (the developing solvent: hexane), and 11.8 g of 3-bromo-m-terphenyl was obtained as a white solid substance (the yield: 96%).

3-Bromo-m-terphenyl obtained above in an amount of 5.1 g, 7.9 g of 10-(phenanthren-9-yl)anthracene-9-boronic acid synthesized in accordance with a conventional process and 52 ml of DME were mixed together. To the resultant mixture, 0.95 g of tetrakis(triphenylphosphine)palladium and 30 ml of a 2 M aqueous solution of sodium carbonate were added, and the reaction system was purged with argon. After being heated under the refluxing condition for 7.5 hours, the reaction mixture was cooled by leaving standing, and the formed crystals were separated by filtration. The obtained crystals were washed with water and methanol and purified in accordance with the silica gel column chromatography (the developing solvent: hexane/toluene=4/1), and 8.6 g of the object compound (AN-49) was obtained as a white solid substance (the yield: 90%). The obtained compound was examined in accordance with FD-MS (the field desorption mass analysis). Since it was found that m/z=582, which corresponded to $C_{45}H_{30}$=582, the obtained compound was identified to be AN-49.

Synthesis Example 9

Synthesis of AN-52

Under the atmosphere of argon, 11 g of 10-(6-phenylnaphthalen-2-yl)anthracene-9-boronic acid obtained in accordance with a conventional process and 5.7 g of commercial 3-bromobiphenyl were dispersed in 80 ml of DME and 20 ml of toluene. To the obtained dispersion, 1.13 g of tetrakis(triphenylphosphine)palladium and 45 ml of a 2 M aqueous solution of sodium carbonate were added, and the resultant mixture was heated under the refluxing condition for 9 hours. After the mixture was left standing for one night, the formed crystals were separated by filtration and washed with water and methanol and then with heated toluene, and 6.1 g of the object compound (AN-52) was obtained as a light yellow solid substance (the yield: 47%). The obtained compound was examined in accordance with FD-MS (the field desorption mass analysis). Since it was found that m/z=532, which corresponded to $C_{42}H_{28}$=532, the obtained compound was identified to be AN-52.

Synthesis Example 10

Synthesis of AN-53

Under the atmosphere of argon, 8.4 g of 10-(6-phenylnaphthalen-2-yl)anthracene-9-boronic acid obtained in accordance with a conventional process and 5.35 g of 2-(3-bromophenyl)naphthalene were dispersed in 80 ml of DME and 30 ml of toluene. To the obtained dispersion, 0.87 g of tetrakis(triphenylphosphine)palladium and 40 ml of a 2 M aqueous solution of sodium carbonate were added, and the resultant mixture was heated under the refluxing condition for 9 hours. After the mixture was left standing for one night, the formed crystals were separated by filtration and washed with water and methanol and then with heated toluene, and 6.9 g of the object compound (AN-53) was obtained as a light yellow solid substance (the yield: 63%). The obtained compound was examined in accordance with FD-MS (the field desorption mass analysis). Since it was found that m/z=582, which corresponded to $C_{46}H_{30}$=582, the obtained compound was identified to be AN-53.

Synthesis Example 11

Synthesis of AN-85

Under the atmosphere of argon, 8 g of 2-phenylnaphthalene-6-boronic acid obtained in Synthesis Example 4 and 11.6 g of 4-bromo-3'-iodobiphenyl were dissolved into 150 ml of toluene, and 0.75 g of tetrakis(triphenylphosphine)palladium was added to the obtained solution. To the resultant mixture, 49 ml of a 2 M aqueous solution of sodium carbonate was added, and the obtained mixture was heated under the refluxing condition for 8 hours. After the resultant mixture was left standing for one night, the mixture was subjected to extraction with toluene. The extract was washed with a saturated aqueous solution of sodium chloride, and the solvent was removed using an evaporator. The residue was dissolved into heated toluene and recrystallized, and 9.3 g of 4-bromo-3'-(4-phenylnaphthalen-1-yl)biphenyl was obtained as white crystals (the yield: 66%).

Under the atmosphere of argon, 6.2 g of 10-(naphthalen-2-yl)anthracene-9-boronic acid obtained in accordance with a conventional process and 7 g of 4-bromo-3'-(4-phenylnaphthalen-1-yl)biphenyl obtained in accordance with the process described above were dispersed in 100 ml of DME. To the obtained dispersion, 0.38 g of tetrakis(triphenylphosphine)palladium and 25 ml of a 2 M aqueous solution of sodium carbonate were added, and the resultant mixture was heated under the refluxing condition for 8 hours. After the mixture was left standing for one night, the formed crystals were separated by filtration and washed with water and methanol and then with heated toluene, and 6.7 g of the object compound (AN-85) was obtained as a beige solid substance (the yield: 63%). The obtained compound was examined in accordance with FD-MS (the field desorption mass analysis). Since it was found that m/z=658, which corresponded to $C_{52}H_{34}$=658, the obtained compound was identified to be AN-85.

Synthesis Example 12

Synthesis of AN-89

Under the atmosphere of argon, 9.2 g of 10-(3-(naphthalen-2-yl)phenyl)anthracene-9-boronic acid obtained in accordance with a conventional process and 6 g of 2-bromo-6-(naphthalen-2-yl)naphthalene obtained from 2,6-dibromonaphthalene and 2-naphthaleneboronic acid in accordance with a conventional process were dispersed in 150 ml of DME. To the obtained dispersion, 0.42 g of tetrakis(triphenylphosphine)palladium and 27 ml of a 2 M aqueous solution of sodium carbonate were added, and the resultant mixture was heated under the refluxing condition for 8 hours. After the mixture was left standing for one night, the formed crystals were separated by filtration and washed with water and methanol and then with heated toluene, and 7.2 g of the object compound (AN-89) was obtained as a light yellow solid substance (the yield: 63%). The obtained compound was examined in accordance with FD-MS (the field desorption mass analysis). Since it was found that m/z=632, which corresponded to $C_{50}H_{32}=632$, the obtained compound was identified to be AN-89.

Synthesis Example 13

Synthesis of AN-92

Under the atmosphere of argon, 8.4 g of 3-(9-(naphthalen-2-yl)anthracen-10-yl)phenylboronic acid obtained in accordance with a conventional process and 6 g of 2-bromo-6-(naphthalen-2-yl)naphthalene were dispersed in 150 ml of DME. To the obtained dispersion, 0.42 g of tetrakis(triphenylphosphine)palladium and 27 ml of a 2 M aqueous solution of sodium carbonate were added, and the resultant mixture was heated under the refluxing condition for 8 hours. After the mixture was left standing for one night, the formed crystals were separated by filtration and washed with water and methanol and then with heated toluene, and 6.7 g of the object compound (AN-92) was obtained as a light yellow solid substance (the yield: 58%). The obtained compound was examined in accordance with FD-MS (the field desorption mass analysis). Since it was found that m/z=632, which corresponded to $C_{50}H_{32}=632$, the obtained compound was identified to be AN-92.

Synthesis Example 14

Synthesis of AN-95

Under the atmosphere of argon, 9.9 g of 10-(3-(naphthalen-2-yl)phenyl)anthracene-9-boronic acid obtained in accordance with a conventional process and 7 g of 2-bromo-6-(3-biphenyl)naphthalene were dispersed in 150 ml of DME. To the obtained dispersion, 0.45 g of tetrakis(triphenylphosphine)palladium and 30 ml of a 2 M aqueous solution of sodium carbonate were added, and the resultant mixture was heated under the refluxing condition for 7.5 hours. After the mixture was left standing for one night, the formed crystals were separated by filtration and washed with water and methanol and then with heated toluene, and 7.2 g of the object compound (AN-95) was obtained as a light yellow solid substance (the yield: 56%). The obtained compound was examined in accordance with FD-MS (the field desorption mass analysis). Since m/z=658 corresponding to $C_{52}H_{34}=658$, the obtained compound was identified to be AN-95.

Synthesis Example 15

Synthesis of AN-96

The same procedures as those conducted in Synthesis Example 14 were conducted except that 10-(4-(naphthalen-1-yl)-phenyl)anthracene-9-boronic acid was used in place of 10-(3-(naphthalen-2-yl)phenyl)anthracene-9-boronic acid, and the object compound (AN-96) was obtained as a cream-colored solid substance (the yield: 61%). The obtained compound was examined in accordance with FD-MS (the field desorption mass analysis). Since it was found that m/z=658, which corresponded to $C_{52}H_{34}=658$, the obtained compound was identified to be AN-96.

Synthesis Example 16

Synthesis of AN-99

Under the atmosphere of argon, 9.8 g of 4-(9-(naphthalen-2-yl)anthracen-10-yl)phenylboronic acid obtained in accordance with a conventional process and 7 g of 1-bromo-4-(naphthalen-2-yl)naphthalene obtained from 1,4-dibromonaphthalene and 2-naphthaleneboronic acid in accordance with a conventional process were dispersed in 150 ml of DME. To the obtained dispersion, 0.49 g of tetrakis(triphenylphosphine)palladium and 32 ml of a 2 M aqueous solution of sodium carbonate were added, and the resultant mixture was heated under the refluxing condition for 8 hours. After the mixture was left standing for one night, the formed crystals were separated by filtration and washed with water and methanol and then with heated toluene, and 7.6 g of the object compound (AN-99) was obtained as a light yellow solid substance (the yield: 57%). The obtained compound was examined in accordance with FD-MS (the field desorption mass analysis). Since it was found that m/z=632, which corresponded to $C_{50}H_{32}=632$, the obtained compound was identified to be AN-99.

Example 1

Evaluation of AN-10

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The cleaned glass substrate having the transparent electrode was attached to a substrate holder of a vacuum vapor deposition apparatus. On the surface of the cleaned substrate at the side having the transparent electrode, a film of N,N'-bis(N,N'-diphenyl-4-aminophenyl)-N,N-diphenyl-4,4'-diamino-1,1'-biphenyl shown below (referred to as "TPD232 film", hereinafter) having a thickness of 60 nm was formed in a manner such that the formed film covered the transparent electrode. The formed TPD232 film worked as the hole injecting layer. On the formed TPD232 film, a film of N,N,N',N'-tetra(4-biphenyl)diaminobiphenylene shown below (referred to as "TBDB film", hereinafter) having a thickness of 20 nm was formed. The formed TBDB film worked as the hole transporting layer. On the formed TBDB film, AN-10 was vapor deposited to form a film having a thickness of 40 nm. At the same time, an amine compound having styryl group (BD1) shown below as the light emitting molecule was vapor deposited in an amount such that the ratio of the amounts by weight of AN-10 to BD1 were 40:2. The formed film worked as the light emitting layer. On the formed film, a film of Alq shown below having a thickness of 10 nm was formed. This film worked as the electron injecting layer. On the film formed above, Li (the source of lithium: manufactured by SAES GETTERS Company) as the reducing dopant and Alq were binary vapor deposited, and an Alq:Li film (the thickness: 10 nm) was formed as the electron injecting layer (or the cathode). On the formed Alq:Li film, metallic aluminum was vapor deposited to form a metal cathode, and an organic EL device was prepared. The obtained organic EL device was examined by passing electric current. Blue light was emitted at a luminance of emitted light of 660 cd/m² under a voltage of 6.93 V and a current density of 10 mA/cm². The initial luminance was set at 1,000 cd/m², and the half life of the obtained organic EL device was measured. The result is shown in Table 1. The glass transition temperature (Tg) of AN-10 used as the host material is shown in Table 1.

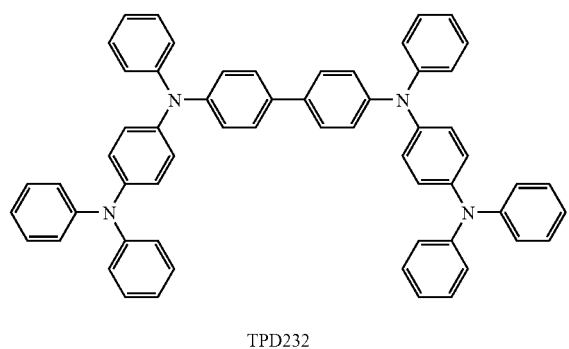

TPD232

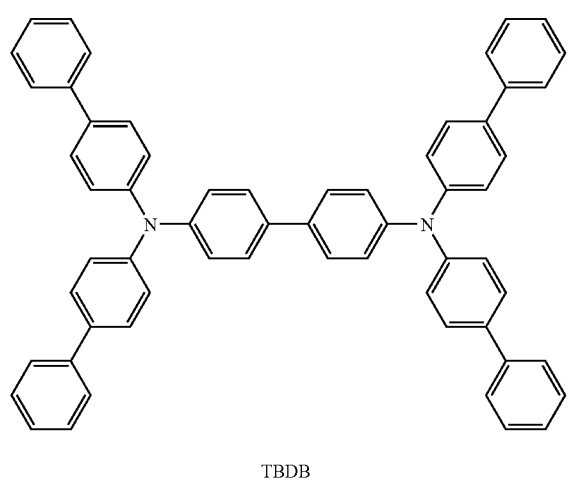

TBDB

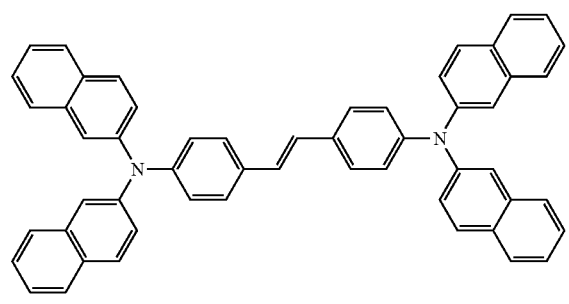

BD1

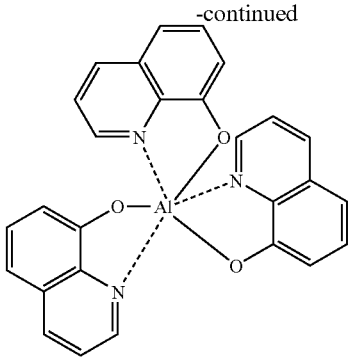

Alq

Examples 2 to 6

Organic EL devices were prepared in accordance with the same procedures as those conducted in Example 1 except that compounds shown in Table 1 were used as the material for the light emitting layer in place of AN-10. The initial luminance was set at 1,000 cd/m², and the half life of the obtained organic EL devices was measured. The results are shown in Table 1. The glass transition temperatures (Tg) of the host materials are shown in Table 1.

Example 7

An organic EL device was prepared in accordance with the same procedures as those conducted in Example 1 except that an amine compound BD2 was used as the material for the light emitting layer in place of the amine compound BD1, and the half life was measured in accordance with the same procedures as those conducted in Example 1. The result is shown in Table 1. The glass transition temperatures (Tg) of AN-10 used as the host material is shown in Table 1.

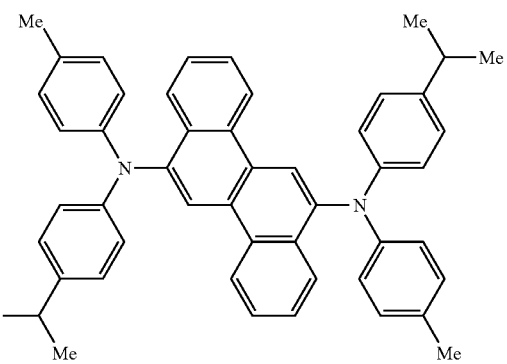

BD2

Example 8

An organic EL device was prepared in accordance with the same procedures as those conducted in Example 1 except that an amine compound BD3 was used as the material for the light emitting layer in place of the amine compound BD1, and the half life was measured in accordance with the same procedures as those conducted in Example 1. The result is shown in Table 1. The glass transition temperatures (Tg) of AN-10 used as the host material is shown in Table 1.

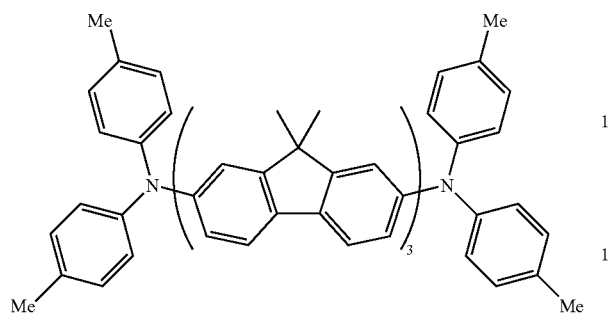

BD3

Examples 9 to 14

Organic EL devices were prepared in accordance with the same procedures as those conducted in Example 1 except that compounds shown in Table 1 were used as the material for the light emitting layer in place of AN-10. The initial luminance was set at 1,000 cd/m$^2$, and the half life of the obtained organic EL devices was measured. The results are shown in Table 1. The glass transition temperatures (Tg) of the host materials are shown in Table 1.

Comparative Examples 1 to 10

Organic EL devices were prepared in accordance with the same procedures as those conducted in Example 1 except that compounds shown in Table 1 were used as the material for the light emitting layer in place of AN-10. The initial luminance was set at 1,000 cd/m$^2$, and the half life of the obtained organic EL devices was measured. The results are shown in Table 1. The glass transition temperatures (Tg) of the host materials are shown in Table 1.

Comparative Example 11

An organic EL device was prepared in accordance with the same procedures as those conducted in Example 1 except that, as the materials for the light emitting layer, an-3 was used in place of AN-10 and the amine compound BD2 was used in place of the amine compound BD1. The initial luminance was set at 1,000 cd/m$^2$, and the half life of the obtained organic EL device was measured. The result is shown in Table 1. The glass transition temperatures (Tg) of an-3 used as the host material is shown in Table 1.

Comparative Example 12

An organic EL device was prepared in accordance with the same procedures as those conducted in Example 1 except that an-11 was used as the materials for the light emitting layer in place of AN-10. The initial luminance was set at 1,000 cd/m$^2$, and the half life of the obtained organic EL device was measured. The result is shown in Table 1. The glass transition temperatures (Tg) of the host material is shown in Table 1.

Chemical structures of the compounds used in Comparative Examples are as shown in the following:

TABLE 1

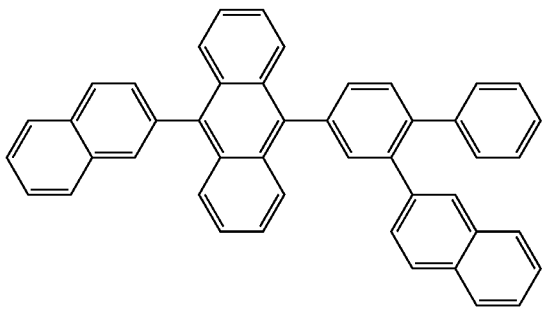

an-1

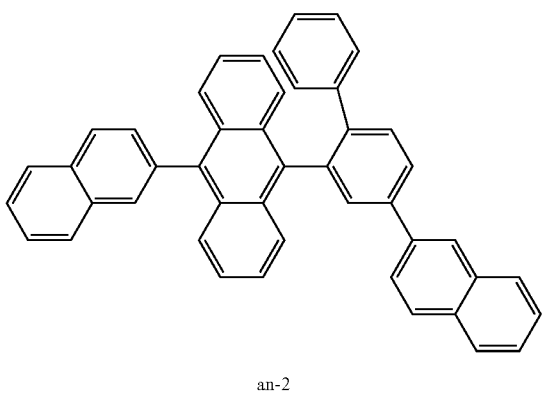

an-2

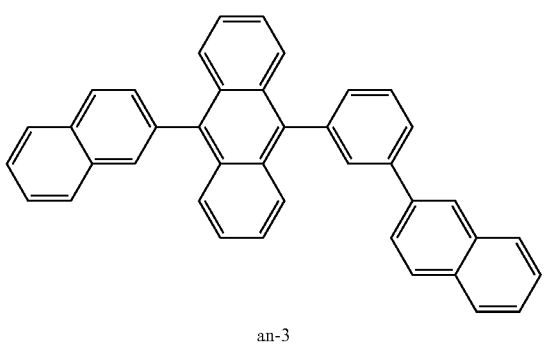

an-3

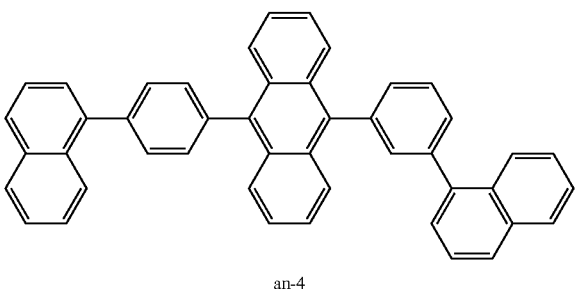

an-4

TABLE 1-continued

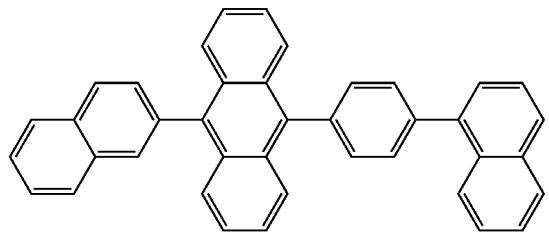

an-5

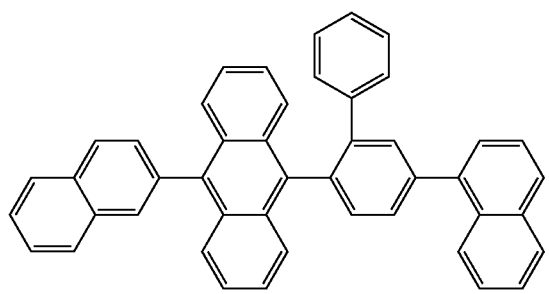

an-6

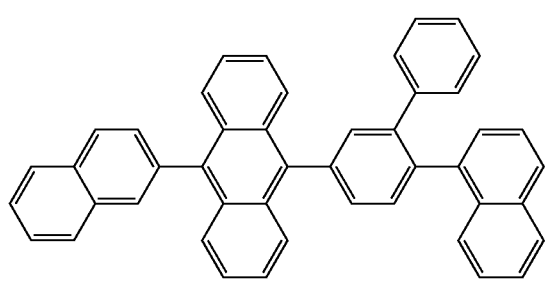

an-7

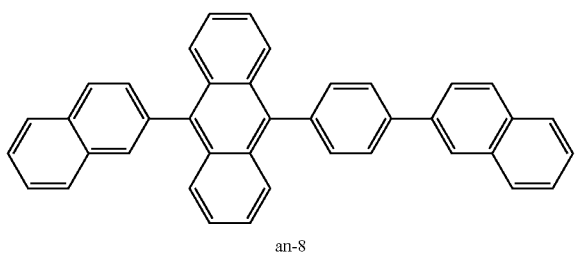

an-8

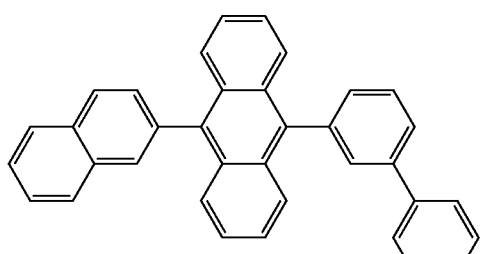

an-9

TABLE 1-continued

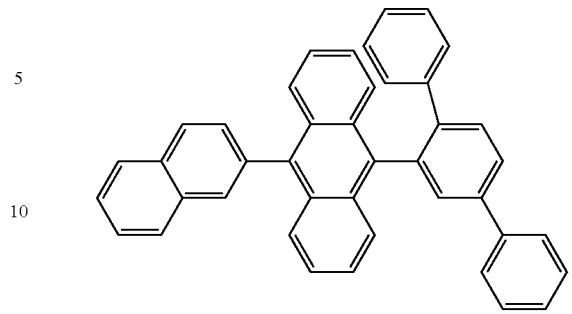

an-10

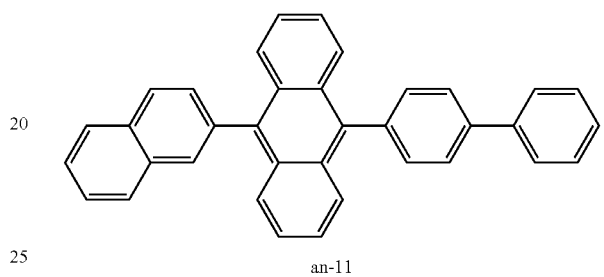

an-11

| Compound of light emitting layer | Half life (hour) | Glass transition temperature (° C.) |
|---|---|---|
| Example 1 | AN-10/BD1 | 8,100 | 140 |
| Example 2 | AN-22/BD1 | 8,100 | 135 |
| Example 3 | AN-23/BD1 | 6,800 | 137 |
| Example 4 | AN-32/BD1 | 7,350 | 151 |
| Example 5 | AN-52/BD1 | 8,200 | 120 |
| Example 6 | AN-53/BD1 | 8,500 | 128 |
| Example 7 | AN-10/BD2 | 7,000 | 140 |
| Example 8 | AN-10/BD3 | 6,400 | 140 |
| Example 9 | AN-85/BD1 | 8,100 | 149 |
| Example 10 | AN-89/BD1 | 8,700 | 131 |
| Example 11 | AN-92/BD1 | 8,500 | 140 |
| Example 12 | AN-95/BD1 | 8,600 | 125 |
| Example 13 | AN-96/BD1 | 8,100 | 143 |
| Example 14 | AN-99/BD1 | 8,600 | 127 |
| Comparative Example 1 | an-1/BD1 | 2,500 | 144 |
| Comparative Example 2 | an-2/BD1 | 3,500 | 131 |
| Comparative Example 3 | an-3/BD1 | 8,000 | 115 |
| Comparative Example 4 | an-4/BD1 | 3,560 | 121 |
| Comparative Example 5 | an-5/BD1 | 5,600 | 130 |
| Comparative Example 6 | an-6/BD1 | 3,650 | 135 |
| Comparative Example 7 | an-7/BD1 | 2,500 | 148 |
| Comparative Example 8 | an-8/BD1 | 3,200 | not detected |
| Comparative Example 9 | an-9/BD1 | 6,000 | 104 |
| Comparative Example 10 | an-10/BD1 | 3,500 | 123 |
| Comparative Example 11 | an-3/BD2 | 6,700 | 115 |
| Comparative Example 12 | an-11/BD1 | 3,000 | not detected |

When the compounds an-3 and an-9 were used as described in Comparative Examples, the glass transition temperature was low although the obtained organic EL devices had long lives. The compounds an-1, an-2 and an-10 which were obtained by introducing aromatic hydrocarbon groups into the above compounds provided markedly decreased lives although the glass transition temperature was improved. On the other hand, the compounds AN-10, AN-52 and AN-53 which are compounds shown as examples of the compound of the present invention and were obtained by introducing aromatic hydrocarbon groups at specifically designated positions achieved further increases in the life while the glass transition temperature was improved.

The compound an-5 described in a Comparative Example had a relatively high glass transition temperature and provided a relatively long life. However, the compounds an-6 and an-7 which were obtained by introducing aromatic hydrocarbon groups to further improve the glass transition temperature provided markedly decreased lives although the glass transition temperature was improved. On the other hand, the compound AN-32 which is a compound shown as an example of the compound of the present invention and was obtained by introducing aromatic hydrocarbon groups at specifically designated positions had a markedly improved glass transition temperature and achieved a further increase in the life. AN-32 provided a longer life in comparison with an-8 described in a Comparative Example.

The compound AN-23 which was obtained by introducing aromatic hydrocarbon groups into the compound an-4 described in a Comparative Example and AN-22 which was an analogue thereof had remarkably improved glass transition temperatures and provided long lives.

As the result of intensive studies by the present inventors on the position of introduction of aromatic groups effective for elevating the glass transition temperature (Tg), it was found that the glass transition temperature could be improved while the life of the device was maintained only when aromatic hydrocarbon groups were introduced in a manner satisfying the conditions shown in the following, and that the life of the device was markedly decreased although the glass transition temperature was improved when aromatic hydrocarbon groups were introduced in a manner not satisfying the conditions shown in the following.

(a) One or more aromatic hydrocarbon groups or aromatic heterocyclic groups are introduced into the group represented by $Ar^2$ in general formulae (I) to (III), i.e, cases excluding [q=r=0 and Y representing hydrogen atom].

(b) When no aromatic hydrocarbon groups or aromatic heterocyclic groups are introduced into the group represented by $Ar^2$ in general formulae (I) to (III), i.e, in the case of [q=r=0 and Y representing hydrogen atom], either one of the following conditions must be satisfied:

(i) s≠0 or Z does not represent hydrogen atom in general formula (II).

(ii) p≠0 or X does not represent hydrogen atom in general formulae (I) to (III).

As the above results show, the anthrylarylene derivative of the present invention has a higher glass transition temperature and provides a longer life than those in conventional technology.

INDUSTRIAL APPLICABILITY

As described above specifically, the light emitting material used in the organic EL device of the present invention comprises an anthrylarylene derivative having a sufficient glass transition temperature. The organic EL device using the anthrylarylene derivative of the present invention exhibits a great efficiency of light emission and has a long life. Therefore, the organic EL device of the present invention is valuable in practical applications and can be advantageously used as the light sources such as the planar light emitting material for wall televisions and the back light for displays. The derivative can also be used as the hole injecting and transporting material for organic EL devices and the charge transporting material for electronic photosensitive materials and organic semiconductors.

The invention claimed is:

1. An anthrylarylene derivative represented by the following general formula (5):

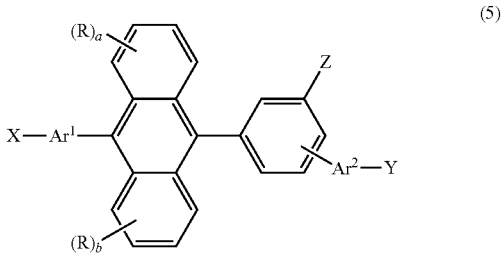

wherein $Ar^1$ and $Ar^2$ each independently represents an unsubstituted phenyl group or an unsubstituted naphthyl group;

X represents a naphthyl group or a pyrenyl, Y represents a phenyl group or a naphthyl group and Z represents a hydrogen atom;

R represents an aromatic hydrocarbon group, an aromatic heterocyclic group, an alkyl group, a cycloalkyl group, an alkoxy group, an aralkyl group, an aryloxy group, an arylthio group, an alkoxycarbonyl group, a silyl group, carboxyl group, a halogen atom, cyano group, nitro group or hydroxyl group;

when R represents an alkyl group in general formula (5), adjacent alkyl groups may be bonded to each other to form a condensed ring; and a and b each independently represents an integer of 0 to 4.

2. An organic electroluminescence device which comprises a cathode, an anode and an organic thin film layer which comprises at least one layer comprising at least a light emitting layer and is disposed between the cathode and the anode, wherein at least one layer in the organic thin film layer comprises the anthrylarylene derivative described in claim 1 singly or as a component of a mixture.

3. An organic electroluminescence device according to claim 2, wherein the light emitting layer comprises the anthrylarylene derivative singly or as a component of a mixture.

4. An organic electroluminescence device according to claim 3, wherein the light emitting layer comprises the anthrylarylene derivative singly or as a component of a mixture as a main component.

5. An organic electroluminescence device according to claim 3, wherein the light emitting layer further comprises an arylamine compound.

6. An organic electroluminescence device according to claim 3, wherein the light emitting layer further comprises a styrylamine compound.

* * * * *